United States Patent
Ogi et al.

(10) Patent No.: US 7,951,548 B2
(45) Date of Patent: May 31, 2011

(54) IL-13 PRODUCTION INHIBITOR

(75) Inventors: Kazuhiro Ogi, Ibaraki (JP); Yusuke Kikukawa, Osaka (JP); Tsukasa Sugo, Ibaraki (JP); Tokuyuki Shinohara, Ibaraki (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 173 days.

(21) Appl. No.: 11/884,259

(22) PCT Filed: Feb. 15, 2006

(86) PCT No.: PCT/JP2006/303099
§ 371 (c)(1),
(2), (4) Date: Aug. 13, 2007

(87) PCT Pub. No.: WO2006/088219
PCT Pub. Date: Aug. 24, 2006

(65) Prior Publication Data
US 2009/0170116 A1    Jul. 2, 2009

(30) Foreign Application Priority Data
Feb. 16, 2005 (JP) ................. 2005-038859

(51) Int. Cl.
*G01N 33/566* (2006.01)
*G01N 33/53* (2006.01)
*G01N 33/567* (2006.01)

(52) U.S. Cl. ......... 435/7.21; 435/7.2; 436/501; 436/503

(58) Field of Classification Search ........................ None
See application file for complete search history.

(56) References Cited

FOREIGN PATENT DOCUMENTS

| EP | 1455186 | 9/2004 |
|---|---|---|
| JP | 2005-325055 | 11/2005 |
| WO | WO-03-052414 | 6/2003 |
| WO | WO-2005-028667 | 3/2005 |

OTHER PUBLICATIONS

Aoki et al, Biochimica et Biophysica Acta, 2002, vol. 1582, pp. 26-32.*
Wells, 1990, Biochemistry 29:8509-8517.*
T. Sugo, et al., "Identification of a lysophosphatidylserine receptor on mast cells" *Biochem. Biophys. Res. Commun.*, vol. 341, No. 4, p. 1078-1087 (Mar. 24, 2006).
A. Schulz, et al., "The structural evolution of a P2Y-like G-protein-coupled receptor," J. Biol. Chem., vol. 278, No. 37, p. 35531-35541 (2003).

* cited by examiner

*Primary Examiner* — Bridget E Bunner
*Assistant Examiner* — Fozia M Hamud
(74) *Attorney, Agent, or Firm* — Edwards Angell Palmer & Dodge LLP; David G. Conlin; Lisa Swiszcz

(57) ABSTRACT

The present invention provides a screening method/screening kit for an IL-13 production inhibitor, which comprises using (a) a protein comprising the same or substantially the same amino acid sequence as the amino acid sequence represented by SEQ ID NO: 1, or its partial peptide, or a salt thereof; and (b) a ligand capable of specifically binding to the protein; an IL-13 production inhibitor which is obtainable by said screening, and the like. The IL-13 production inhibitor which can be obtained by the screening of the present invention is useful as a prophylactic/therapeutic agent for, e.g., respiratory disease, etc.

5 Claims, 9 Drawing Sheets

IL-13 PRODUCTION INHIBITOR

RELATED APPLICATIONS

This application is the national phase filing of International Patent Application No.: JP/2006/303099 Feb. 15, 2005, which claims priority to Japanese Patent Application No.: 038859/2005 filed Feb. 16, 2005, the entirety of which is incorporated herein by reference.

TECHNICAL FIELD

The present invention relates to screening methods and screening kits for interleukin-13 production inhibitors, etc., using GPR34 or mast cells and ligands of GPR34; interleukin-13 production inhibitors which are obtainable using the screening methods or kits, and so on. The present invention also relates to screening methods and screening kits for eicosanoid production inhibitors, mast cell degranulation inhibitors, mast cell growth inhibitors, etc., using GPR34 or mast cells and the ligands of GPR34; eicosanoid production inhibitors, mast cell degranulation inhibitors or mast cell growth inhibitors, which are obtainable using the screening methods or kits, and so on. The present invention further relates to screening methods and screening kits for prophylactic/therapeutic agents for central nervous disorders, using microglial cells and ligands of GPR34; prophylactic/therapeutic agents for central nervous disorders, which are obtainable using the screening methods or kits, and so on.

BACKGROUND ART

As ligands of G protein-coupled receptor GPR34, lipids (e.g., ether phospholipids, phosphonoether lipids, glycerophospholipids, phosphonoglycerolipids, sphingolipids, sphingophospholipids, phosphonosphingolipids, etc.) are reported (WO 03/052414).

It is known that lysophosphatidylserine which is one of glycerophospholipids (hereinafter sometimes referred to as lyso-PS) has the histamine release activity on rat mast cells stimulated by an antigen or concanavalin A (Nature, 279, 250-252, 1979; FEBS Lett., 105, 58-62, 1979), the activity of releasing histamine by synergistically acting on rat mast cells together with nerve growth factor (FEBS Lett., 138, 190-192, 1982), the growth regulating activity on human T cells (FEBS Lett., 316, 1-4, 1993), and the activity of potentiating the differentiation-inducing ability of NGF on PC 12 cells (Neurosci. Lett., 248, 77-80, 1998).

Mast cells cause degranulation by antigenic stimulation after sensitization with an antibody to release chemical mediators such as histamine, leukotriene, serotonin, etc., and are deeply involved in type I hypersensitivity reaction. On the other hand, mast cells secrete various cytokines after antigenic stimulation to affect the functions of T cells and eosinophils and are important as immune regulatory cells.

In late years it is suggested that interleukin-13 (hereinafter IL-13), which is one of cytokines, plays a more important role than IL-4 in the pathology of allergic diseases. IL-13 mRNA is expressed in local areas such as the lichenified lesion of a patient with atopic dermatitis, the airway epithelial cells of a patient with bronchial asthma, the nasal mucosa of a patient with chronic allergic rhinitis, etc. and is considered to relate to IgE production. In bronchial asthma or the like, eosinophils and mast cells are accumulated in respiratory submucosal tissues or epithelial cells. It is thus considered that IL-13 expressed therein may be produced mainly by mast cells, clearly indicating that IL-13 acts directly on bronchial epithelial cells or smooth muscle to cause airway hyperresponsiveness or increased mucus production. Also, IL-13 draws attention as a cause not only for allergic disease but for Hodgkin's disease, ulcerative colitis, pulmonary fibrosis, granuloma, etc.

DISCLOSURE OF THE INVENTION

Under the situations described above, it has been desired to develop screening compounds having excellent IL-13 production inhibitory activities.

The present inventors have made extensive studies to solve the foregoing problems and as a result, found that GPR34 is abundantly expressed in mast cells, stimulation of mast cells with lysoPS increases IL-13 expression and lysoPS promotes degranulation reaction via GPR34, and also found novel guinea pig GPR34 and monkey GPR34. The present inventors further found that GPR34 is expressed in microglial cells in the central nervous system to exert its anti-inflammatory action through lysoPS stimulation. Based on these findings, the present inventors have found that GPR34 antagonists act as IL-13 production inhibitors and provide simple methods for screening the IL-13 production inhibitors, and that screening methods using mast cells and ligands of GPR34 are useful for screening eicosanoid production inhibitors, mast cell degranulation inhibitors, mast cell growth inhibitors, etc., and further that microglial cells and the ligands of GPR34 are effective for screening prophylactic/therapeutic agents for central nervous disorders, and so on. As a result of more extensive investigations, the present invention has come to be accomplished.

The present invention relates to the following features, and so on.

[1] A method for screening an IL-13 production inhibitor, which comprises using (a) a protein comprising the same or substantially the same amino acid sequence as the amino acid sequence represented by SEQ ID NO: 1, or its partial peptide, or a salt thereof; and (b) a compound represented by the formula:

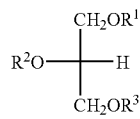

wherein R¹ represents a hydrogen atom or an optionally substituted hydrocarbon group or an acyl;
each of R² and R³ represents hydrogen, an optionally substituted hydrocarbon group, an acyl, or a group shown by the following formula:

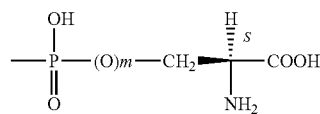

wherein m represents 0 or 1, and S represents absolute configuration, or a salt thereof (hereinafter referred to as Ligand A).

[2] The screening method according to [1] above, wherein the compound is lysophosphatidyl-L-serine.

[3] The screening method according to [1] above, wherein the protein comprising substantially the same amino acid sequence represented by SEQ ID NO: 1 is a protein comprising the amino acid sequence represented by SEQ ID NO: 19, SEQ ID NO: 22, SEQ ID NO: 31 or SEQ ID NO: 35.

[4] The screening method according to [1] above, wherein the protein consisting of the amino acid sequence represented by SEQ ID NO: 1 or a salt thereof and lysophosphatidyl-L-serine are used.

[5] The screening method according to [1] through [4] above, which comprises assaying a cell stimulating activity mediated by a protein comprising the same or substantially the same amino acid sequence as the amino acid sequence represented by SEQ ID NO: 1, or its partial peptide, or a salt thereof, and using the activity as an indicator.

[6] The screening method according to [1] above, wherein the IL-13 production inhibitor is a prophylactic/therapeutic agent for an immune disease, a respiratory disease, a urologic disease or a circulatory disease.

[7] A kit for screening an IL-13 production inhibitor, which comprises (a) a protein comprising the same or substantially the same amino acid sequence as the amino acid sequence represented by SEQ ID NO: 1, or its partial peptide, or a salt thereof; and (b) Ligand A.

[8] A method for screening an IL-13 production inhibitor, which comprises using a mast cell and Ligand A.

[9] A kit for screening an IL-13 production inhibitor, which comprises a mast cell and Ligand A.

[10] An IL-13 production inhibitor, which comprises a compound or its salt that inhibits the activity of (a) a protein comprising the same or substantially the same amino acid sequence as the amino acid sequence represented by SEQ ID NO: 1, or its partial peptide, or a salt thereof, or (b) Ligand A.

[10a] An IL-13 production inhibitor, which comprises an antagonist of a protein comprising the same or substantially the same amino acid sequence as the amino acid sequence represented by SEQ ID NO: 1, or its partial peptide, or a salt thereof.

[11] A method for inhibiting IL-13 production, which comprises inhibiting the activity of (a) a protein comprising the same or substantially the same amino acid sequence as the amino acid sequence represented by SEQ ID NO: 1, or its partial peptide, or a salt thereof, or (b) Ligand A.

[12] An IL-13 production inhibitor, which comprises an antibody against a protein comprising the same or substantially the same amino acid sequence as the amino acid sequence represented by SEQ ID NO: 1, or its partial peptide, or a salt thereof.

[13] An IL-13 production inhibitor, which comprises a polynucleotide comprising the whole or a part of a base sequence complementary or substantially complementary to a polynucleotide encoding a protein comprising the same or substantially the same amino acid sequence as the amino acid sequence represented by SEQ ID NO: 1, or a partial peptide of the protein, or a salt thereof.

[14] An IL-13 production inhibitor, which comprises a siRNA or shRNA against a polynucleotide encoding a protein comprising the same or substantially the same amino acid sequence as the amino acid sequence represented by SEQ ID NO: 1, or a partial peptide of the protein, or a salt thereof.

[15] An IL-13 production inhibitor, which comprises an antibody against a protein comprising the same or substantially the same amino acid sequence as the amino acid sequence represented by SEQ ID NO: 1, or its partial peptide, or a salt thereof.

[16] A method for screening an eicosanoid production inhibitor, which comprises using (a) a protein comprising the same or substantially the same amino acid sequence as the amino acid sequence represented by SEQ ID NO: 1, or its partial peptide, or a salt thereof, and (b) Ligand A.

[16a] The screening method according to [16] above, wherein the eicosanoid is a leukotriene.

[16b] The screening method according to [16] above, wherein the eicosanoid is a prostaglandin.

[17] The screening method according to [16] above, wherein the compound is lysophosphatidyl-L-serine.

[18] The screening method according to [16] above, wherein the eicosanoid production inhibitor is a prophylactic/therapeutic agent for an immune disease, a respiratory disease, a urologic disease or a circulatory disease.

[19] A kit for screening an eicosanoid production inhibitor, which comprises (a) a protein comprising the same or substantially the same amino acid sequence as the amino acid sequence represented by SEQ ID NO: 1, or its partial peptide, or a salt thereof, and (b) Ligand A.

[20] A method for screening an eicosanoid production inhibitor, which comprises using a mast cell and Ligand A.

[21] A kit for screening an eicosanoid production inhibitor, which comprises a mast cell and Ligand A.

[22] An eicosanoid production inhibitor, which comprises a compound or its salt that inhibits the activity of (a) a protein comprising the same or substantially the same amino acid sequence as the amino acid sequence represented by SEQ ID NO: 1, or its partial peptide, or a salt thereof, or (b) Ligand A.

[22a] An eicosanoid production inhibitor, which comprises an antagonist of a protein comprising the same or substantially the same amino acid sequence as the amino acid sequence represented by SEQ ID NO: 1, or its partial peptide, or a salt thereof.

[23] A method for inhibiting eicosanoid production, which comprises inhibiting the activity of (a) a protein comprising the same or substantially the same amino acid sequence as the amino acid sequence represented by SEQ ID NO: 1, or its partial peptide, or a salt thereof, or (b) Ligand A.

[24] An eicosanoid production inhibitor, which comprises an antibody against a protein comprising the same or substantially the same amino acid sequence as the amino acid sequence represented by SEQ ID NO: 1, or its partial peptide, or a salt thereof.

[25] An eicosanoid production inhibitor, which comprises a polynucleotide comprising the whole or a part of a base sequence complementary or substantially complementary to a polynucleotide encoding a protein comprising the same or substantially the same amino acid sequence as the amino acid sequence represented by SEQ ID NO: 1, or a partial peptide of the protein, or a salt thereof.

[26] An eicosanoid production inhibitor, which comprises a siRNA or shRNA against a polynucleotide encoding a protein comprising the same or substantially the same amino acid sequence as the amino acid sequence represented by SEQ ID NO: 1, or a partial peptide of the protein, or a salt thereof.

[27] An eicosanoid production inhibitor, which comprises an antibody against a protein comprising the same or substantially the same amino acid sequence as the amino acid sequence represented by SEQ ID NO: 1, or its partial peptide, or a salt thereof.

[28] A method for screening a mast cell degranulation inhibitor, which comprises using (a) a protein comprising the same or substantially the same amino acid sequence as the amino acid sequence represented by SEQ ID NO: 1, or its partial peptide, or a salt thereof, and (b) Ligand A.
[29] The screening method according to [28] above, wherein the compound is lysophosphatidyl-L-serine.
[30] The screening method according to [28] above, wherein the mast cell degranulation inhibitor is a prophylactic/therapeutic agent for an immune disease, a respiratory disease, a urologic disease or a circulatory disease.
[31] A kit for screening a mast cell degranulation inhibitor, which comprises (a) a protein comprising the same or substantially the same amino acid sequence as the amino acid sequence represented by SEQ ID NO: 1, or its partial peptide, or a salt thereof, and (b) Ligand A.
[32] A method for screening a mast cell degranulation inhibitor, which comprises using a mast cell and Ligand A.
[33] A kit for screening a mast cell degranulation inhibitor, which comprises a mast cell and Ligand A.
[34] A mast cell degranulation inhibitor, which comprises a compound or its salt that inhibits the activity of (a) a protein comprising the same or substantially the same amino acid sequence as the amino acid sequence represented by SEQ ID NO: 1, or its partial peptide, or a salt thereof, or (b) Ligand A.
[34a] A mast cell degranulation inhibitor, which comprises an antagonist of a protein comprising the same or substantially the same amino acid sequence as the amino acid sequence represented by SEQ ID NO: 1, or its partial peptide, or a salt thereof.
[35] A method for inhibiting degranulation of a mast cell, which comprises inhibiting the activity of (a) a protein comprising the same or substantially the same amino acid sequence as the amino acid sequence represented by SEQ ID NO: 1, or its partial peptide, or a salt thereof, or (b) Ligand A.
[36] A mast cell degranulation inhibitor, which comprises an antibody against a protein comprising the same or substantially the same amino acid sequence as the amino acid sequence represented by SEQ ID NO: 1, or its partial peptide, or a salt thereof.
[37] A mast cell degranulation inhibitor, which comprises a polynucleotide comprising the whole or a part of a base sequence complementary or substantially complementary to a polynucleotide encoding a protein comprising the same or substantially the same amino acid sequence as the amino acid sequence represented by SEQ ID NO: 1, or a partial peptide of the protein, or a salt thereof.
[38] A mast cell degranulation inhibitor, which comprises a siRNA or shRNA against a polynucleotide encoding a protein comprising the same or substantially the same amino acid sequence as the amino acid sequence represented by SEQ ID NO: 1, or a partial peptide of the protein, or a salt thereof.
[39] A mast cell degranulation inhibitor, which comprises an antibody against an agonist of a protein comprising the same or substantially the same amino acid sequence as the amino acid sequence represented by SEQ ID NO: 1, or its partial peptide, or a salt thereof.
[40] A method for screening a compound or its salt that promotes or inhibits the activation of a protein comprising the same or substantially the same amino acid sequence as the amino acid sequence represented by SEQ ID NO: 1, or its partial peptide, or a salt thereof, which comprises assaying the activity of ERK1 (extracellular signal-regulated kinase 1) and/or ERK2 (extracellular signal-regulated kinase 2) mediated by said protein, its partial peptide, or a salt thereof, using (a) said protein, or its partial peptide, or a salt thereof, and (b) Ligand A.

[41] A method for screening a mast cell growth or differentiation inhibitor, which comprises assaying the activity of ERK1 (extracellular signal-regulated kinase 1) and/or ERK2 (extracellular signal-regulated kinase 2) mediated by a protein comprising the same or substantially the same amino acid sequence as the amino acid sequence represented by SEQ ID NO: 1, or its partial peptide, or a salt thereof, using (a) said protein, or its partial peptide, or a salt thereof and (b) Ligand A.
[42] A method for screening a prophylactic/therapeutic agent for central nervous disorders, which comprises using (a) microglial cells and (b) Ligand A.
[43] The screening method according to [42] above, wherein Ligand A is lysophosphatidyl-L-serine.
[44] The screening method according to [42] above, wherein the central nervous disorders are neurodegenerative disease (e.g., Alzheimer's disease (familial Alzheimer's disease, juvenile Alzheimer's disease, sporadic Alzheimer's disease, etc.).
[45] A kit for screening a prophylactic/therapeutic agent for central nervous disorders, which comprises (a) microglial cells and (b) Ligand A.
[46] A prophylactic/therapeutic agent for central nervous disorders, which comprises a compound or its salt (a) that inhibits the activity of a protein comprising the same or substantially the same amino acid sequence as the amino acid sequence represented by SEQ ID NO: 1, or its partial peptide, or a salt thereof, or (b) that inhibits the activity of Ligand A.
[46a] A prophylactic/therapeutic agent for central nervous disorders, which comprises an antagonist of a protein comprising the same or substantially the same amino acid sequence as the amino acid sequence represented by SEQ ID NO: 1, or its partial peptide, or a salt thereof.
[47] A method of preventing/treating central nervous disorders, which comprises (a) inhibiting the activity of a protein comprising the same or substantially the same amino acid sequence as the amino acid sequence represented by SEQ ID NO: 1, or its partial peptide, or a salt thereof, or (b) inhibiting the activity of Ligand A.
[48] A prophylactic/therapeutic agent for central nervous disorders, which comprises an antibody against a protein comprising the same or substantially the same amino acid sequence as the amino acid sequence represented by SEQ ID NO: 1, or its partial peptide, or a salt thereof.
[49] A prophylactic/therapeutic agent for central nervous disorders, which comprises a polynucleotide comprising the whole or a part of a base sequence complementary or substantially complementary to a polynucleotide encoding a protein comprising the same or substantially the same amino acid sequence as the amino acid sequence represented by SEQ ID NO: 1, or a partial peptide of the protein, or a salt thereof.
[50] A prophylactic/therapeutic agent for central nervous disorders, which comprises a siRNA or shRNA against a polynucleotide encoding a protein comprising the same or substantially the same amino acid sequence as the amino acid sequence represented by SEQ ID NO: 1, or a partial peptide of the protein, or a salt thereof.
[51] A prophylactic/therapeutic agent for central nervous disorders, which comprises an antibody against an agonist of a protein comprising the same or substantially the same amino acid sequence as the amino acid sequence represented by SEQ ID NO: 1, or its partial peptide, or a salt thereof.

The present invention further provides the following features, and so on.

(1) A method for screening an IL-13 production inhibitor, which comprises using (a) a protein comprising the same or substantially the same amino acid sequence as the amino acid sequence represented by SEQ ID NO: 1, or its partial peptide, or a salt thereof and (b) a ligand capable of specifically binding to said protein or a salt thereof.

(2) The screening method according to (1) above, wherein the ligand is a lipid.

(3) The screening method according to (1) above, wherein the ligand is an ether phospholipid, a phosphono-ether lipid, a glycerophospholipid or a phosphono-glycerolipid.

(4) The screening method according to [1] above, wherein the ligand is a compound represented by the formula below:

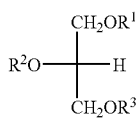
(I)

wherein $R^1$ represents a hydrogen atom or an optionally substituted hydrocarbon group or an acyl;

each of $R^2$ and $R^3$ represents hydrogen, an optionally substituted hydrocarbon group, an acyl, or a group shown by the formula below:

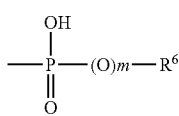
(III)

wherein $R^6$ represents a hydrogen atom, an optionally substituted alkyl, or an optionally substituted cycloalkyl, and m is 0 or 1 (hereinafter sometimes briefly referred to as Group (III)); or a salt thereof ((hereinafter sometimes briefly referred to as Compound (I)).

(5) The screening method according to (4) above, wherein $R^1$ is an acyl.

(6) The screening method according to (4) above, wherein $R^2$ is a hydrogen atom or an acyl.

(7) The screening method according to (4) above, wherein $R^3$ is Group (III).

(8) The screening method according to (1) above, wherein the ligand is represented by the formula below:

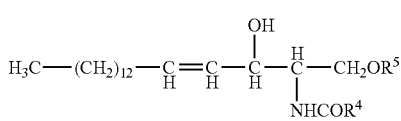
(II)

wherein $R^4$ represents a hydrogen atom, an optionally substituted hydrocarbon group or an acyl;

$R^5$ represents a hydrogen atom, an optionally substituted hydrocarbon group, an acyl, or a group shown by the formula below:

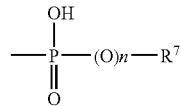
(IV)

wherein $R^7$ represents a hydrogen atom, an optionally substituted alkyl or an optionally substituted cycloalkyl, and n is 0 or 1 (hereinafter sometimes briefly referred to as Group (IV)); or a salt thereof.

(9) The screening method according to (1) above, wherein the ligand is lysophosphatidylserine or phosphatidylserine

(10) A protein comprising the amino acid sequence represented by SEQ ID NO: 31, or its partial peptide, or a salt thereof.

(11) A protein comprising the amino acid sequence represented by SEQ ID NO: 35, or its partial peptide, or a salt thereof.

The compound (e.g., the antagonist of the receptor of the present invention) that inhibits the activity/function of the protein comprising the same or substantially the same amino acid sequence as the amino acid sequence represented by SEQ ID NO: 1, or its partial peptides, or salts thereof (the receptor of the present invention) or the ligands capable of specifically binding to the receptor of the present invention (the ligands of the present invention) are useful as low-toxic and safe IL-13 production inhibitors, mast cell degranulation inhibitors, eicosanoid (e.g., leukotriene, prostaglandin, etc.) production inhibitors, mast cell growth inhibitors, etc., as prophylactic/therapeutic agents for, e.g., immune disorders [e.g., inflammatory diseases (pituitary tumor, thyroiditis, peritonitis, Crohn's disease, ulcerative colitis, erythema nodosum, chronic rheumatoid arthritis, systemic lupus erythematosus, etc.), allergy (e.g., allergic conjunctivitis, allergic rhinitis, pollinosis, metal allergy, etc.), asthma, exudative otitis media, Meniere's disease, contact dermatitis, anaphylaxis, urticaria, myasthenia gravis, glomerulonephritis, Sjögren's syndrome, Basedow's disease, insulin resistant diabetes, atopic dermatitis, leukocyte abnormality, etc.], respiratory disorders [e.g., chronic obstructive pulmonary disease (e.g., chronic bronchitis, pulmonary emphysema), diffuse panbronchiolitis, cystic fibrosis, hypersensitivity penumonitis, idiopathic interstitial pneumonia, pulmonary fibrosis, etc.], urinary tract disorders (e.g., renal tubulointerstitial injuries (fibrosis), interstitial cystitis, allergic cystitis, etc.), circulatory diseases (e.g., arteriosclerosis, acute coronary syndrome, atherosclerotic aortic aneurysm, cardiac anaphylaxis, heart failure, myocardial infarction, angina pectoris, arrhythmia, deep venous thrombosis, restenosis after PTCA, etc.), ophthalmic disorders (e.g., pterygium, vernal catarrh, dry eyes, etc.), cancer (e.g., papillary thyroid carcinoma, non-small cell lung cancer, endometrial cancer, cervical cancer, gastric cancer, pancreatic cancer, lung cancer, renal cancer, liver cancer, ovarian cancer, prostate cancer, bladder cancer, breast cancer, colon cancer, rectal cancer, Kaposi's sarcoma, mastocytoma, etc.), digestive disorders [e.g., chronic liver disease, food allergy, allergic enteritis, milk protein-induced proctitis, peptic ulcer (e.g., gastric ulcer, duodenal ulcer, marginal ulcer, Zollinger-Ellison syndrome, etc.), gastritis, reflux esophagitis, NUD (Non Ulcer Dyspepsia), gastric MALT lymphoma, non-steroidal anti-inflammatory drug-induced ulcer, hyperacidity, postoperative stress-induced hyperacidity and ulcer, etc.], cerebral infarction, hyperlipemia, acute renal failure, diabetes mellitus, obesity, edema, granuloma, atopic myelitis, neurofibroma, nasal mucosa hypersensitivity, Hodgkin's disease, endometrial hyperplasia, central nervous disorders [e.g., neurodegenerative disease (e.g., Alzheimer's disease (familial Alzheimer's disease, juvenile Alzheimer's disease, sporadic Alzheimer's disease, etc.), Parkinson's disease, Down's syndrome, amyotrophic lateral sclerosis, prion disease (Creutzfeldt-Jakob disease), Huntington's chorea, diabetic neuropathy, multiple sclerosis, etc.), mental disorders (e.g., schizophrenia, depression, bipolar disorders, anxiety disorders, attention deficit hyperactivity disorders, panic disorders, etc.), cerebrovascular disorders (e.g., cerebral thrombosis, cerebral embolism, transient ischemic attack, etc.), etc.] and the like Furthermore, by the screening method or screening kit using the receptor of the present invention and the ligand of the present invention, the compound or its salt having the IL-13 production inhibitory action, mast cell degranulation inhibitory action, eicosanoid production inhibitory action, mast cell growth inhibitory action, etc. can be efficiently obtained.

In addition, the receptor of the present invention and the ligand of the present invention are used to assay the activity of extracellular signal-regulated kinase 1 (ERK1) and/or extracellular signal-regulated kinase 2 (ERK2) mediated by the receptor of the present invention, and the compound or its salt that promotes or inhibits the activation of the receptor of the present invention can be efficiently screened by using the activity as an indicator. The compound is useful as a mast cell growth or differentiation inhibitor.

Furthermore, prophylactic/therapeutic agents for central nervous disorders can be screened by the screening method or the screening kit using microglial cells and the ligand of the present invention.

BEST MODE FOR CARRYING OUT THE INVENTION

Figure 1:
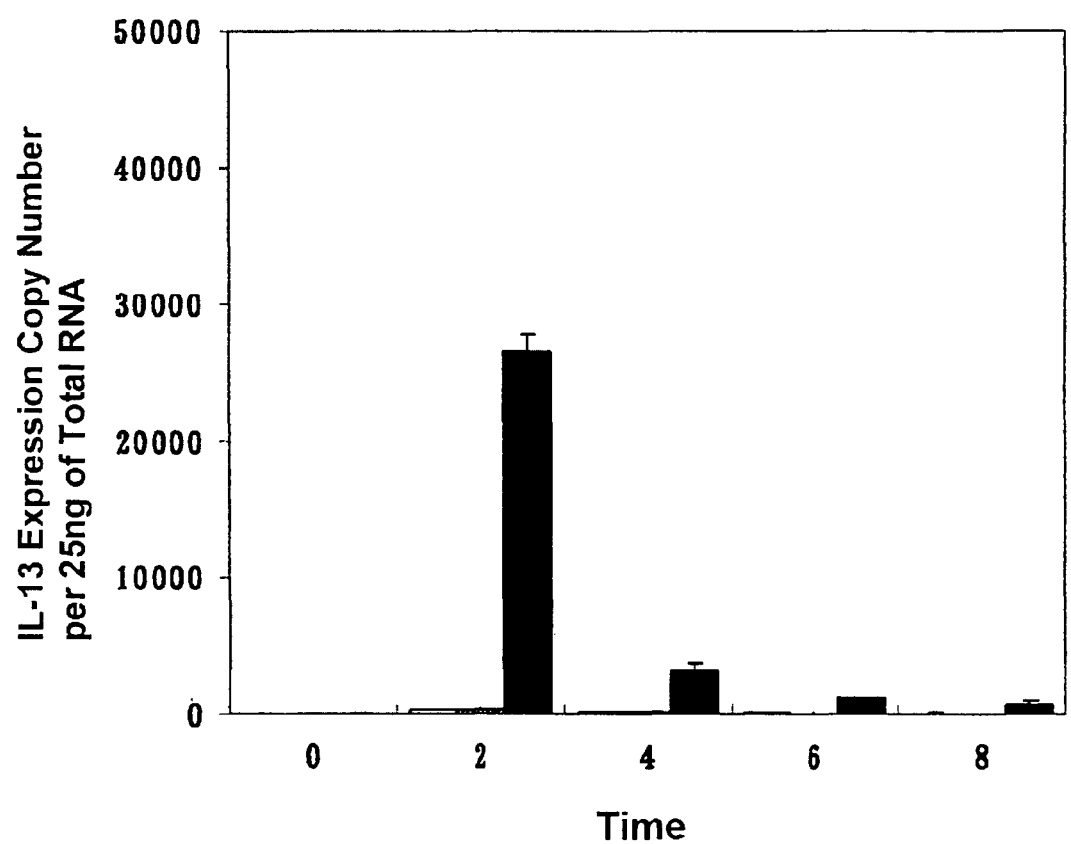
FIG. 1 shows actions on the expression levels of rat IL-13 using rat peritoneal mast cells when stimulated by DNP-BSA or lysoPS. In the figure, white bar denotes a ratio of the IL-13 expression level to the GAPDH expression level without any stimulation, hatched bar denotes a ratio of the IL-13 expression level to the GAPDH expression level when stimulated by DNP-BSA, and black bar denotes a ratio of the IL-13 expression level to the GAPDH expression level when simulated by DNP-BSA and lysoPS.

Hereinafter, the term "protein comprising the same or substantially the same amino acid sequence as the amino acid sequence represented by SEQ ID NO: 1, its partial peptide, or its salt" is sometimes referred to as "the receptor of the present invention." Further, the term "ligand capable of specifically binding to the receptor of the present invention" is sometimes referred to as "the ligand of the present invention".

The protein having the same or substantially the same amino acid sequence as the amino acid sequence represented by SEQ ID NO: 1 may be any protein derived from any cells of human and warm-blooded animals (e.g., guinea pigs, rats, mice, fowl, rabbits, swine, sheep, bovine, monkeys, etc.) (e.g., retinal cells, hepatocytes, splenocytes, nerve cells, glial cells, β cells of pancreas, bone marrow cells, mesangial cells, Langerhans' cells, epidermic cells, epithelial cells, endothelial cells, fibroblasts, fibrocytes, myocytes, fat cells, immune cells (e.g., macrophage, T cells, B cells, natural killer cells, mast cells, neutrophils, basophils, eosinophils, monocytes), megakaryocytes, synovial cells, chondrocytes, bone cells, osteoblasts, osteoclasts, mammary gland cells, hepatocytes or interstitial cells; or the corresponding precursor cells, stem cells, cancer cells, etc.); or any tissues where such cells are present, such as brain or any of brain regions (e.g., retina, olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, joint, skeletal muscle, etc.; or proteins derived from hemocyte type cells or their cultured cells (e.g., MEL, M1, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01, LAD1, LAD2, etc.); these proteins may also be synthetic proteins.

The amino acid sequence having substantially the same amino acid sequence as that represented by SEQ ID NO: 1 includes amino acid sequences having at least about 70% homology, preferably at least about 80% homology, more preferably at least about 90% homology, to the amino acid sequence shown by SEQ ID NO: 1; and so on.

Examples of the protein comprising substantially the same amino acid sequence as the amino acid sequence represented by SEQ ID NO: 1 include proteins having substantially the same amino acid sequence as the amino acid sequence represented by SEQ ID NO: 1 and having an activity of substantially the same property as that of the protein having the amino acid sequence represented by SEQ ID NO: 1, etc. The amino acid sequence which is substantially the same as the amino acid sequence represented by SEQ ID NO: 1 includes e.g., an amino acid sequence represented by SEQ ID NO: 19, SEQ ID NO: 22, SEQ ID NO: 31, SEQ ID NO: 35, etc.

Examples of the substantially equivalent activity include a ligand binding activity, a signal transduction activity, etc. The term substantially equivalent is used to mean that the activities are the same in nature. Therefore, it is preferred that activities such as the ligand binding and signal transduction activities, etc. are equivalent (e.g., about 0.01 to 100 times, preferably about 0.5 to 20 times, more preferably 0.5 to 2 times), but differences in degree such as a level of these activities, quantitative factors such as a molecular weight of the protein may be present and allowable.

The activities such as ligand binding and signal transduction activities or the like can be determined according to publicly known methods with some modifications thereof. For example, the activities can be assayed in accordance with the methods of determining ligands or screening methods which will be later described.

Examples of the proteins of the present invention include those having the following amino acid sequences: (i) the amino acid sequence represented by SEQ ID NO: 1, wherein at least 1 or 2 amino acids (e.g., approximately 1 to 100 amino acids, preferably approximately 1 to 50 amino acids, preferably approximately 1 to 30 amino acids, more preferably approximately 1 to 10 amino acids, and most preferably several (1 to 5) amino acids) are deleted; (ii) the amino acid sequence represented by SEQ ID NO: 1, to which at least 1 or 2 amino acids (e.g., approximately 1 to 100 amino acids, preferably approximately 1 to 50 amino acids, preferably approximately 1 to 30 amino acids, more preferably approximately 1 to 10 amino acids, most preferably several (1 to 5) amino acids) are added; (iii) the amino acid sequence represented by SEQ ID NO: 1, in which at least 1 or 2 amino acids (e.g., approximately 1 to 100 amino acids, preferably approximately 1 to 50 amino acids, more preferably approximately 1 to 30 amino acids, much more preferably approximately 1 to 10 amino acids, and most preferably several (1 to 5) amino acids) are substituted by other amino acids; (iv) the amino acid sequence represented by SEQ ID NO: 1, in which at least 1 or 2 amino acids (e.g., approximately 1 to 100 amino acids, preferably approximately 1 to 50 amino acids, more preferably approximately 1 to 30 amino acids, much more preferably approximately 1 to 10 amino acids, and most preferably several (1 to 5) amino acids) are inserted; or (v) combination of these amino acid sequences.

The partial peptide of the receptor of the present invention (hereinafter sometimes referred to as the partial peptide of the present invention) may be any partial peptide so long as it is a partial peptide which can be used for the methods of screening medicaments later described. Among the protein molecules of the present invention, for example, those having the site exposed to the outside of a cell membrane and retaining substantially the same ligand binding activity, etc. may be employed.

Specifically, the partial peptide of receptor protein having the amino acid sequence represented by SEQ ID NO: 1 is a peptide containing the portion analyzed to be an extracellular domain (hydrophilic domain) in the hydrophobic plotting analysis. A peptide containing a hydrophobic domain in part can be used as well. In addition, the peptide may contain each domain separately or a plurality of domains together.

In the partial peptides of the present invention, preferred are peptides having at least 20, preferably at least 50, and more preferably at least 100 amino acids, in the amino acid sequence which constitutes the protein of the present invention.

Herein, the term "substantially equivalent activity" is intended to mean the same significance as defined above. The "substantially equivalent activity" can be assayed in the same way as described above.

The partial peptide of the present invention may contain amino acid sequences, (i) wherein at least 1 or 2 amino acids (preferably approximately 1 to 10 amino acids, and more preferably several (1 to 5) amino acids) are deleted; (ii) wherein at least 1 or 2 amino acids (preferably approximately 1 to 20 amino acids, more preferably approximately 1 to 10 amino acids, and most preferably several (1 to 5) amino acids) are added; or, (iii) wherein at least 1 or 2 amino acids (preferably approximately 1 to 10 amino acids, more preferably several and most preferably approximately 1 to 5 amino acids) are substituted by other amino acids.

Specific examples are partial peptides containing the amino acid sequences of 1st to 53rd, 114th to 128th, 197th to 216th, or 293rd to 310th in the amino acid sequence represented by SEQ ID NO: 1, partial peptides containing the amino acid sequences of 1st to 46th, 107th to 121st, 190th to 209th, 286th to 303rd in the amino acid sequence represented by SEQ ID NO: 19, and the like.

The receptor of the present invention and the partial peptide of the present invention are represented in accordance with the conventional way of describing peptides that is, the N-terminus (amino terminus) at the left hand and the C-terminus (carboxyl terminus) at the right hand. The C-terminus may be in any form of a carboxyl group (—COOH), a carboxylate (—COO—), an amide (—CONH$_2$) or an ester (—COOR).

Herein, examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl such as a phenyl-$C_{1-2}$ alkyl group, e.g., benzyl, phenethyl, etc.; an α-naphthyl-$C_{1-2}$ alkyl group such as α-naphthylmethyl, etc.; pivaloyloxymethyl and the like.

Where the receptor of the present invention and partial peptide of the present invention contain a carboxyl group (or a carboxylate) at a position other than the C-terminus, the carboxyl group may be amidated or esterified and such an amide or ester is also included within the receptor of the present invention or the partial peptide of the present invention. Examples of the ester group in this case may be the C-terminal esters described above, etc.

Furthermore, examples of the receptor of the present invention and the partial peptide of the present invention include variants wherein the amino group at the N-terminal amino acid residues (e.g., methionine residue) is protected with a protecting group (e.g., a $C_1$ acyl group such as a $C_{1-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{1-6}$ alkanoyl group, e.g., formyl group, acetyl group, etc.), or conjugated proteins such as glycoproteins having sugar chains; etc.

As salts of the receptor of the present invention or the partial peptide of the present invention, salts with physiologically acceptable acids (e.g., inorganic acids or organic acids) or bases (e.g., alkali metal salts) may be employed, preferably in the form of physiologically acceptable acid addition salts. Examples of such salts include salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

Examples of the ligand of the present invention can be any ligand so long as the ligand specifically binds to the receptor of the present invention. Examples of the ligand are those having a dissociation constant in binding to the protein or its salt of 10 μM or less, preferably not greater than 2 μM, more preferably not greater than 1 μM, much more preferably not greater than 200 nM, and most preferably not greater than 100 nM, and the like.

The ligands of the present invention used include, for example, lipids, etc. Specifically, phospholipids such as phosphonolipid, etc. are used as well. Preferably, ether phospholipid, phosphono-ether lipid, glycerophospholipid, phosphonoglycerolipid, sphingolipid, sphingophospholipid, phosphonosphingolipid, etc. are used. Among them, ether phospholipid, phosphono-ether lipid, glycerophospholipid and phosphonoglycerolipid are preferred. Glycerophospholipid is more preferred.

The ligands of the present invention further include mixtures of two or more members selected from ether phospholipid, phosphono-ether lipid, glycerophospholipid, phosphonoglycerolipid, sphingolipid, sphingophospholipid, phosphonosphingolipid, and the like.

The ether phospholipid, phosphono-ether lipid, glycerophospholipid and phosphonoglycerolipid are shown by, e.g., Compound (I), etc.

Preferably, Compound (I) includes compounds represented by the formula below or their salts.

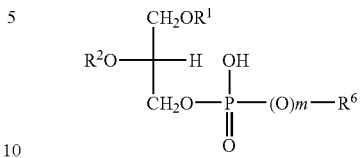

wherein all symbols have the same significance as defined above.

More preferably, Compound (I) includes compounds represented by the formula below or their salts.

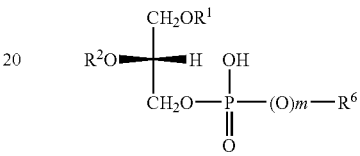

wherein all symbols have the same significance as defined above.

More preferably, Compound (1) includes compounds represented by the formula below or their salts.

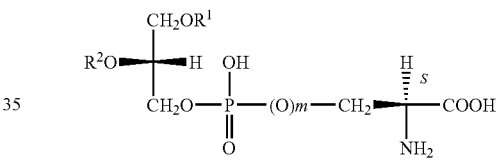

wherein all symbols have the same significance as defined above.

In these formulae, the "hydrocarbon group" in the "optionally substituted hydrocarbon group" shown by $R^1$, $R^2$ or $R^3$ includes, for example, alkyl, alkenyl, alkynyl, cycloalkyl, etc. The number of carbons is preferably 1 to 30.

Examples of the "alkyl" include a $C_{1-30}$ alkyl (e.g., methyl, ethyl, propyl, isopropyl, butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl, triacontyl, etc.), and the like; preferably a $C_{9-30}$ alkyl, etc., and more preferably, a $C_{13-19}$ alkyl such as tridecyl, tetradecyl, pentadecyl, hexadecyl, heptadecyl, octadecyl, nonadecyl, etc.

Examples of the "alkenyl" include a $C_{2-30}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl, hexenyl, heptenyl, octenyl, nonenyl, decenyl, undecenyl, dodecenyl, tridecenyl, tetradecenyl, tetradecadienyl, pentadecenyl, pentadecadienyl, hexadecenyl, hexadecadienyl, heptadecenyl, heptadecadienyl, heptadecatrienyl, octadecenyl, octadecadienyl, nonadecenyl, nonadecadienyl, nonadecatrienyl, nonadecatetraenyl, icosenyl, icosadienyl, henicosenyl, docosenyl, tricosenyl, tetracosenyl, pentacosenyl, hexacosenyl, heptacosenyl, octacosenyl, nonacosenyl, triacontenyl, etc.) and the like; preferably a $C_{13-19}$ alkenyl.

Examples of the "alkynyl" include a $C_{2-30}$ alkynyl (e.g., ethynyl, propargyl, 1-butynyl, 2-butynyl, 3-butynyl, 1-hexynyl, tetradecynyl, pentadecynyl, hexadecynyl, heptadecynyl, octadecynyl, nonadecynyl, icosynyl, henicosynyl, docosynyl, tricosynyl, tetracosynyl, pentacosynyl, hexacosynyl, heptacosynyl, octacosynyl, nonacosynyl, triacontynyl, etc.), and the like; preferably a $C_{15-17}$ alkynyl.

Examples of the "cycloalkyl" include a $C_{3-6}$ cycloalkyl (e.g., cyclopropyl, cyclobutyl, cyclopentyl, cyclohexyl, etc.), and the like.

The "acyl" shown by $R^1$, $R^2$ or $R^3$ includes groups represented by formula: —CO—$R^8$, —(C=O)—$OR^8$, —(C=O)—$NR^8R^9$, —SO—$R^{10}$ or —$SO_2$—$R^{10}$ (wherein, $R^8$ represents hydrogen atom, an optionally substituted hydrocarbon group or an optionally substituted heterocyclic group; $R^9$ represents hydrogen atom or a $C_{1-6}$ alkyl; and $R^{10}$ represents an optionally substituted hydrocarbon group or an optionally substituted heterocyclic group), etc., preferably groups represented by formula: —CO—$R^8$.

The "hydrocarbon group" in "the optionally substituted hydrocarbon group," which is represented by $R^8$ or $R^{10}$, includes the above-described "hydrocarbon group" shown by $R^1$, $R^2$ or $R^3$.

In the "optionally substituted hydrocarbon group" as used herein, examples of the "substituent(s)" include a halogen atom (e.g., fluorine, chloride, bromine, iodine, etc.), a $C_{1-3}$ alkylenedioxy (e.g., methylenedioxy, ethylenedioxy, etc.), nitro, cyano, an optionally halogenated $C_{1-6}$ alkyl (e.g., methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc.), a $C_{2-6}$ alkenyl, a $C_{2-6}$ alkynyl, an optionally halogenated $C_{3-6}$ cycloalkyl (e.g., cyclopropyl, cyclobutyl, cyclopentyl, cyclohexyl, 4,4-dichlorocyclohexyl, 2,2,3,3-tetrafluorocyclopentyl, 4-chlorocyclohexyl, etc.), a $C_{6-14}$ aryl (e.g., phenyl, 1-naphthyl, 2-naphthyl, 2-biphenylyl, 3-biphenylyl, 4-biphenylyl, 2-anthryl, etc.), an optionally halogenated $C_{1-8}$ alkoxy (e.g., methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, etc.), hydroxy, a $C_{6-14}$ aryloxy (e.g., phenyloxy, 1-naphthyloxy, 2-naphthyloxy, etc.), a $C_{7-16}$ aralkyloxy (e.g., benzyloxy, phenethyloxy, etc.), mercapto, an optionally halogenated $C_{1-6}$ alkylthio (e.g., methylthio, difluoromethylthio, trifluoromethylthio, ethylthio, propylthio, isopropylthio, butylthio, 4,4,4-trifluorobutylthio, pentylthio, hexylthio, etc.), a $C_{6-14}$ arylthio (e.g., phenylthio, 1-naphthylthio, 2-naphthylthio, etc.), a $C_{7-16}$ aralkylthio (e.g., benzylthio, phenethylthio, etc.), amino, a mono-$C_{1-6}$ alkylamino (e.g., methylamino, ethylamino, etc.), a mono-$C_{6-14}$ arylamino (e.g., phenylamino, 1-naphthylamino, 2-naphthylamino, etc.), a di-$C_{1-6}$ alkylamino (e.g., dimethylamino, diethylamino, ethylmethylamino, etc.), a di-$C_{6-14}$ arylamino (e.g., diphenylamino, etc.), formyl, carboxy, a $C_{1-6}$ alkyl-carbonyl (e.g., acetyl, propionyl, etc.), a $C_{3-6}$ cycloalkyl-carbonyl (e.g., cyclopropylcarbonyl, cyclopentylcarbonyl, cyclohexylcarbonyl, etc.), a $C_{1-6}$ alkoxy-carbonyl (e.g., methoxycarbonyl, ethoxycarbonyl, propoxycarbonyl, tert-butoxycarbonyl, etc.), a $C_{6-14}$ aryl-carbonyl (e.g., benzoyl, 1-naphthoyl, 2-naphthoyl, etc.), a $C_{7-16}$ aralkyl-carbonyl (e.g., phenylacetyl, 3-phenylpropionyl, etc.), a $C_{6-14}$ aryloxy-carbonyl (e.g., phenoxycarbonyl, etc.), a $C_{7-16}$ aralkyloxy-carbonyl (e.g., benzyloxycarbonyl, phenethyloxycarbonyl, etc.), a 5- or 6-membered heterocyclic carbonyl (e.g., nicotinoyl, isonicotinoyl, thenoyl, furoyl, morpholinocarbonyl, thiomorpholinocarbonyl, piperazin-1-ylcarbonyl, pyrrolidin-1-ylcarbonyl, etc.), carbamoyl, a mono-$C_{1-6}$ alkyl-carbamoyl (e.g., methylcarbamoyl, ethylcarbamoyl, etc.), a di-$C_{1-6}$ alkyl-carbamoyl (e.g., dimethylcarbamoyl, diethylcarbamoyl, ethylmethylcarbamoyl, etc.), a $C_{6-14}$ aryl-carbamoyl (e.g., phenylcarbamoyl, 1-naphthylcarbamoyl, 2-naphthylcarbamoyl, etc.), a 5- or 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl, etc.), a $C_{1-6}$ alkylsulfonyl (e.g., methylsulfonyl, ethylsulfonyl, etc.), a $C_{6-14}$ arylsulfonyl (e.g., phenylsulfonyl, 1-naphthylsulfonyl, 2-naphthylsulfonyl, etc.), formylamino, a $C_{1-6}$ alkyl-carbonylamino (e.g., acetylamino, etc.), a $C_{6-14}$ aryl-carbonylamino (e.g., benzoylamino, naphthoylamino, etc.), a $C_{1-6}$ alkoxy-carbonylamino (e.g., methoxycarbonylamino, ethoxycarbonylamino, propoxycarbonylamino, butoxycarbonylamino, etc.), a $C_{1-6}$ alkylsulfonylamino (e.g., methylsulfonylamino, ethylsulfonylamino, etc.), a $C_{6-14}$ arylsulfonylamino (e.g., phenylsulfonylamino, 2-naphthylsulfonylamino, 1-naphthylsulfonylamino, etc.), a $C_{1-6}$ alkyl-carbonyloxy (e.g., acetoxy, propionyloxy, etc.), a $C_{6-14}$ aryl-carbonyloxy (e.g., benzoyloxy, naphthylcarbonyloxy, etc.), a $C_{1-6}$ alkoxy-carbonyloxy (e.g., methoxycarbonyloxy, ethoxycarbonyloxy, propoxycarbonyloxy, butoxycarbonyloxy, etc.), a mono-$C_{1-6}$ alkyl-carbamoyloxy (e.g., methylcarbamoyloxy, ethylcarbamoyloxy, etc.), a di-$C_{1-6}$ alkyl-carbamoyloxy (e.g., dimethylcarbamoyloxy, diethylcarbamoyloxy, etc.), a $C_{6-14}$ aryl-carbamoyloxy (e.g., phenylcarbamoyloxy, naphthylcarbamoyloxy, etc.), nicotinoyloxy, a 5- to 7-membered saturated cyclic amino (e.g., pyrrolidin-1-yl, piperidino, piperazin-1-yl, morpholino, thiomorpholino, tetrahydroazepin-1-yl, etc.), a 5- to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, etc.), sulfo, etc.

The "hydrocarbon group" may have, e.g., 1 to 5, preferably 1 to 3, of the substituents described above at substitutable positions. Where the number of substituents is 2 or more, the respective substituents may be the same or different.

The "heterocylic group" in the "optionally substituted heterocylic group," which is represented by $R^8$ or $R^{10}$, includes monovalent groups formed by removing one optional hydrogen atom from a 5- to 14-membered (monocyclic, dicyclic or tricyclic) hetero-ring containing, e.g., 1 or 2 members and 1 to 4 hetero atoms selected from nitrogen atom, sulfur atom and oxygen atom, in addition to carbon atoms, preferably (i) a 5- to 14-membered (preferably 5- to 10-membered) aromatic hetero-ring, (ii) a 5- to 10-membered non-aromatic hetero-ring or (iii) a 7- to 10-membered bridged hetero-ring; etc.

Examples of the "5- to 14-membered (preferably 5- to 10-membered) aromatic hetero-ring" include aromatic hetero-rings such as thiophene, benzo[b]thiophene, benzo[b]furan, benzimidazole, benzoxazole, benzothiazole, benzisothiazole, naphtho[2,3-b]thiophene, furan, pyrrole, imidazole, pyrazole, pyridine, pyrazine, pyrimidine, pyridazine, indole, isoindole, 1H-indazole, purine, 4H-quinolidine, isoquinoline, quinoline, phthalazine, naphthylidine, quinoxaline, quinazoline, cinnoline, carbazole, β-carboline, phenanthridine, acridine, phenazine, thiazole, isothiazole, phenothiazine, isoxazole, furazan, phenoxazine, etc.; or a ring formed by fusing these rings (preferably a mono-ring) with one or more (preferably 1 or 2) aromatic rings (e.g., a benzene ring, etc.), and the like.

Examples of the "5- to 10-membered non-aromatic hetero-ring" described above include pyrrolidine, imidazoline, pyrazolidine, pyrazoline, piperidine, piperazine, morpholine, thiomorpholine, dioxazole, oxadiazoline, thiadiazoline, triazoline, thiadiazole, dithiazole, etc.

Examples of the "7- to 10-membered bridged hetero-ring" include quinuclidine, 7-azabicyclo[2.2.1]heptane, etc.

The "heterocylic group" is preferably a 5- to 14-membered (preferably 5- to 10-membered) (and monocyclic or bicyclic) heterocylic group containing, in addition to carbon atoms, 1 or 2 members selected from nitrogen atom, sulfur atom and oxygen atom, preferably 1 to 4 hetero atoms. Specific examples include aromatic heterocyclic groups such as 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pyrazinyl, 2-pyrimidinyl, 4-pyrimidinyl, 3-pyrrolyl, 2-imidazolyl, 3-pyridazinyl, 3-isothiazolyl, 3-isoxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, etc.; non-aromatic heterocyclic groups such as 1-pyrrolidinyl, 2-pyrrolidinyl, 3-pyrrolidinyl, 2-imidazolinyl, 4-imidazolinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino, etc.

Among them, more preferred are 5- or 6-membered heterocylic groups containing, in addition to carbon atoms, e.g., 1 to 3 hetero atoms selected from nitrogen atom, sulfur atom and oxygen atom; etc. Specific examples are 2-thienyl, 3-thienyl, 2-pyridyl, 3-pyridyl, 4-pyridyl, 2-furyl, 3-furyl, pyrazinyl, 2-pyrimidinyl, 3-pyrrolyl, 3-pyridazinyl, 3-isothiazolyl, 3-isoxazolyl, 1-pyrrolidinyl, 2-pyrrolidinyl, 3-pyrrolidinyl, 2-imidazolinyl, 4-imidazolinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino, etc.

Examples of the "substituent(s)" in the "optionally substituted heterocyclic group" are the same substituents, etc., as given for the "substituent(s)" in the "hydrocarbon group which may optionally have a substituent(s)," which is represented by $R^8$ or $R^{10}$ described above.

The "heterocyclic group" may have, e.g., 1 to 5, preferably 1 to 3, of the substituents described above at substitutable positions. Where the number of substituents is 2 or more, the respective substituents may be the same or different.

Examples of the "$C_{1-6}$ alkyl" represented by $R^9$ include a $C_{1-6}$ alkyl such as methyl, ethyl, propyl, isopropyl, butyl, isobutyl, sec-butyl, tert-butyl, pentyl, hexyl, etc.

The "alkyl" in the "optionally substituted alkyl" shown by $R^6$ includes, for example, a $C_{1-30}$ alkyl (e.g., methyl, ethyl, propyl, propyl, butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl, triacontyl, etc.), and the like; preferably a $C_{1-6}$ alkyl, etc.

The "substituent(s)" in the "optionally substituted alkyl" shown by $R^6$ includes, for example, hydroxy, carboxy, amino, an alkylammonio (e.g., trimethylammonio, etc.) and the like, in 1 to 30 substituents.

The "cycloalkyl" in the "optionally substituted cycloalkyl" shown by $R^6$ includes, for example, a $C_{3-6}$ cycloalkyl (e.g., cyclopropyl, cyclobutyl, cyclopentyl, cyclohexyl, etc.), and the like.

The "substituent(s)" in the "optionally substituted cycloalkyl" shown by $R^6$ includes, for example, hydroxy, carboxy, amino, an alkylammonio (e.g., trimethylammonio, etc.), and the like, which may optionally have phosphono, in 1 to 30 substituents.

Preferred examples of $R^6$ are cases in which compounds represented by $R^6$—OH, for example, an alcohol (e.g., a $C_{1-6}$ alcohol such as ethanol, etc.), a polyvalent alcohol (e.g., a trivalent alcohol such as glycerol, etc.), a polyvalent alcohol-phosphoric acid adduct (e.g., glycerol-3-phosphate, etc.), an aminoalcohol (e.g., a $C_{1-6}$ alcoholamine such as ethanolamine, etc.), an alkylammonioalcohol (e.g., choline, etc.), an amino acid having hydroxy (e.g., serine, threonine, homoserine, 3-hydroxyproline, 4-hydroxyproline, hydroxylysine, tyrosine, etc.; preferably serine), a sugar alcohol (e.g., inositol, etc.), a sugar alcohol phosphoric acid adduct (e.g., inositol monophosphate, inositol diphosphate, inositol triphosphate, etc.), a monosaccharide (e.g.,: glucose, etc.), a monosaccharide phosphoric acid adduct (e.g., glucose 6-phosphate, glucose 1-phosphate, etc.), and the like, are formed.

Among them, preferred examples are amino acids having hydroxy, etc. In particular, L-form is preferred, most preferably, L-serine, etc.

Each of $R^1$ and $R^2$ is preferably a hydrogen atom, an alkyl (e.g., a $C_{14-18}$ alkyl, etc.), an alkenyl (e.g., a $C_{2-3}$ alkenyl, etc.), an acyl (e.g., a $C_{1-30}$ alkyl-carbonyl, a $C_{2-30}$ alkenyl-carbonyl, etc.), and the like. More preferred are an acyl such as a $C_{1-30}$ alkyl-carbonyl, a $C_{2-30}$ alkenyl-carbonyl, etc.

$R^3$ is preferably Group (III).

$R^6$ is preferably (a) a hydrogen atom or (b) an alkyl or cycloalkyl, which may optionally have a substituent(s) selected from hydroxy, carboxy, amino and an alkylammonio, respectively. Specific examples are a $C_{1-6}$ alkyl, dihydroxypropyl, aminoethyl, trimethylammonioethyl, 2-amino-2-carboxyethyl, hexahydroxycyclohexyl, etc.

For m, 1 is preferred.

In Compound (I), the following compounds and the like are preferably used. Ether phospholipids such as:

(1a) platelet activating factor [Compound (I) wherein $R^1$ is a $C_{1-6}$ alkyl (hexadecyl) and/or a $C_{1-8}$ alkyl (octadecyl), $R^2$ is acetyl, $R^3$ is Group (III), $R^6$ is trimethylammonioethyl, and m is 1];

(1b) lyso-platelet activating factor [Compound (I) wherein $R^1$ is hexadecyl and/or octadecyl, $R^2$ is a hydrogen atom, $R^3$ is Group (III), $R^6$ is trimethylammonioethyl and m is 1];

(1c) plasmalogens [Compound (I) wherein $R^1$ is a 1-alkenyl, $R^2$ is a $C_{1-29}$ alkyl-carbonyl or a $C_{2-29}$ alkenyl-carbonyl (having 1 to 5 double bonds), $R^3$ is Group (III), $R^6$ is trimethylammonioethyl, aminoethyl or 2-amino-2-carboxyethyl and m is 1];

(1d) lyso-plasmalogens [Compound (D wherein $R^1$ is a 1-alkenyl, $R^2$ is hydrogen atom, $R^3$ is Group (III), $R^6$ is trimethylammonioethyl, aminoethyl or 2-amino-2-carboxyethyl, and m is 1], etc.

Glycerophospholipids such as:

(2a) phosphatidic acids [Compound (I) wherein $R^1$ is a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^2$ is a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^3$ is Group (III), $R^6$ is a hydrogen atom, and m is 1];

(2b) lysophosphatidic acids [Compound (I) wherein $R^1$ is a hydrogen atom, a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^2$ is a hydrogen atom, a $C_{13-23}$ alkyl-carbonyl or a $C_{13-23}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^3$ is Group (III), $R^6$ is a hydrogen atom, and m is 1 (provided that when $R^1$ is a hydrogen atom, $R^2$ is other than a hydrogen atom)], (2c) phosphatidylcholines [Compound (I) wherein $R^1$ is a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^2$ is a $C_{13-23}$ alkyl-carbonyl or a $C_{13-23}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^3$ is Group (III), $R^6$ is trimethylammonioethyl, and m is 1];

(2d) lysophosphatidylcholines [Compound (I) wherein $R^1$ is a hydrogen atom, a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^2$ is a hydrogen atom, a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^3$ is Group (III), $R^6$ is trimethylammonioethyl, and m is 1 (provided that when $R^1$ is a hydrogen atom, $R^2$ is other than a hydrogen atom)];

(2e) phosphatidylethanolamines [Compound (I) wherein $R^1$ is a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^2$ is a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^3$ is Group (III), $R^6$ is aminoethyl, and m is 1];

(2f) lysophosphatidylethanolamines [Compound (I) wherein $R^1$ is a hydrogen atom, a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^2$ is a hydrogen atom, a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^3$ is Group (III), $R^6$ is aminoethyl, and m is 1 (provided that when $R^1$ is a hydrogen atom, $R^2$ is other than a hydrogen atom)];

(2g) phosphatidylserines [Compound (I) wherein $R^1$ is a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^2$ is a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^3$ is Group (III), $R^6$ is 2-amino-2-carboxyethyl, and m is 1];

(2h) lysophosphatidylserines [Compound (I) wherein $R^1$ is a hydrogen atom, a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^2$ is a hydrogen atom, a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^3$ is Group (III), $R^6$ is 2-amino-2-carboxyethyl, and m is 1 (provided that when $R^1$ is a hydrogen atom, $R^2$ is other than a hydrogen atom)];

(2i) phosphatidylinositols [Compound (I) wherein $R^1$ is a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^2$ is a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^3$ is Group (III), $R^6$ is hexahydroxycyclohexyl, and m is 1];

(2j) lysophosphatidylinositols [Compound (I) wherein $R^1$ is a hydrogen atom, a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^2$ is a hydrogen atom, a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^3$ is Group (III), $R^6$ is hexahydroxycyclohexyl, and m is 1 (provided that when $R^1$ is a hydrogen atom, $R^2$ is other than a hydrogen atom)], and the like.

Among others, preferred compounds include:

(i) phosphatidylserines [Compound (I) wherein $R^1$ is decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl or octacosanoyl, $R^2$ is decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl or octacosanoyl, $R^3$ is Group (III), $R^6$ is 2-amino-2-carboxyethyl, and m is 1];

(ii) lysophosphatidylserines [Compound (I) wherein $R^1$ is decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl or octacosanoyl, $R^2$ is decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl or octacosanoyl, $R^3$ is Group (III), $R^6$ is 2-amino-2-carboxyethyl, and m is 1], and the like.

Preferred are the compounds represented by the formula below, etc.

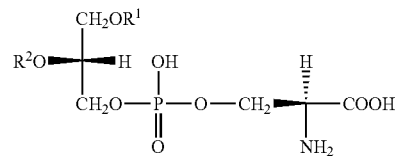

[wherein each symbol has the same significance as defined above].

Herein, $R^1$ and $R^2$ are preferably a hydrogen atom, an alkyl (e.g., a $C_{14-18}$ alkyl, etc.), an alkenyl (e.g., a $C_{2-3}$ alkenyl, etc.), or an acyl (e.g., a $C_{1-30}$ alkyl-carbonyl, a $C_{2-30}$ alkenyl-carbonyl, etc.), and the like.

$R^1$ is preferably a $C_{1-30}$ alkyl-carbonyl, etc. $R^2$ is preferably a hydrogen atom. Preferred combination of $R^1$ and $R^2$ includes the cases wherein $R^1$ is a hydrogen atom and $R^2$ is preferably a $C_{1-30}$ alkyl-carbonyl, etc.

Specific examples include 1-stearoyl-sn-glycero-3-phospho-L-serine, 1-palmitoyl-sn-glycero-3-phospho-L-serine, or 1-oleoyl-sn-glycero-3-phospho-L-serine, 2-arachidonyl-sn-glycero-3-phospho-L-serine, 2-linoleyl-sn-glycero-3-phospho-L-serine, etc.

As the sphingolipids, sphingophospholipids and phosphono-sphingolipids, there are, for example, Compound (II) and the like.

Compound (II) is preferably the compound represented by the formula below, or their salts:

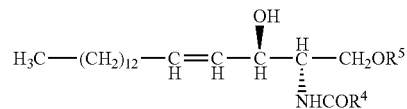

[wherein each symbol has the same significance as defined above].

In the formula above, the "optionally substituted hydrocarbon group" represented by $R^4$ is the same as those given for the aforesaid "optionally substituted hydrocarbon group" represented by $R^1$, $R^2$ or $R^3$.

The "acyl" shown by $R^4$ is the same as the aforesaid "acyl" represented by $R^1$, $R^2$ or $R^3$.

The "optionally substituted hydrocarbon group" represented by $R^5$ is the same as those given for the aforesaid "hydrocarbon group which may optionally have a substituent(s)" represented by $R^1$, $R^2$ or $R^3$.

The "acyl" shown by $R^5$ is the same as the aforesaid "acyl" represented by $R^1$, $R^2$ or $R^3$.

The "optionally substituted alkyl" and the "optionally substituted cycloalkyl" represented by $R^7$ are those given for the aforesaid "optionally substituted alkyl" and the "optionally substituted cycloalkyl" represented by $R^6$, respectively.

$R^4$ is preferably a hydrogen atom, an acyl (e.g., a $C_{1-30}$ alkyl-carbonyl, a $C_{2-30}$ alkenyl-carbonyl, etc.), and the like.

$R^5$ is preferably a hydrogen atom or Group (IV), etc.

$R^7$ is preferably an alkyl, etc., which may optionally have amino.

For n, 1 is preferred.

In Compound (II), the following compounds, etc. are preferably used.

Sphingolipids such as:

(3a) sphingosines [Compound (II) wherein $R^4$ is a hydrogen atom, $R^5$ is hydrogen], (3b) ceramides [Compound (II) wherein $R^4$ is a $C_{2-24}$ alkyl-carbonyl or a $C_{2-24}$ alkenyl-carbonyl (having 1 to 5 double bonds), and $R^5$ is a hydrogen atom], etc.;

(4a) sphingomyelins [Compound (IV) wherein $R^4$ is a $C_{2-24}$ alkyl-carbonyl or a $C_{2-24}$ alkenyl-carbonyl (having 1 to 5 double bonds), $R^5$ is Group (IV), $R^7$ is trimethylammonioethyl, and n is 1];

(4b) sphingosyl 1-phosphoric acid [Compound (II) wherein $R^4$ is a hydrogen atom, $R^5$ is Group (IV), $R^7$ is a hydrogen atom, and n is 1];

(4c) sphingosylphosphorylcholines [Compound (II) wherein $R^4$ is a hydrogen atom, $R^5$ is Group (IV), $R^7$ is trimethylammonioethyl, and n is 1], etc.

The compounds represented by formula (I), the compounds represented by formula (II) and salts thereof, which are labeled, are also included within the ligand of the present invention.

The labeling agent includes radioisotopes (e.g., [$^3$H], [$^{125}$I], [$^{14}$C], [$^{32}$P], [$^{33}$P], [$^{35}$S], etc.), fluorescent substances (e.g., fluorescein, etc.), luminescent substances (e.g., luminol, etc.), enzymes (e.g., a peroxidase, etc.), a lanthanide, etc. Among others, radioisotopes are preferred, with particular preference of tritium.

The labeled ligand is preferably the compound represented by formula (I) or salts thereof, which are labeled with radioisotopes, more preferably glycerophospholipids labeled with a radioisotope, much more preferably lysophosphatidylserine or phosphatidylserine labeled with a radioisotope (preferably tritium), and much more preferably lysophosphatidylserine labeled with tritium, etc.

Specific examples of the tritium-labeled lysophosphatidylserine include 1-[9,10-$^3$H$_2$]-stearoyl-sn-glycero-3-phospho-L-serine represented by the formula below, etc.

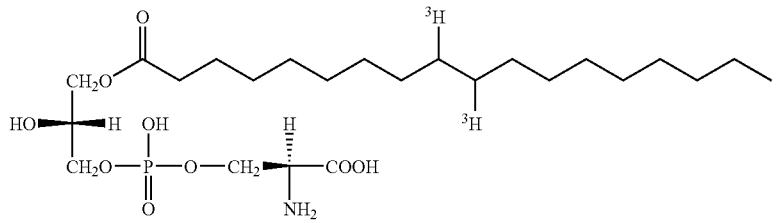

Preferably, the labeled ligand is 1-[9(S), 10(R)-3H2]-stearoyl-sn-glycero-3-phospho-L-serine shown by the formula below:

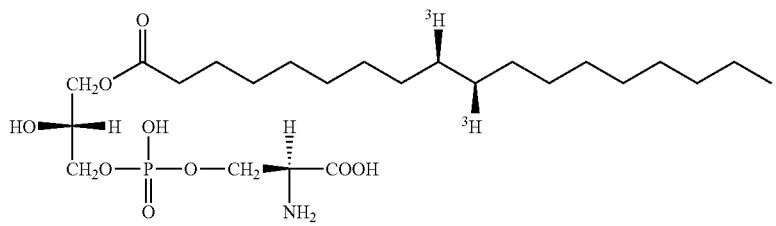

or 1-[9(R),10(S)-3H$_2$]-stearoyl-sn-glycero-3-phospho-L-serine shown by the formula below, etc.

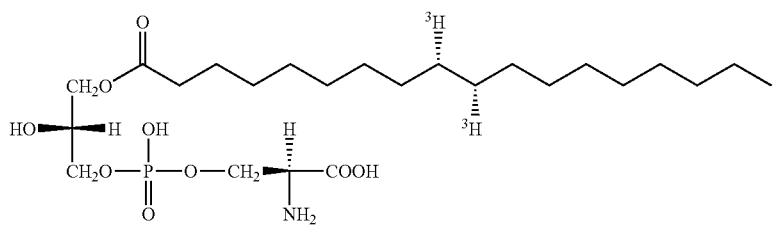

As salts of the compounds represented by formula (I) and salts of the compounds represented by formula, (II), there are, for example, metal salts, ammonium salts, salts with organic bases, salts with inorganic acids, salts with organic acids, salts with basic or acidic amino acids, etc. Preferred examples of the metal salts include alkali metal salts such as sodium salts, potassium salts, etc.; alkaline earth meal salts such as calcium salts, magnesium salts, barium salts, etc.; aluminum salts, etc. Preferred examples of the salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc. Preferred examples of the salts with inorganic acids include salts with hydrochloric acid, hydrobromic acid, nitric acid, sulfuric acid, phosphoric acid, etc. Preferred examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. Preferred examples of the salts with basic amino acids include salts with arginine, lysine, ornithine, etc., and preferred examples of the salts with acidic amino acids include salts with aspartic acid, glutamic acid, etc.

Of these, pharmacologically acceptable salts are preferred. For example, where the compounds contain acidic functional groups therein, examples include inorganic salts such as alkali metal salts (e.g., sodium salts, potassium salts, etc.), alkaline earth metal salts (e.g., calcium salts, magnesium salts, barium salts, etc.), ammonium salts, etc., and when the compounds contain basic functional groups therein, examples include salts with inorganic acids such as hydrobromic acid, nitric acid, sulfuric acid, phosphoric acid, etc., salts with organic acids such as acetic acid, phthalic acid, fumaric acid, oxalic acid, tartaric acid, maleic acid, citric acid, succinic acid, methanesulfonic acid, p-toluenesulfonic acid, etc.

The receptor of the present invention and the partial peptide of the present invention can be manufactured from the aforesaid human or warm-blooded animal cells or tissues by publicly known methods for purification of polypeptides, or can also be manufactured by culturing transformants transformed by DNAs encoding the polypeptides. In addition, they can also be manufactured by modifications of peptide synthesis. For example, the receptor and partial peptide can also be manufactured by the methods described in, e.g., Genomics, 56, 12-21, 1999, Biochim. Biophys. Acta, 1446, 57-70, 1999, etc., or by modifications of these methods.

Where the receptor and partial peptide of the present invention are manufactured from human or mammalian tissues or cells, human or mammalian tissues or cells are homogenized, then extracted with an acid or the like, and the extract is isolated and purified by a combination of chromatography techniques such as reverse phase chromatography, ion exchange chromatography, and the like.

To synthesize the receptor of the present invention or partial peptides or salts thereof, commercially available resins that are used for polypeptide synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenylhydroxymethyl)phenoxy resin, 4-(2',4'-dimethoxyphenyl-Fmoc-aminoethyl)phenoxy resin, etc. Using these resins, amino acids in which α-amino groups and functional groups on the side chains are appropriately protected are condensed on the resin in the order of the sequence of the objective polypeptide according to various condensation methods publicly known in the art. At the end of the reaction, the polypeptide is cut out from the resin and at the same time, the protecting groups are removed. Then, intramolecular disulfide bond-forming reaction is performed in a highly diluted solution to obtain the objective polypeptide, receptor, partial peptide or its amides.

For condensation of the protected amino acids described above, a variety of activation reagents for polypeptide synthesis may be used, and carbodiimides are particularly preferable. Examples of such carbodiimides include DCC, N,N'-diisopropylcarbodiimide, N-ethyl-N'-(3-dimethylaminoprolyl)carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be chosen from solvents known to be usable for polypeptide condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to polypeptide binding reactions and is usually selected in the range of approximately −20° C. to 50° C. The activated amino acid derivatives are used generally in an excess of 1.5 to 4 times. The condensation is examined by a test using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole.

Examples of the protecting groups used to protect the amino groups of the starting compounds include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower ($C_{1-6}$) alkanoyl group, such as acetyl group, an aroyl group such as benzoyl group, and a group derived from carbonic acid such as benzyloxycarbonyl group, ethoxycarbonyl group, etc. Examples of a group appropriately used for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br-Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups used in the starting compounds include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)], etc. As the activated amino acids, in which the amino groups are activated in the starting material, for example, the corresponding phosphoric amides are employed.

To eliminate (split off) the protecting groups, there are used catalytic reduction under hydrogen gas flow in the presence of a catalyst such as Pd-black, Pd-carbon, etc.; an acid treatment with anhydrous hydrogen fluoride, methanesulfonic acid, trifluoromethane-sulfonic acid or trifluoroacetic acid, or a mixture solution of these acids; a treatment with a base such as diisopropylethylamine, triethylamine, piperidine, piperazine, etc.; and reduction with sodium in liquid ammonia. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol, 1,2-ethanedithiol, etc. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol, 1,4-butanedithiol, etc. as well as by a treatment with an alkali such as a dilute sodium hydroxide solution, dilute ammonia, etc.

Protection of the functional groups that should not be involved in the reaction of the starting materials, protecting groups, elimination of the protecting groups, activation of functional groups involved in the reaction, or the like may be appropriately chosen from publicly known groups and publicly known means.

In another method for obtaining the receptor or partial peptide of the present invention, for example, the α-carboxyl group of the carboxy terminal amino acid is first protected by amidation; the peptide (polypeptide) chain is then extended from the amino group side to a desired length. Thereafter, a polypeptide in which only the protecting group of the N-terminal α-amino group in the peptide chain has been eliminated from the polypeptide and a polypeptide in which only the protecting group of the C-terminal carboxyl group has been eliminated are prepared. The two polypeptides are condensed in a mixture of the solvents described above. The details of the condensation reaction are the same as described above. After the protected polypeptide obtained by the condensation is purified, all the protecting groups are eliminated by the method described above to give the desired crude polypeptide. This crude polypeptide is purified by various known purification means. Lyophilization of the major fraction gives the amide of the desired receptor or its partial peptide.

To prepare the esterified receptor of the present invention or partial peptides or salts thereof, for example, the α-carboxyl group of the carboxy terminal amino acid is condensed with a desired alcohol to prepare the amino acid ester, which is followed by procedures similar to the preparation of the amidated receptor or partial peptide above to give the desired esterified receptor or partial peptide.

The receptor or partial peptide of the present invention can be prepared by publicly known methods for peptide synthesis, or the partial peptide of the receptor can be prepared by cleaving the receptor with an appropriate peptidase. For the methods for peptide synthesis, for example, either solid phase synthesis or liquid phase synthesis may be used. That is, the partial peptide or amino acids that can constitute the receptor or partial peptide of the present invention are condensed with the remaining part. Where the product contains protecting groups, these protecting groups are removed to give the desired peptide. Publicly known methods for condensation and elimination of the protecting groups are described in (i)-(v) below.

(i) M. Bodanszky & M. A. Ondetti: Peptide Synthesis, Interscience Publishers, New York (1966)
(ii) Schroeder & Luebke: The Peptide, Academic Press, New York (1965)
(iii) Nobuo Izumiya, et al.: Peptide Gosei-no-Kiso to Jikken (Basics and experiments of peptide synthesis), published by Maruzen Co. (1975)
(iv) Haruaki Yajima & Shunpei Sakakibara: Seikagaku Jikken Koza (Biochemical Experiment)$_1$, Tanpakushitsu no Kagaku (Chemistry of Proteins) IV, 205 (1977)
(v) Haruaki Yajima, ed.: Zoku Iyakuhin no Kaihatsu (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the receptor or partial peptide of the present invention. When the receptor or partial peptide obtained by the above methods is in a free form, the receptor or partial peptide can be converted into an appropriate salt by a publicly known method or its modification; conversely when the receptor or partial peptide is obtained in a salt form, it can be converted into a free form or other different salt form by a publicly known method or its modifications.

The polynucleotide encoding the receptor or partial peptide of the present invention may be any polynucleotide so long as it contains the base sequence encoding the receptor or partial peptide of the present invention described above. Preferably, the polynucleotide is a DNA. The DNA may also be any one of genomic DNA, genomic DNA library, cDNA derived from the cells or tissues described above, cDNA library derived from the cells or tissues described above and synthetic DNA.

The vector used for the library may be any of bacteriophage, plasmid, cosmid, phagemid and the like. In addition, the DNA can be amplified by reverse transcriptase polymerase chain reaction (hereinafter abbreviated as RT-PCR) with total RNA or mRNA fraction prepared from the above-described cells or tissues.

The DNA encoding the receptor of the present invention may be any one of, for example, a DNA containing the base sequence represented by SEQ ID NO: 2, or any DNA containing a base sequence hybridizable to the base sequence represented by SEQ ID NO: 2 under high stringent conditions and encoding the receptor which has the properties of substantially equivalent to those of the protein containing the amino acid sequence represented by SEQ ID NO: 1.

Examples of the DNA that is hybridizable to the base sequence represented by SEQ ID NO: 2 under high stringent conditions include DNAs having at least about 70% homology, preferably at least about 80% homology, more preferably at least about 90% homology, much more preferably at least about 95% homology, to the base sequence represented by SEQ ID NO: 2; and the like.

The hybridization can be carried out by publicly known methods or by a modification thereof, for example, according to the method described in Molecular Cloning, 2nd. (J. Sambrook et al., Cold Spring Harbor Lab. Press, 1989). A commercially available library can also be used according to the instructions of the attached manufacturer's protocol. The hybridization can be carried out preferably under high stringent conditions.

The high stringent conditions used herein are, for example, those in a sodium concentration at about 19 to 40 mM, preferably about 19 to 20 mM at a temperature of about 50 to 70° C., preferably about 60 to 65° C. In particular, hybridization conditions in a sodium concentration at about 19 mM at a temperature of about 65° C. are most preferred.

More specifically, as the DNA encoding the receptor containing the amino acid sequence represented by SEQ ID NO: 1, there may be employed a DNA containing the base sequence represented by SEQ ID NO: 2, etc., as the DNA encoding the receptor containing the amino acid sequence represented by SEQ ID NO: 19, there may be employed a DNA containing the base sequence represented by SEQ ID NO: 20, etc., as the DNA encoding the receptor containing the amino acid sequence represented by SEQ ID NO: 22, there may be employed a DNA containing the base sequence represented by SEQ ID NO: 23, etc., as the DNA encoding the receptor containing the amino acid sequence represented by SEQ ID NO: 31, there may be employed a DNA containing the base sequence represented by SEQ ID NO: 32, etc., as the DNA encoding the receptor containing the amino acid sequence represented by SEQ ID NO: 35, there may be employed a DNA containing the base sequence represented by SEQ ID NO: 36, etc.

As the DNA encoding the partial peptide of the present invention may be any DNA so long as it contains the base sequence encoding the partial peptide of the receptor of the present invention. The DNA may also be any one of genomic DNA, genomic DNA library, cDNA derived from the cells or tissues described above, cDNA library derived from the cells or tissues described above and synthetic DNA. Specifically, there are used a DNA having a part of the base sequence of a DNA having the base sequence represented by SEQ ID NO: 2 or a DNA having a part of the base sequence of a DNA having the base sequence represented by SEQ ID NO: 2 under high stringent conditions and containing a part of DNA encoding the receptor having the activities substantially equivalent to those of the protein comprising the amino acid sequence represented by SEQ ID NO: 1, and so on.

The DNA hybridizable to the base sequence represented by SEQ ID NO: 2 has the same significance as described above.

Methods for the hybridization and the high stringent conditions that can be used are the same as those described above.

The polynucleotide (e.g., DNA) encoding the receptor or partial peptide of the present invention may be labeled by methods public known. The labeled agents include radioisotopes, fluorescent substances (e.g., fluorescein, etc.), luminescent substances, enzymes, biotin, lanthanides, or the like.

For cloning of DNAs that completely encode the receptor or partial peptide of the present invention, the DNA can be either amplified by PCR using synthetic DNA primers containing a part of the base sequence of the receptor or partial peptide of the present invention, or the DNA inserted into an appropriate vector can be selected by hybridization with a labeled DNA fragment or synthetic DNA that encodes a part or entire region of the receptor or partial peptide of the present invention. The hybridization can be carried out, for example, according to the method described in Molecular Cloning, 2nd (J. Sambrook et al., Cold Spring Harbor Lab. Press, 1989). Where the hybridization is carried out using commercially available library, the procedures may be conducted in accordance with the protocol described in the attached instructions.

Conversion of the base sequence of DNA can be effected by publicly known methods such as the ODA-LA PCR method, the Gapped duplex method, the Kunkel method, etc., or its modification, using a publicly known kit, e.g., Mutan™-super Express Km (Takara Shuzo Co., Ltd.) or Mutan™-K (Takara Shuzo Co., Ltd.), etc.

The cloned DNA encoding the receptor can be used as it is, depending upon purpose or, if desired, after digestion with a restriction enzyme or after addition of a linker thereto. The DNA may contain ATG as a translation initiation codon at the 5' end thereof and TAA, TGA or TAG as a translation termination codon at the 3' end thereof. These translation initiation and termination codons may also be added by using an appropriate synthetic DNA adapter.

The expression vector for the receptor or partial peptide of the present invention can be manufactured, for example, by (a) excising the desired DNA fragment from the DNA encoding the receptor or partial peptide of the present invention, and then (b) ligating the DNA fragment with an appropriate expression vector downstream a promoter in the vector.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CM, pRc/RSV, pcDNA I/Neo, etc.

The promoter used in the present invention may be any promoter if it matches well with a host to be used for gene expression. In the case of using animal cells as the host, examples of the promoter include SRα promoter, SV40 promoter, LTR promoter, CMV promoter, HSV-TK promoter, etc.

Among them, it is preferred to use CMV (cytomegalovirus) promoter, SRα promoter, etc. Where the host is bacteria of the genus *Escherichia*, preferred examples of the promoter include trp promoter, lac promoter, recA promoter, $\lambda P_L$ promoter, lpp promoter, T7 promoter, etc. In the case of using bacteria of the genus *Bacillus* as the host, preferred example of the promoter are SPO1 promoter, SPO2 promoter, penP promoter, etc. When yeast is used as the host, preferred examples of the promoter are PHO5 promoter, PGK promoter, GAP promoter, ADH promoter, etc. When insect cells are used as the host, preferred examples of the promoter include polyhedrin prompter, P10 promoter, etc.

In addition to the foregoing examples, the expression vector may further optionally contain an enhancer, a splicing signal, a poly A addition signal, a selection marker, SV40 replication origin (hereinafter sometimes abbreviated as SV40ori), etc. Examples of the selection marker include dihydrofolate reductase (hereinafter sometimes abbreviated as dhfr) gene [methotrexate (MIX) resistance], ampicillin resistant gene (hereinafter sometimes abbreviated as $Amp^r$), neomycin resistant gene (hereinafter sometimes abbreviated as $Neo^r$, G418 resistance), etc. In particular, when dhfr gene is used as the selection marker using dhfr gene-deficient Chinese hamster cells, selection can also be made on a thymidine free medium.

If necessary, a signal sequence that matches with a host is added to the N-terminus of the receptor of the present invention. Examples of the signal sequence that can be used are PhoA signal sequence, OmpA signal sequence, etc. when bacteria of the genus *Escherichia* is used as the host; α-amylase signal sequence, subtilisin signal sequence, etc. when bacteria of the genus *Bacillus* is used as the host; MFα signal sequence, SUC2 signal sequence, etc. when yeast is used as the host; and insulin signal sequence, α-interferon signal sequence, antibody molecule signal sequence, etc. when animal cells are used as the host, respectively.

Using the vector containing the DNA encoding the receptor or partial peptide of the present invention thus constructed, transformants can be manufactured.

Examples of the host, which may be employed, are bacteria belonging to the genus *Escherichia*, bacteria belonging to the genus *Bacillus*, yeast, insect cells, insects, animal cells, etc.

Specific examples of the bacteria belonging to the genus *Escherichia* include *Escherichia coli* K12 DH1 [Proc. Natl. Acad. Sci. U.S.A., 60, 160 (1968)], JM103 [Nucleic Acids Research, 9, 309 (1981)], JA221 [Journal of Molecular Biology, 120, 517 (1978)], HB101 [Journal of Molecular Biology, 41, 459 (1969)], C600 [Genetics, 39, 440 (1954)], etc.

Examples of the bacteria belonging to the genus *Bacillus* include *Bacillus subtilis* MI114 [Gene, 24, 255 (1983)], 207-21 [Journal of Biochemistry, 95, 87 (1984)], etc.

Examples of yeast include *Saccharomyces cereviseae* AH22, AH22R⁻, NA87-11A, DKD-5D, 20B-12, *Schizosaccharomyces pombe* NCYC1913, NCYC2036, *Pichia pastoris* KM71, etc.

Examples of insect cells include, for the virus AcNPV, *Spodoptera frugiperda* cell (Sf cell), MG1 cell derived from mid-intestine of *Trichoplusia ni*, High Five™ cell derived from egg of *Trichoplusia ni*, cells derived from *Mamestra brassicae*, cells derived from Estigmena acrea, etc.; and for the virus BmNPV, *Bombyx mori* N cell (BmN cell), etc. is used. Examples of the Sf cell which can be used are Sf9 cell (ATCC CRL1711), Sf21 cell (both cells are described in Vaughn, J. L. et al., In Vivo, 13, 213-217 (1977)), etc.

As the insect, for example, a larva of *Bombyx mori* can be used [Maeda et al., Nature, 315, 592 (1985)].

Examples of animal cells include monkey cell COS-7, Vero, Chinese hamster cell CHO (hereinafter referred to as CHO cell), dhfr gene-deficient Chinese hamster cell CHO (hereinafter simply referred to as CHO (dhfr⁻) cell), mouse L cell, mouse AtT-20, mouse myeloma cell, mouse ATDC5 cell, rat GH3, human FL cell, etc.

Bacteria belonging to the genus *Escherichia* can be transformed, for example, by the method described in Proc. Natl. Acad. Sci. U.S.A., 69, 2110 (1972), Gene, 17, 107 (1982), etc.

Bacteria belonging to the genus *Bacillus* can be transformed, for example, by the method described in Molecular & General Genetics, 168, 111 (1979), etc.

Yeast can be transformed, for example, by the method described in Methods in Enzymology, 194, 182-187 (1991), Proc. Natl. Acad. Sci. U.S.A., 75, 1929 (1978), etc.

Insect cells or insects can be transformed, for example, according to the method described in Bio/Technology, 6, 47-55 (1988), etc.

Animal cells can be transformed, for example, according to the method described in Saibo Kogaku (Cell Engineering), extra issue 8, Shin Saibo Kogaku Jikken Protocol (New Cell Engineering Experimental Protocol), 263-267 (1995) (published by Shujunsha), or Virology 52, 456 (1973).

Thus, the transformants transformed with the expression vectors containing the DNAs encoding the receptor or partial peptide can be obtained.

Where the host is bacteria belonging to the genus *Escherichia* or the genus *Bacillus*, the transformant can be appropriately cultured in a liquid medium, which contains materials required for growth of the transformant such as carbon sources, nitrogen sources, inorganic materials, and the like. Examples of the carbon sources include glucose, dextrin, soluble starch, sucrose, etc.; examples of the nitrogen sources include inorganic or organic materials such as ammonium salts, nitrate salts, corn steep liquor, peptone, casein, meat extract, soybean cake, potato extract, etc.; and, examples of the inorganic materials are calcium chloride, sodium dihydrogenphosphate, magnesium chloride, etc. In addition, yeast extracts, vitamins, growth promoting factors etc. may also be added to the medium. Preferably, pH of the medium is adjusted to about 5 to about 8.

A preferred example of the medium for culturing the bacteria belonging to the genus *Escherichia* is M9 medium supplemented with glucose and Casamino acids [Miller, Journal of Experiments in Molecular Genetics, 431-433, Cold Spring Harbor Laboratory, New York, 1972]. If necessary, a chemical such as 3β-indolylacrylic acid can be added to the medium thereby to activate the promoter efficiently.

Where the bacteria belonging to the genus *Escherichia* are used as the host, the transformant is usually cultivated at about 15 to 43° C. for about 3 to 24 hours. If necessary, the culture may be aerated or agitated.

Where the bacteria belonging to the genus *Bacillus* are used as the host, the transformant is cultured generally at about 30 to 40° C. for about 6 to 24 hours. If necessary, the culture can be aerated or agitated.

Where yeast is used as the host, the transformant is cultivated, for example, in Burkholder's minimal medium [Bostian, K. L. et al., Proc. Natl. Acad. Sci. U.S.A., 77, 4505 (1980)] or in SD medium supplemented with 0.5% Casamino acids [Bitter, G. A. et al., Proc. Natl. Acad. Sci. U.S.A., 81, 5330 (1984)]. Preferably, pH of the medium is adjusted to about 5 to 8. In general, the transformant is cultivated at about 20 to 35° C. for about 24 to 72 hours. If necessary, the culture can be aerated or agitated.

Where insect cells or insects are used as the host, the transformant is cultivated in, for example, Grace's Insect Medium (Grace, T. C. C., Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary, the culture can be aerated or agitated.

Where animal cells are employed as the host, the transformant is cultured in, for example, MEM medium containing about 5 to 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30° C. to about 40° C. for about 15 to 60 hours and, if necessary, the culture can be aerated or agitated.

As described above, the receptor or partial peptide of the present invention can be produced in the transformant, in the cell membrane of the transformant, or outside of the transformant.

The receptor or partial peptide of the present invention can be separated and purified from the culture described above by the following procedures.

When the receptor or partial peptide of the present invention is extracted from the bacteria or cells, the bacteria or cell is collected after culturing by a publicly known method and suspended in an appropriate buffer. The bacteria or cell is then disrupted by publicly known methods such as ultrasonication, a treatment with lysozyme and/or freeze-thaw cycling, followed by centrifugation, filtration, etc to produce crude extract of the polypeptide. The buffer may contain a protein modifier such as urea or guanidine hydrochloride, or a surfactant such as Triton X-100™, etc. When the polypeptide is secreted in the culture broth, the supernatant can be separated, after completion of the cultivation, from the bacteria or cell to collect the supernatant by a publicly known method.

The receptor or partial peptide contained in the supernatant or the extract thus obtained can be purified by appropriately combining the publicly known methods for separation and purification. Such publicly known methods for separation and purification include a method utilizing difference in solubility such as salting out, solvent precipitation, etc.; a method mainly utilizing difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When the receptor or partial peptide thus obtained is in a free form, the receptor or partial peptide can be converted into the salt by publicly known methods or modifications thereof. On the other hand, when the receptor or partial peptide is obtained in the form of a salt, it can be converted into the free form or in the form of a different salt by publicly known methods or modifications thereof.

The receptor or partial peptide produced by the recombinant can be treated, prior to or after the purification, with an appropriate protein-modifying enzyme so that the receptor or partial peptide can be appropriately modified to partially remove the polypeptide. Examples of the protein-modifying enzyme include trypsin, chymotrypsin, arginyl endopeptidase, protein kinase, glycosidase and the like.

The ligand capable of specifically binding to the receptor of the present invention can be used as it is when commercially available, or can be extracted or manufactured by publicly known methods or its modifications.

The antibodies to the protein comprising the same or substantially the same amino acid sequence as the amino acid sequence represented by SEQ ID NO: 1, its partial peptide or a salt thereof (hereinafter sometimes collectively referred to as the antibody of the present invention) may be either polyclonal antibodies or monoclonal antibodies, as long as they are antibodies capable of recognizing antibodies against the receptor of the present invention. The antibodies against the receptor of the present invention include the antibodies that inactivate the signal transduction of the receptor, antibodies that activate the signal transduction of the receptor, etc.

The antibodies to the receptor of the present invention can be produced by a publicly known method of producing an antibody or antiserum, using the receptor of the present invention as an antigen.

[Preparation of Monoclonal Antibody]
(a) Preparation of Monoclonal Antibody-Producing Cells The receptor of the present invention is administered to warm-blooded animals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once every about 2 to about 6 weeks and about 2 to about 10 times in total. Examples of the applicable warm-blooded animals are monkeys, rabbits, dogs, guinea pigs, mice, rats, sheep, goats and fowl, with the use of mice and rats being preferred.

In the preparation of monoclonal antibody-producing cells, a warm-blooded animal, e.g., mouse, immunized with an antigen wherein the antibody titer is noted is selected, then spleen or lymph node is collected after 2 to 5 days from the final immunization and antibody-producing cells contained therein are fused with myeloma cells from homozoic or heterozoic animal to give monoclonal antibody-producing hybridomas. Measurement of the antibody titer in antisera may be carried out, for example, by reacting a labeled polypeptide, which will be described later, with the antiserum followed by assaying the binding activity of the labeling agent bound to the antibody. The fusion may be carried out, for example, by the known method by Koehler and Milstein [Nature, 256, 495, (1975)]. Examples of the fusion accelerator are polyethylene glycol (PEG), Sendai virus, etc., of which PEG is preferably employed.

Examples of the myeloma cells are those collected from warm-blooded animals such as NS-1, P3U1, SP2/0, AP-1, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by incubation at 20 to 40° C., preferably at 30 to 37° C. for 1 to 10 minutes, an efficient cell fusion can be carried out.

Various methods can be used for screening of monoclonal antibody-producing hybridomas. Examples of such methods include a method which comprises adding the supernatant of a hybridoma to a solid phase (e.g., a microplate) adsorbed with the polypeptide (protein) as an antigen directly or together with a carrier, adding an anti-immunoglobulin antibody (where mouse cells are used for the cell fusion, anti-mouse immunoglobulin antibody is used) labeled with a radioactive substance or an enzyme or Protein A and detecting the monoclonal antibody bound to the solid phase, and a method which comprises adding the supernatant of hybridoma to a solid phase adsorbed with an anti-immunoglobulin antibody or Protein A, adding the polypeptide labeled with a radioactive substance or an enzyme and detecting the monoclonal antibody bound to the solid phase, or the like.

The monoclonal antibody can be screened according to publicly known methods or their modifications. In general, the screening can be performed in a medium for animal cells supplemented with HAT (hypoxanthine, aminopterin and thymidine). Any screening and growth medium can be employed as far as the hybridoma can grow there. For example, RPMI 1640 medium containing 1 to 20%, preferably 10 to 20% fetal bovine serum, GIT medium (Wako Pure Chemical Industries, Ltd.) containing 1 to 10% fetal bovine serum, a serum free medium for cultivation of a hybridoma (SFM-101, Nissui Seiyaku Co., Ltd.) and the like, can be used for the screening and growth medium. The culture is carried out generally at 20 to 40° C., preferably at 37° C., for about 5 days to about 3 weeks, preferably 1 to 2 weeks, normally in 5% $CO_2$. The antibody titer of the culture supernatant of a hybridoma can be determined as in the assay for the antibody titer in antisera described above.

(b) Purification of Monoclonal Antibody

Separation and purification of a monoclonal antibody can be carried out by publicly known methods, such as separation and purification of immunoglobulins [for example, salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A or Protein G and dissociating the binding to obtain the antibody.]

[Preparation of Polyclonal Antibody]

The polyclonal antibody of the present invention can be manufactured by publicly known methods or modifications thereof. For example, a warm-blooded animal is immunized with an immunogen (polypeptide antigen) per se, or a complex of immunogen and a carrier protein is formed and the animal is immunized with the complex in a manner similar to the method described above for the manufacture of monoclonal antibodies. The product containing the antibody to the receptor of the present invention is collected from the immunized animal followed by separation and purification of the antibody.

In the complex of immunogen and carrier protein used to immunize a warm-blooded animal, the type of carrier protein and the mixing ratio of carrier to hapten may be any type and in any ratio, as long as the antibody is efficiently produced to the hapten immunized by crosslinking to the carrier. For example, bovine serum albumin, bovine thyroglobulin or hemocyanin is coupled to hapten in a carrier-to-hapten weight ratio of approximately 0.1 to 20, preferably about 1 to 5.

A variety of condensation agents can be used for the coupling of carrier to hapten. Glutaraldehyde, carbodiimide, maleimide activated ester and activated ester reagents containing thiol group or dithiopyridyl group are used for the coupling.

The condensation product is administered to warm-blooded animals either solely or together with carriers or diluents to the site that can produce the antibody by the administration. In order to potentiate the antibody productivity upon the administration, complete Freund's adjuvant or incomplete Freund's adjuvant may be administered. The administration is usually made once every about 2 to 6 weeks and about 3 to 10 times in total.

The polyclonal antibody can be collected from the blood, ascites, etc., preferably from the blood of warm-blooded animal immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as in the separation and purification of monoclonal antibodies described hereinabove.

The polynucleotide (e.g., DNA) containing a complementary or substantially complementary base sequence to the polynucleotide (e.g., DNA) or a part thereof encoding the protein containing the same or substantially the same amino acid sequences as the amino acid sequence represented by SEQ ID NO: 1 or SEQ ID NO: 19, as its partial peptide or as its salt can be any polynucleotide (antisense polynucleotide), so long as it contains a base sequence complementary or substantially complementary to the polynucleotide, or a part of the base sequence and capable of suppressing expression of the polynucleotide.

Specific examples of the polynucleotide include antisense DNAs (hereinafter these DNAs are sometimes simply referred to as the antisense DNA) having a base sequence complementary or substantially complementary to polynucleotides (e.g., DNAs) encoding the receptor of the present invention (hereinafter these DNAs are sometimes briefly referred to as the DNA of the present invention) or a part of the base sequence, and can be any antisense DNA, so long as it contains the complementary or substantially complementary base sequence to the DNA of the present invention, or a part of the base sequence and capable of suppressing expression of the DNA.

The base sequence substantially complementary to the DNA of the present invention may include, for example, a base sequence having at least about 70% homology, preferably at least about 80% homology, more preferably at least about 90% homology and most preferably at least about 95% homology, to the entire base sequence or to its partial base sequence (i.e., complementary strand to the DNA of the present invention), and the like. Especially in the entire base sequence of the complementary strand to the DNA of the present invention, preferred are an antisense DNA having at least about 70% homology, preferably at least about 80% homology, more preferably at least about 90% homology and most preferably at least about 95% homology, to the complementary strand of the base sequence which encodes the N-terminal region of the receptor of the present invention (e.g., the base sequence around the initiation codon). These antisense DNAs can be prepared using publicly known DNA synthesizer.

Specific examples include an antisense polynucleotide containing the entire or part of a base sequence complementary or substantially complementary to a base sequence of DNA containing the base sequence represented by SEQ ID NO: 2, preferably an antisense polynucleotide containing the entire or part of a base sequence complementary to a base sequence of DNA containing the base sequence represented by SEQ ID NO: 2, etc.

The antisense polynucleotide is generally constituted by bases of about 10 to about 40, preferably about 15 to about 30.

To prevent digestion with a hydrolase such as nuclease, etc., the phosphoric acid residue (phosphate) of each nucleotide that constitutes the antisense DNA may be substituted with chemically modified phosphoric acid residues, e.g., phosphorothioate, methyl phosphonate, phosphorodithionate, etc. These antisense polynucleotides may be synthesized using a publicly known DNA synthesizer, etc.

According to the present invention, the antisense polynucleotide capable of inhibiting the replication or expression of a gene for the receptor of the present invention (nucleic acid) can be designed and synthesized based on the base sequence information of cloned or identified protein-encoding DNA. Such a polynucleotide (nucleic acid) is hybridizable to RNA of a gene for the receptor of the present invention to inhibit the synthesis or function of said RNA or is capable of modulating and/or controlling the expression of a gene for the receptor of the present invention via interaction with RNA associated with the receptor of the present invention. Polynucleotides complementary to the selected sequences of RNA associated with the receptor of the present invention and polynucleotides specifically hybridizable to RNA associated with the receptor of the present invention are useful in modulating and/or controlling the in vivo and in vitro expression of the receptor gene of the present invention, and are useful for the treatment or diagnosis of diseases, etc. The term "corresponding" is used to mean homologous to or complementary to a particular sequence of the nucleotide including the gene, base sequence or nucleic acid. The term "corresponding" between nucleotides, base sequences or nucleic acids and peptides (proteins) usually refer to amino acids of a peptide (protein) under the order derived from the sequence of nucleotides (nucleic acids) or their complements. In the protein genes, the 5' end hairpin loop, 5' end 6-base-pair repeats, 5' end untranslated region, protein translation initiation codon, protein coding region, ORF translation termination codon, 3' end untranslated region, 3' end palindrome region, and 3' end hairpin loop, may be selected as preferred target regions, though any other region may be selected as a target in the protein genes.

The relationship between the targeted nucleic acids and the polynucleotides complementary to at least a part of the target region, specifically the relationship between the target nucleic acids and the polynucleotides hybridizable to the target region, can be denoted to be "antisense." Examples of the antisense polynucleotides include polynucleotides containing 2-deoxy-D-ribose, polynucleotides containing D-ribose, any other type of polynucleotides which are N-glycosides of a purine or pyrimidine base, or other polymers containing non-nucleotide backbones (e.g., commercially available protein nucleic acids and synthetic sequence-specific nucleic acid polymers) or other polymers containing nonstandard linkages (provided that the polymers contain nucleotides having such a configuration that allows base pairing or base stacking, as is found in DNA or RNA), etc. The antisense polynucleotides may be double-stranded DNA, single-stranded DNA, double-stranded RNA, single-stranded RNA or a DNA:RNA hybrid, and may further include unmodified polynucleotides (or unmodified oligonucleotides), those with publicly known types of modifications, for example, those with labels known in the art, those with caps, methylated polynucleotides, those with substitution of one or more naturally occurring nucleotides by their analogue, those with intramolecular modifications of nucleotides such as those with uncharged linkages (e.g., methyl phosphonates, phosphotriesters, phosphoramidates, carbamates, etc.) and those with charged linkages or sulfur-containing linkages (e.g., phosphorothioates, phosphorodithioates, etc.), those having side chain groups such as proteins (nucleases, nuclease inhibitors, toxins, antibodies, signal peptides, poly-L-lysine, etc.), saccharides (e.g., monosaccharides, etc.), those with intercalators (e.g., acridine, psoralen, etc.), those containing chelators (e.g., metals, radioactive metals, boron, oxidative metals, etc.), those containing alkylating agents, those with modified linkages (e.g., a anomeric nucleic acids, etc.), and the like. Herein the terms "nucleoside", "nucleotide" and "nucleic acid" are used to refer to moieties that contain not only the purine and pyrimidine bases, but also other heterocyclic bases, which have been modified. Such modifications may include methylated purines and pyrimidines, acylated purines and pyrimidines and other heterocyclic rings. Modified nucleotides and modified nucleotides also include modifications on the sugar moiety, wherein, for example, one or more hydroxyl groups may optionally be substituted with a halogen atom(s), an aliphatic group(s), etc., or may be converted into the corresponding functional groups such as ethers, amines, or the like.

The antisense polynucleotide (nucleic acid) of the present invention is RNA, DNA or a modified nucleic acid (RNA, DNA). Specific examples of the modified nucleic acid are, but not limited to, sulfur and thiophosphate derivatives of nucleic acids and those resistant to degradation of polynucleoside amides or oligonucleoside amides. The antisense nucleotide of the present invention can be modified preferably based on the following design, that is, by increasing the intracellular stability of the antisense nucleotide, enhancing the cell permeability of the antisense nucleotide, increasing the affinity of the nucleic acid to the targeted sense strand to a higher level, or minimizing the toxicity, if any, of the antisense nucleotide.

Many of such modifications are known in the art, as disclosed in J. Kawakami, et al., Pharm. Tech. Japan, Vol. 8, pp. 247, 1992; Vol. 8, pp. 395, 1992; S. T. Crooke, et al. ed., Antisense Research and Applications, CRC Press, 1993; etc.

The antisense polynucleotide of the present invention may contain altered or modified sugars, bases or linkages. The antisense polynucleotide may also be provided in a specialized form such as liposomes, microspheres, or may be applied to gene therapy, or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached to the nucleic acid at the 3' or 5' ends thereof and may also be attached thereto through a base, sugar, or intramolecular nucleoside linkage. Other moieties may be capping groups specifically placed at the 3' or 5' ends of the nucleic acid to prevent degradation by nucleases such as exonuclease, RNase, etc. Such capping groups include, but are not limited to, hydroxyl protecting groups known in the art, including glycols such as polyethylene glycol, tetraethylene glycol and the like.

The inhibitory action of the antisense nucleotide can be examined using the transformant of the present invention, the gene expression system of the present invention in vivo and in vitro, or the translation system for the receptor of the present invention in vivo and in vitro. The nucleic acid can be applied to cells by a variety of publicly known methods.

Hereinafter, (i) the receptor of the present invention, (ii) the polynucleotide encoding the receptor of the present invention (the polynucleotide of the present invention), (iii) the antibody to the receptor of the present invention (the antibody of the present invention) (iv) the antisense polynucleotide of the receptor of the present invention (e.g., the antisense DNA of the present invention), (v) the ligand capable of specifically binding to the receptor of the present invention (the ligand of the present invention), etc. are described in terms of their applications.

[1] Screening of Drug Candidate Compounds Having the IL-13 Production Inhibitory Action, Mast Cell Degranulation-Inhibitory Action, Eicosanoid Production Inhibitory Action, Mast Cell Growth Inhibitory Action, Etc., or Drug Candidate Compounds for Preventing/Treating Central Nervous Disorders, Etc.

The ligand of the present invention has the IL-13 production promoting activity in mast cells, mast cell degranulation-promoting action, eicosanoid (e.g., leukotriene, prostaglandin, etc.) production promoting action on mast cells, and the IL-10 production promoting action, IL-6 production inhibitory action and TNF-α production inhibitory action on microglial cells, and so on.

The compound or its salt which inhibits the function/activity (e.g., the IL-13 production promoting activity, degranulation-promoting action, eicosanoid production promoting action and growth promoting action on mast cells, and the IL-10 production promoting action, IL-6 production inhibitory action and TNF-α production inhibitory action on microglial cells) of the ligand of the present invention or the receptor of the present invention is useful as the IL-13 production inhibitor, mast cell degranulation-inhibitor, eicosanoid production inhibitor, mast cell growth inhibitor, IL-10 production inhibitor, IL-6 production promoter, TNF-α production promoter, etc. and can be used as an agent for preventing/treating, for example, immune disorders [e.g., inflammatory diseases (pituitary tumor, thyroiditis, peritonitis, Crohn's disease, ulcerative colitis, erythema nodosum, chronic rheumatoid arthritis, systemic lupus erythematosus, etc.), allergy (e.g., allergic conjunctivitis, allergic rhinitis, pollinosis, metal allergy, etc.), asthma, exudative otitis media, Meniere's disease, contact dermatitis, anaphylaxis, urticaria, myasthenia gravis, glomerulonephritis, Sjögren's syndrome, Basedow's disease, insulin resistant diabetes, atopic dermatitis, leukocyte abnormality, etc.], respiratory disorders [e.g., chronic obstructive pulmonary disease (e.g., chronic bronchitis, pulmonary emphysema), diffuse panbronchiolitis, cystic fibrosis, hypersensitivity penumonitis, idiopathic interstitial pneumonia, pulmonary fibrosis, etc.], urinary tract disorders (e.g., renal tubulointerstitial injuries (fibrosis), interstitial cystitis, allergic cystitis, etc.), circulatory diseases (e.g., arteriosclerosis, acute coronary syndrome, atherosclerotic aortic aneurysm, cardiac anaphylaxis, heart failure, myocardial infarction, angina pectoris, arrhythmia, deep venous thrombosis, restenosis after PTCA, etc.), ophthalmic disorders (e.g., pterygium, vernal catarrh, dry eyes, etc.), cancer (e.g., papillary thyroid carcinoma, non-small cell lung cancer, endometrial cancer, cervical cancer, gastric cancer, pancreatic cancer, lung cancer, renal cancer, liver cancer, ovarian cancer, prostate cancer, bladder cancer, breast cancer, colon cancer, rectal cancer, Kaposi's sarcoma, mastocytoma, etc.), digestive disorders [e.g., chronic liver disease, food allergy, allergic enteritis, milk protein-induced proctitis, peptic ulcer (e.g., gastric ulcer, duodenal ulcer, marginal ulcer, Zollinger-Ellison syndrome, etc.), gastritis, reflux esophagitis, NUD (Non Ulcer Dyspepsia), gastric MALT lymphoma, non-steroidal anti-inflammatory drug-induced ulcer, hyperacidity, postoperative stress-induced hyperacidity and ulcer, etc.], cerebral infarction, hyperlipemia, acute renal failure, diabetes mellitus, obesity, edema, granuloma, atopic myelitis, neurofibroma, nasal mucosa hypersensitivity, Hodgkin's disease, endometrial hyperplasia, central nervous disorders [e.g., neurodegenerative disease (e.g., Alzheimer's disease (familial Alzheimer's disease, juvenile Alzheimer's disease, sporadic Alzheimer's disease, etc.), Parkinson's disease, Down's syndrome, amyotrophic lateral sclerosis, prion disease (Creutzfeldt-Jakob disease), Huntington's chorea, diabetic neuropathy, multiple sclerosis, etc.), mental disorders (e.g., schizophrenia, depression, bipolar disorders, anxiety disorders, attention deficit hyperactivity disorders, panic disorders, etc.), cerebrovascular disorders (e.g., cerebral thrombosis, cerebral embolism, transient ischemic attack, etc.), etc.] and the like.

The "compound that inhibits the function/activity of the ligand of the present invention" includes, for example, a protein which binds to the ligand of the present invention, an antibody which specifically binds to the ligand of the present invention, etc. The "compound that inhibits the function/activity of the receptor of the present invention" includes, for example, an antagonist of the receptor of the present invention, a compound which inhibits the binding of the receptor of the present invention to the ligand of the present invention, an antibody which specifically binds to the receptor of the present invention, a compound which inhibits the expression of the receptor of the present invention (protein, gene) (e.g., double-stranded RNA comprising a part of an RNA encoding the receptor of the present invention [siRNA or shRNA to the receptor of the present invention], a ribozyme comprising a part of an RNA encoding the receptor of the present invention, an antisense DNA to a DNA encoding the receptor of the present invention), etc.

Preferred examples of the IL-13 production inhibitor include prophylactic/therapeutic agents for respiratory diseases, etc.

Preferred examples of the mast cell degranulation inhibitor include prophylactic/therapeutic agents for immune diseases, urologic diseases, circulatory diseases, etc.

Preferred examples of the eicosanoid production inhibitor include prophylactic/therapeutic agents for immune diseases, etc.

The compound or its salt that promotes the function/activity of the ligand of the present invention or the receptor of the present invention (e.g., an agonist of the receptor of the present invention) can promote the function/activity of the ligand or receptor in the central nervous system (e.g., the IL-10 production promoting activity, IL-6 production inhibitory activity and TNF-α production inhibitory activity on microglial cells, etc.), and is thus useful as, e.g., an IL-10 production promoter, an IL-6 production inhibitor, a TNF-α production inhibitor, etc. Therefore, the compound or its salt can be used as an agent for preventing/treating, for example, central nervous disorders [e.g., neurodegenerative disease (e.g., Alzheimer's disease (familial Alzheimer's disease, juvenile Alzheimer's disease, sporadic Alzheimer's disease, etc.), Parkinson's disease, Down's syndrome, amyotrophic lateral sclerosis, prion disease (Creutzfeldt-Jakob disease), Huntington's chorea, diabetic neuropathy, multiple sclerosis, etc.), mental disorders (e.g., schizophrenia, depression, bipolar disorder, anxiety disorder, attention deficit hyperactivity disorder, panic disorder, etc.), cerebrovascular disorder (e.g., cerebral thrombosis, cerebral embolism, transient ischemic attack, etc.), etc.].

By using the receptor of the present invention or by using the ligand-receptor assay system using the expression system of the receptor of the present invention in its recombinant form, compounds (e.g., peptides, proteins, non-peptide compounds, synthetic compounds, fermentation products, etc.) or salts thereof that change the binding properties of the receptor of the present invention to the ligand of the present invention can be efficiently screened.

The compounds or salts thereof include (i) compounds having the cell stimulating activities (for example, the activities that promote arachidonic acid release, acetylcholine release, intracellular $Ca^{2+}$ release, intracellular cAMP production, intracellular cAMP production suppression, intracellular cGMP production, inositol phosphate production, change in cell membrane potential, phosphorylation of intracellular proteins, activation of c-fos, pH reduction, GTPγS binding activity, activation of cAMP-dependent protein kinase, activation of cGMP-dependent protein kinase, activation of phospholipid-dependent protein kinase, activation of microtubule-associated protein kinase (MAP kinase) (e.g., ERK1/2 (p42/44 MAP kinase), p38 MAPK, JNK/SAPK, ERK5, etc.), etc.) mediated by the receptor of the present invention (agonists), (ii) compounds that do not have the cell-stimulating activities (antagonists), (iii) compounds that promote the binding properties of the receptor of the present invention to the ligand of the present invention, (iv) compounds that inhibit the binding properties of the receptor of the present invention to the ligand of the present invention, and the like.

Specifically, comparison is made between (i) when the ligand of the present invention is brought in contact with the receptor of the present invention and (ii) when the ligand of the present invention and a test compound are brought in contact with the receptor of the present invention. The comparison is made, e.g., by assaying, for example, the binding amount of the ligand of the present invention to the receptor of the present invention, the cell stimulating activities, or the like.

Specific examples of the screening method of the present invention include:

(a) a method of screening a compound or its salt that changes the binding properties of the ligand of the present invention to the receptor of the present invention, which comprises measuring the binding amounts of the ligand of the present invention to the receptor of the present invention when the ligand of the present invention is brought in contact with the receptor of the present invention and when the ligand of the present invention and a test compound are brought in contact with the receptor of the present invention; and comparing the binding amounts;

(b) a method of screening a compound or its salt that changes the binding amounts of the ligand of the present invention to the receptor of the present invention, which comprises assaying the binding amounts of the ligand of the present invention to a cell containing the receptor of the present invention or a membrane fraction of the cell, when the ligand of the present invention is brought in contact with the cell containing the receptor of the present invention or the membrane fraction of the cell and when the ligand of the present invention and a test compound are brought in contact with the cell or its cell membrane fraction, and comparing the binding amounts; and, (c) the screening method according to (b) described above, wherein the receptor of the present invention is the receptor of the present invention expressed on a cell membrane by culturing a transformant containing a DNA encoding the receptor of the present invention;

(d) the receptor-binding assay system such as the screening method described in (a) to (c) above, wherein the ligand of the present invention is a labeled ligand;

(e) a method of screening a compound or its salt that changes the binding properties of the ligand of the present invention to the receptor of the present invention, which comprises assaying the cell stimulating activities mediated by the receptor of the present invention, when the ligand of the present invention is brought in contact with the receptor of the present invention and when the ligand of the present invention and a test compound are brought in contact with the receptor of the present invention; and comparing the activities;

(f) a method of screening a compound or its salt that changes the binding properties of the ligand of the present invention to the receptor of the present invention, which comprises assaying the cell stimulating activities mediated by the receptor of the present invention, when the ligand of the present invention is brought in contact with a cell containing the receptor of the present invention or a membrane fraction of the cell, and when the ligand of the present invention and a test compound are brought in contact with the cell containing the receptor of the present invention or its cell membrane fraction; and comparing the activities; and, (g) the screening method according to (f) described above, where the receptor of the present invention is the receptor of the present invention expressed on a cell membrane by culturing a transformant containing a DNA encoding the receptor of the present invention; etc.

The screening method of the present invention is specifically described below.

As the receptor of the present invention, membrane fractions from human or warm-blooded animal organs are preferably employed. However, it is very difficult to obtain human-derived organs among others, and the receptor of the present invention, etc. expressed abundantly by use of recombinants are suitable for use in the screening.

To produce the receptor of the present invention, the aforesaid methods for producing the receptor of the present invention, etc. are applied.

When cells containing the receptor of the present invention or membrane fractions of these cells are employed in the screening methods of the present invention, these cells or membrane fractions may be prepared according to the procedures later described.

Where cells containing the receptor of the present invention are employed, the cells may be fixed using glutaraldehyde, formalin, etc. The fixation can be made by publicly known methods.

The cells containing the receptor of the present invention refer to host cells where the receptor of the present invention is expressed, and such host cells include *Escherichia coli, Bacillus subtilis*, yeast, insect cells, animal cells, etc. described above. The host cells can be prepared in a manner similar to the method described above.

The cell membrane fraction is used to mean a fraction abundant in cell membrane obtained by cell disruption and subsequent fractionation by publicly known methods. The cell disruption methods include cell squashing using a Potter-Elvehjem homogenizer, disruption using a Waring blender or Polytron (manufactured by Kinematica Inc.), disruption by ultrasonication, disruption by cell spraying through thin nozzles under an increased pressure using a French press, and the like. Cell membrane fractionation is effected mainly by fractionation using a centrifugal force, such as fractional centrifugation, density gradient centrifugation, etc. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in the receptor of the present invention expressed and membrane components such as cell-derived phospholipids, membrane proteins, etc.

The amount of the receptor of the present invention in the cells or cell membrane fractions containing the receptor of the present invention is preferably $10^3$ to $10^8$ molecules, more preferably $10^5$ to $10^7$ molecules, per cell. As the amount of expression increases, the ligand binding activity per unit of the membrane fraction (specific activity) increases so that not only the highly sensitive screening system can be constructed but also large quantities of samples can be assayed on the same lot.

To perform the screening methods such as the receptor-binding assay system, the cell stimulating assay system and the like, for example, a fraction of the receptor of the present invention and a labeled form of the ligand of the present invention (e.g., a labeled form of the ligand of the present invention), etc. are employed. For the fraction of the receptor of the present invention, a fraction from naturally occurring type of the receptor of the present invention or a fraction from recombinant type of the receptor of the present invention having an activity equivalent thereto, or the like, are desirable. Herein, the equivalent activity is used to mean an equivalent ligand binding activity, etc. As the labeled ligands, there may be used ligands labeled with, e.g., radioisotope (e.g., [$^3$H], [$^{125}$I], [$^{14}$C], [$^{32}$P], [$^{33}$P], [$^{35}$S], etc.), fluorescent substances (e.g., fluorescein, etc.), luminescent substances (e.g., luminol, etc.), enzymes (e.g., peroxidase, etc.), lanthanide, or the like.

Specifically, screening of the compound that changes the binding properties of the ligand of the present invention to the receptor of the present invention can be performed by the following procedures. First, a receptor preparation is prepared by suspending cells containing the receptor of the present invention or their membrane fractions in a buffer appropriate for screening. Any buffer can be used so long as it does not interfere with ligand-receptor binding, such buffer including a phosphate buffer, a Tris-HCl buffer, etc. having pH of 4 to 10 (desirably pH of 6 to 8). For the purpose of minimizing non-specific binding, a surfactant such as CHAPS, Tween-80™ (manufactured by Kao-Atlas Inc.), digitonin, deoxycholate, etc. may be added to the buffer. Further for the purpose of suppressing degradation of the receptor of the present invention by a protease, a protease inhibitor such as PMSF, leupeptin, E-64 (manufactured by Peptide Institute, Inc.), pepstatin, etc. may also be added. A given quantity (5,000 cpm to 500,000 cpm) of a labeled form of the ligand of the present invention is added to 0.01 ml to 10 ml of the receptor solution, and at the same time, $10^{-1}$ to $10^{-7}$ µM of a test compound is allowed to be co-present. To determine the amount of non-specific binding (NSB), a reaction tube containing a large excess of the ligand of the present invention in an unlabeled form is also provided. The reaction is carried out at 0° C. to 50° C., preferably about 4° C. to 37° C. for 20 minutes to 24 hours, preferably 30 minutes to 3 hours. After completion of the reaction, the reaction mixture is filtrated through glass fiber filter paper, etc. and washed with an appropriate volume of the same buffer. The residual radioactivity in the glass fiber filter paper is then measured by means of a liquid scintillation counter or a γ-counter. When the nonspecific binding (NSB) is subtracted from the count ($B_0$) when any antagonizing compound is absent and the thus obtained count ($B_0$-NSB) is made 100%, a test compound having the specific binding (B-NSB) of, e.g., 50% or less, can be selected as a candidate substance capable of competitive inhibition.

In addition, the compounds which bind to the receptor of the present invention can also be screened by utilizing the surface plasmon sensor technique.

Specifically, the receptor of the present invention is immobilized on the sensor chip surface of Biacore 3000 (Biacore, Inc.), and then the solution of a test compound in phosphate-buffered saline (PBS), etc. is applied onto the chip surface. By monitoring the changes on the surface plasmon, the test compound bound to the receptor of the present invention is screened. For example, the test compound, which gives the measurement data of 5 resonance units or more in the changes at the surface plasmon, is screened as a substance having the binding properties to the receptor of the present invention.

To perform the screening methods of the cell stimulating assay system described above, the cell-stimulating activities mediated by the receptor of the present invention (e.g., the activity that promotes or suppresses arachidonic acid release, acetylcholine release, intracellular $Ca^{2+}$ release, intracellular cAMP production, intracellular cAMP production suppression intracellular cGMP production, inositol phosphate production, change in cell membrane potential, phosphorylation of intracellular proteins, activation of c-fos, pH reduction, GTPγS binding activity, activation of cAMP-dependent protein kinase, activation of cGMP-dependent protein kinase, activation of phospholipid-dependent protein kinase, activation of microtubule-associated protein kinase (MAP kinase) (e.g., ERK1/2 (p42/44 MAP kinase), p38 MAPK, JNK/SAPK, ERK5, etc.), etc.) may be assayed by publicly known methods, or using assay kits commercially available. Specifically, the cells containing the receptor of the present invention are first cultured on a multi-well plate, etc. Prior to screening, the medium is replaced with a fresh medium or with an appropriate non-cytotoxic buffer, and a test compound or the like is added thereto, followed by culturing for a given period of time. Subsequently, the cells are extracted or the supernatant is recovered and the resulting product is quantified by the respective methods. Where it is difficult to detect the production of an indicator substance for the cell stimulating activities (e.g., arachidonic acid, etc.) due to a degrading enzyme contained in the cells, an inhibitor against such a degrading enzyme may be added prior to the assay. For detecting activities such as the cAMP production suppressing activity, the baseline production in the cells is increased by forskolin or the like and the suppressing effect on the increased baseline production can be detected.

To perform the screening by assaying the cell stimulating activities, cells in which an appropriate form of the receptor of the present invention is expressed are required. As the cells where the receptor of the present invention is expressed, an aforesaid cell line where the receptor of the present invention is expressed, etc. are desirable.

Examples of the test compound include peptides, proteins, antibodies, non-peptide compounds, synthetic compounds, fermentation products, cell extracts, plant extracts, animal tissue extracts, and the like.

In more detail, the screening methods of the cell stimulating assay system described above are described in (1) to (12) below.

(1) When the receptor-expressed cells are stimulated by the receptor agonist, G protein in the cells is activated and GTP binds thereto. This phenomenon is observed as well in a membrane fraction of the receptor-expression cells. Usually, GTP is hydrolyzed and changes to GDP; when GTPγS is previously added to the reaction solution, GTPγS binds to G protein as GTP does, but does not undergo hydrolysis so that the state bound to the G protein-containing cell membrane is maintained. When labeled GTPγS is used, the cell stimulating activities of the receptor agonist-expressed cell can be assayed by determining the labeled GTPγS remained on the cell membrane.

Utilizing this reaction, the compound that changes the binding properties of the ligand of the present invention to the receptor of the present invention can be screened by assaying the stimulating activities of the ligand of the present invention on the cells where the receptor of the present invention is expressed.

This method is carried out using the membrane fraction containing the receptor of the present invention. In this assay method, the substance showing the activity of promoting the binding of GTPγS to the membrane fraction containing the receptor of the present invention is an agonist.

Specifically, the compound that changes the binding properties of the ligand of the present invention to the receptor of the present invention can be screened by assaying the GTPγS binding promoting activities on the membrane fraction containing the receptor of the present invention in the presence of labeled GTPγS, when the ligand of the present invention is brought in contact with the membrane fraction containing the receptor of the present invention and when the ligand of the present invention and a test compound are brought in contact with the membrane fraction containing the receptor of the present invention; and comparing the activities.

In this method, the test compound showing the activity of suppressing the GTPγS binding promoting activity by the ligand of the present invention against the membrane fraction containing the receptor of the present invention can be selected as a candidate substance capable of competitive inhibition.

On the other hand, when a test compound alone is brought into contact with the cell membrane fraction of the receptor of the present invention, the agonist can be screened as well by assaying the GTPγS binding-promoting activities in the cell membrane fraction containing the receptor of the present invention.

A specific example of the screening method is described below.

The membrane fraction containing the receptor of the present invention, which is prepared by a modification of publicly known methods, is diluted with a buffer for membrane dilution (50 mM Tris, 5 mM $MgCl_2$, 150 mM NaCl, 1 µM GDP, 0.1% BSA, pH 7.4). A degree of dilution varies depending upon the amount of a receptor expressed. The dilution is dispensed by 0.2 ml each in Falcon 2053, to which the ligand of the present invention or the ligand of the present invention and a test compound is/are added, and $[^{35}S]GTP\gamma S$ is further added to the mixture in a final concentration of 200 pM. After maintaining at 25° C. for an hour, 1.5 ml of ice-cooled wash buffer (50 mM Tris, 5 mM $MgCl_2$, 150 mM NaCl, 0.1% BSA, 0.05% CHAPS, pH 7.4) is added to the mixture followed by filtration through a glass fiber filter paper GF/F. After keeping at 65° C. for 30 minutes, the mixture is dried and the radioactivity of $[^{35}S]$ GTPγS bound to the membrane traction remained on the filter paper is measured with a liquid scintillation counter. When the radioactivity in the experimental zone added with the ligand of the present invention alone is defined as 100% and the radioactivity in the experimental zone not added with the ligand of the present invention is defined as 0%, an effect of the test compound on the GTPγS binding promoting activity by the ligand of the present invention is worked out. The test compound showing the GTPγS binding promoting activity of, for example, 50% or less can be selected as a candidate compound capable of competitive inhibition.

(2) In the cells where the receptor of the present invention is expressed, the intracellular cAMP production is suppressed by stimulation of the ligand of the present invention. Utilizing this reaction, the compound that changes the binding properties of the ligand of the present invention to the receptor of the present invention can be screened by assaying the stimulating activities of the ligand of the present invention on the cells where the receptor of the present invention is expressed.

Specifically, the compound that changes the binding properties of the ligand of the present invention to the receptor of the present invention can be screened by assaying intracellular cAMP production suppressing activities on the cells in the presence of a substance capable of increasing the intracellular cAMP level, when the ligand of the present invention is brought in contact with the cells where the receptor of the present invention is expressed and when the ligand of the present invention and a test compound are brought in contact with the cells where the receptor of the present invention is expressed; and comparing the activities.

As the substance capable of increasing the intracellular cAMP level, there are employed, e.g., forskolin, calcitonin, etc.

The amount of cAMP produced in the cells where the receptor of the present invention is expressed can be assayed by the RIA system using an anti-cAMP antibody, whose antibody is obtained from immunized mouse, rat, rabbit, goat, bovine, etc., and $[^{125}I]$-labeled cAMP (both commercially available) or by the EIA system using an anti-cAMP antibody and labeled cAMP in combination. Quantification by the SPA (Scintillation Proximity Assay) method is also available, using beads, which contain scintillants bearing anti-cAMP antibodies immobilized using protein A or antibodies to IgG, etc. of animal used to produce the anti-cAMP antibodies, and $[^{125}I]$-labeled cAMP (the kit manufactured by Amersham Pharmacia Biotech, Inc. is used).

In this method, the test compound showing the activity of inhibiting the cAMP production suppressing activity by the ligand of the present invention against the cells wherein the receptor of the present invention is expressed can be selected as a candidate substance capable of competitive inhibition.

On the other hand, when a test compound alone is brought into contact with the cells where the receptor of the present invention is expressed, a compound showing an agonist activity can be screened by inspecting the cAMP production suppressing activity.

A specific example of the screening method is described below.

The cells where the receptor of the present invention is expressed (e.g., animal cells such as CHO cells, etc.) are plated on a 24-well plate in $5\times10^4$ cells/well followed by cultivation for 48 hours. The cells are washed with Hanks' balanced salt solution (pH 7.4) containing 0.2 mM 3-isobutyl-methylxanthine, 0.05% BSA and 20 mM HEPES (hereinafter simply referred to as a reaction buffer). Thereafter, 0.5 ml of the reaction buffer is added to the cells and the mixture is kept warm in the medium for 30 minutes. The reaction buffer is removed and 0.25 ml of a fresh reaction buffer is added to the cells. Then, 0.25 ml of a 2 µM forskolin-containing reaction buffer, in which 1 µM of the ligand of the present invention or 1 µM of the ligand of the present invention and a test compound is/are incorporated, is added to the cells, followed by reacting at 37° C. for 24 minutes. The reaction is terminated by adding 100 µl of 20% perchloric acid. The reaction mixture is then put on ice for an hour to extract intracellular cAMP. The amount of cAMP in the extract is measured using a cAMP EIA kit (Amersham Pharmacia Biotech). Taking the amount of cAMP produced by forskolin stimulation as 100% and the amount of cAMP inhibited by addition of 1 µM of the ligand of the present invention as 0%, an effect of the test compound on the cAMP production suppressing activity by the ligand of the present invention is calculated. The test compound that inhibits the activity of the ligand of the present invention to increase the cAMP producing activity, e.g., to 50% or more, can be selected as a candidate substance capable of competitive inhibition.

Further in the case of using the cells where the receptor of the present invention is expressed and which show the property of increasing the intracellular cAMP level through stimulation by the ligand of the present invention, the compound that changes the binding properties of the ligand of the present invention to the receptor of the present invention can be screened by assaying the intracellular cAMP production promoting activities on the cells, when the ligand of the present invention is brought in contact with the cells where the receptor of the present invention is expressed and when the ligand of the present invention and a test compound are brought in contact with the cells where the receptor of the present invention is expressed; and comparing the activities.

In this method, the test compound showing the activity of inhibiting the cAMP production promoting activity by the ligand of the present invention against the cells where the receptor of the present invention is expressed can be selected as a candidate substance capable of competitive inhibition.

On the other hand, when a test compound alone is brought into contact with the cell where the receptor of the present invention is expressed, a compound showing an agonist activity can be screened by monitoring the cAMP producing activity.

The cAMP production promoting activity is assayed by the method described above, through quantification of cAMP produced by adding the ligand of the present invention or the ligand of the present invention and a test compound to the cell where the receptor of the present invention is expressed, without adding forskolin in the screening method described above.

(3) The compound that changes the binding properties of the ligand of the present invention to the receptor of the present invention can be screened by assaying the stimulating activities of the ligand of the present invention on the cell where the receptor of the present invention is expressed, using a CRE-reporter gene vector.

A DNA containing CRE (cAMP response element) is inserted into a vector upstream the reporter gene to acquire CRE-reporter gene vector. In the CRE-reporter gene vector-transfected cells where the receptor of the present invention is expressed, stimulation accompanied by increased cAMP induces expression of the reporter gene mediated by CRE and subsequent production of the gene product (protein) of the reporter gene. That is, changes in the amount of cAMP in the CRE-reporter gene vector-transfected cells can be detected by assaying the enzyme activity of the reporter gene protein.

Specifically, the compound that changes the binding properties of the ligand of the present invention to the receptor of the present invention can be screened by assaying the enzyme activities of the reporter gene protein on the cells in the presence of a substance capable of increasing the intracellular cAMP level, when the ligand of the present invention is brought in contact with the CRE-reporter gene vector-transfected cells where the receptor of the present invention is expressed and when the ligand of the present invention and a test compound are brought in contact with the CRE-reporter gene vector-transfected cells where the receptor of the present invention is expressed; and comparing the activities.

As the substance capable of increasing the intracellular cAMP level, there are employed, e.g., forskolin, calcitonin, etc.

As the vector, there may be employed, e.g., PicaGene Basic Vector, PicaGene Enhancer Vector (Toyo Ink Mfg. Co., Ltd.), and the like. A CRE-containing DNA is inserted into the vector described above at the multicloning site upstream the reporter gene, e.g., luciferase gene, which is made a CRE-reporter gene vector.

In this method, a test compound which recovers the enzyme activity suppression of the reporter gene protein by the ligand of the present invention can be selected as a candidate substance capable of competitive inhibition.

On the other hand, the agonist can be screened as well by contacting a test compound alone with the cell where the receptor of the present invention is expressed and assaying the suppression of luminescence level increased by forskolin stimulation as in the ligand of the present invention.

Taking as an example in which luciferase is used as a reporter gene, a specific example of this screening method is described below.

The CRE-reporter gene (luciferase)-transfected cells where the receptor of the present invention is expressed are plated on a 24-well plate in $5 \times 10^3$ cells/well followed by cultivation for 48 hours. The cells are washed with Hanks' balanced salt solution (pH 7.4) containing 0.2 mM 3 isobutyl-methylxanthine, 0.05% BSA and 20 mM HEPES (hereinafter merely referred to as a reaction buffer). Thereafter, 0.5 ml of the reaction buffer is added to the cells and the mixture is kept warm in the medium for 30 minutes. The reaction buffer is removed and 0.25 ml of a fresh reaction buffer is added to the cells. Then, 1 μM of the ligand of the present invention or 1 μM of the ligand of the present invention and a test compound is/are added to 0.25 ml of the reaction buffer containing 2 μM forskolin, which is added to the cells. The reaction is then carried out at 37° C. for 24 minutes. The cells are dissolved in a cell lysis agent for PicaGene (Toyo Ink Mfg. Co., Ltd.) and a luminescent substrate (Toyo Ink Mfg. Co., Ltd.) is added to the lysate. Luminescence by luciferase is measured with a luminometer, a liquid scintillation counter or a top counter. The levels of luminescence by luciferase are measured when only the ligand of the present invention is added and when 1 μM of the ligand of the present invention and a test compound are added, and compared therebetween.

The ligand of the present invention suppresses the increase in luminescent level by luciferase, based on forskolin stimulation. The compound that recovers the suppression can be selected as a candidate substance capable of competitive inhibition.

As the reporter gene, there may be employed genes, e.g., alkaline phosphatase, chloramphenicol acetyltransferase, β-galactosidase, etc. The enzyme activities of these reporter gene proteins are assayed in accordance with methods publicly know, or using commercially available assay kits. The alkaline phosphatase activity can be assayed by using, e.g., Lumi-Phos 530 manufactured by Wako Pure Chemical Industries, Ltd.; the chloramphenicol acetyltransferase activity by using, e.g., FAST CAT chloramphenicol Acetyltransferase Assay Kit manufactured by Wako Pure Chemical Industries, Ltd.; and the β-galactosidase activity by using, e.g., Aurora Gal-XE manufactured by Wako Pure Chemical Industries, Ltd.

(4) The cells where the receptor of the present invention is expressed extracellularly release arachidonic acid metabolites by stimulation of the ligand of the present invention. Utilizing this reaction, the stimulating activities of the ligand of the present invention on the cell where the receptor of the present invention is expressed are assayed, whereby the compound that changes the binding properties of the ligand of the present invention to the receptor of the present invention can be screened.

Labeled arachidonic acid is previously taken up into the cell where the receptor of the present invention is expressed. Thus, the arachidonic acid metabolite releasing activity can be assayed by measuring the labeled arachidonic acid metabolite released at the outside of the cell.

Specifically, the compound that changes the binding properties of the ligand of the present invention to the receptor of the present invention can be screened by assaying arachidonic acid metabolite-releasing activities, when the ligand of the present invention is brought in contact with the labeled arachidonic acid-containing cells where the receptor of the present invention is expressed and when the ligand of the present invention and a test compound are brought in contact with the labeled arachidonic acid-containing cells where the receptor of the present invention is expressed; and comparing the activities.

In this method, the test compound that inhibits the arachidonic acid metabolite-releasing activity by the ligand of the present invention can be selected as a candidate substance capable of competitive inhibition.

Also, a test compound alone is brought into contact with the cell where the receptor of the present invention is expressed and the arachidonic acid metabolite-releasing activity in the cell where the receptor of the present invention is expressed is examined by publicly known methods. Thus, the compound showing the agonist activity can be screened as well.

A specific example of this screening method is described below.

The cells where the receptor of the present invention is expressed are plated on a 24-well plate in $5\times10^4$ cells/well. After cultivation for 24 hours, [$^3$H] arachidonic acid is added to the cells in 0.25 μCi/well. Sixteen hours later, the cells are washed with Hanks' balanced salt solution (pH 7.4) containing 0.05% BSA and 20 mM HEPES (hereinafter simply referred to as a reaction buffer). To each well is added 500 μl of the reaction buffer containing the ligand of the present invention in the final concentration of 10 μM, or the ligand of the present invention in the final concentration of 10 μM and a test compound. After incubation at 37° C. for 60 minutes, 400 μl of the reaction solution is charged in a scintillator and the amount of [$^3$H] arachidonic acid metabolites released in the reaction solution is measured using a scintillation counter.

When the amount of [$^3$H] arachidonic acid metabolites when 500 μl of the reaction buffer alone is added (neither the ligand of the present invention nor the test compound is added) is taken as 0% and the amount of [$^3$H] arachidonic acid metabolites when the reaction buffer containing 10 μM of the ligand of the present invention is added (no test compound is added) is taken as 100%, the amount of [$^3$H] arachidonic acid metabolites released where the test compound is added is calculated.

The compound showing the arachidonic acid metabolite-releasing activity of, e.g., 50% or less, can be selected as a candidate substance capable of competitive inhibition.

(5) In the cells where the receptor of the present invention is expressed, the intracellular Ca level increases by stimulation of the ligand of the present invention. Utilizing this reaction, the stimulating activities of the ligand of the present invention on the cells where the receptor of the present invention is expressed are assayed, whereby the compound that changes the binding properties of the ligand of the present invention to the receptor of the present invention can be screened. As the cells where the receptor of the present invention is expressed, there can be used the cells transformed by an expression vector bearing a DNA encoding the receptor or partial peptide of the present invention, mast cells, microglial cells (e.g., rat primary culture microglial cells), etc.

Specifically, the compound that changes the binding properties of the ligand of the present invention to the receptor of the present invention is screened by assaying the intracellular calcium level increasing activities when the ligand of the present invention is brought in contact with the cells where the receptor of the present invention is expressed (e.g., microglial cells) and when the ligand of the present invention and a test compound are brought in contact with the cells where the receptor of the present invention is expressed; and comparing the activities. The assay is carried out in accordance with methods publicly known.

In this method, the test compound that suppresses the intracellular calcium level increasing activity by the ligand of the present invention can be selected as a candidate substance capable of competitive inhibition.

On the other hand, the agonist can be screened as well by assaying an increase of fluorescence intensity by the addition of a test compound alone.

A specific example of the screening method is described below.

The cells where the receptor of the present invention is expressed are plated on a sterilized cover glass for microscopy. Two days after, the culture medium is replaced by HBSS in which 4 mM Fura-2 AM (Dojin Chemical Laboratory) is suspended, followed by allowing to stand at room temperature for 2 hours and 30 minutes. After washing with HBSS, the cover glass is set on a cuvette, and an increased ratio of fluorescence intensity at 505 nm is measured with a fluorescence spectrophotometer at excited wavelengths of 340 nm and 380 nm, when the ligand of the present invention or the ligand of the present invention and a test compound is/are added, and comparison is made.

Also, FLIPR (manufactured by Molecular Device) may be used. Fluo-3 AM (manufactured by Dojin Kagaku Kenkyusho) is added to a suspension of the cells where the receptor of the present invention is expressed, thereby to take Fluo-3 AM into the cells. After the supernatant is washed several times through centrifugation and the cells are plated on a 96-well plate. After setting in the FLIPR device, the ligand of the present invention or the ligand of the present invention and a test compound is/are added thereto. Using a fluorescence spectrophotometer, an increase in the ratio of fluorescence intensity is measured and comparison is made, as in Fura-2.

Furthermore, the compound that changes the binding properties of the ligand of the present invention to the receptor of the present invention can also be screened by co-expressing a gene (e.g., aequorin, etc.) for the protein that emits light in response to increased Ca ions in the cells where the receptor of the present invention is expressed, and utilizing the luminescence emitted by conformational switch of the gene protein (e.g., aequorin, etc.) to the Ca-bound protein.

The cells where the receptor of the present invention is expressed and the gene of protein capable of emitting light by increasing the intracellular Ca ions is co-expressed, are plated on a 96-well plate. The ligand of the present invention or the ligand of the present invention and a test compound is/are added thereto and using a fluorescence spectrophotometer, an increase in the ratio of fluorescence intensities is measured and comparison is made as described above.

The test compound that suppresses the increase in fluorescence intensity by the ligand of the present invention can be selected as a candidate substance capable of competitive inhibition.

It has become clear that the receptor of the present invention is expressed in microglial cells in the central nervous system and shows anti-inflammatory effects by stimulation with lysoPS (see EXAMPLE 15 described later), and the screening method using microglial cells is useful for screening preventive/treatment of central nervous disorders.

(6) When the receptor agonist is added to receptor-expressing cells, the level of intracellular inositol triphosphate increases. By utilizing the intracellular inositol triphosphate producing activity in the cells where the receptor of the present invention is expressed, the compound that changes the binding properties of the ligand of the present invention to the receptor of the present invention can be screened.

Specifically, the compound that changes the binding properties of the ligand of the present invention to the receptor of the present invention is screened by assaying the inositol triphosphate producing activities in the presence of labeled inositol, when the ligand of the present invention is brought in contact with the cells where the receptor of the present invention is expressed and when the ligand of the present invention and a test compound are brought in contact with the cells where the receptor of the present invention is expressed; and comparing the activities. The assay is carried out in accordance with methods publicly known.

In this method, the test compound that suppresses the inositol triphosphate producing activities can be selected as a candidate substance capable of competitive inhibition.

On the other hand, an agonist can also be screened by contacting a test compound alone with the cells where the receptor of the present invention is expressed and measuring an increase in the inositol triphosphate production.

A specific example of the screening method is described below.

The cells wherein the receptor of the present invention is expressed are plated on a 24-well plate and cultured for a day. Then, the cells are cultured for a day in medium supplemented with myo-[$2^{-3}$H] inositol (2.5 µCi/well). The cells are thoroughly washed with radioactive inositol-free medium. After the ligand of the present invention or the ligand of the present invention and a test compound is/are added to the cells, 10% perchloric acid is added to terminate the reaction. The reaction mixture is neutralized with 1.5 M KOH and 60 mM HEPES solution and then passed through a column packed with 0.5 ml of AG1×8 resin (Bio-Rad). After washing with 5 mM sodium tetraborate ($Na_2B_4O_7$) and 60 mM ammonium formate, the radioactivity eluted with 1M ammonium formate and 0.1M formic acid is assayed with a liquid scintillation counter. When the radioactivity without adding the ligand of the present invention is made 0% and the radioactivity when the ligand of the present invention is added is made 100%, an effect of the test compound on the binding of the ligand of the present invention to the receptor of the present invention is calculated.

A test compound which reduces the inositol triphosphate production activity to, e.g., 50% or less, can be selected as a candidate substance capable of competitive inhibition.

(7) The compound that changes the binding properties of the ligand of the present invention to the receptor of the present invention can be screened by assaying the stimulating activities of the ligand of the present invention on the cells where the receptor of the present invention is expressed, using a TRE-reporter gene vector.

A DNA containing TRE (TPA response element) is inserted into a vector upstream the reporter gene to acquire a TRE-reporter gene vector. In the TRE-reporter gene vector-transfected cells where the receptor of the present invention is expressed, stimulation accompanied by an increase of the intracellular Ca level induces expression of TRE-mediated reporter gene and production of the reporter gene product (protein) subsequent thereto. That is, changes in the calcium level in the TRE-reporter gene vector-transfected cells can be detected by assaying the enzyme activity of the reporter gene protein.

Specifically, the compound that changes the binding properties of the ligand of the present invention to the receptor of the present invention is screened by assaying the enzyme activities of the reporter gene protein, when the ligand of the present invention is brought in contact with the TRE-reporter gene vector-transfected cells where the receptor of the present invention is expressed and when the ligand of the present invention and a test compound are brought in contact with the TRE-reporter gene vector-transfected cells where the receptor of the present invention is expressed; and comparing the activities.

As the vector, there may be employed, e.g., PicaGene Basic Vector, PicaGene Enhancer Vector (Toyo Ink Mfg. Co., Ltd.), and the like. A DNA containing TRE is inserted into the vector described above at the multicloning site upstream the reporter gene, e.g., luciferase gene, which is made a TRE-reporter gene vector.

In this method, the test compound that suppresses the enzyme activity of the reporter gene protein by the ligand of the present invention can be selected as a candidate substance capable of competitive inhibition.

On the other hand, the agonist can be screened as well by contacting a test compound alone with the TRE-reporter gene vector-transfected cells where the receptor of the present invention is expressed and measuring the increased luminescence level as in the ligand of the present invention.

Taking as an example the embodiment wherein luciferase is used as the reporter gene, a specific example of this screening method is described below.

The TRE-reporter gene (luciferase)-transfected cells where the receptor of the present invention is expressed are plated on a 24-well plate in $5 \times 10^3$ cells/well followed by cultivation for 48 hours. After the cells are washed with Hanks' balanced salt solution (pH 7.4) containing 0.05% BSA and 20 mM HEPES, 10 nM of the ligand of the present invention or 10 nM of the ligand of the present invention and a test compound is/are added to the cells, followed by reacting at 37° C. for 60 minutes. The cells are dissolved in a cell lysis agent for PicaGene (Toyo Ink Mfg. Co., Ltd.) and a luminescence substrate (Toyo Ink Mfg. Co., Ltd.) is added to the lysate. The luminescence by luciferase is measured by a luminometer, a liquid scintillation counter or a top counter. The amounts of luminescence by luciferase are measured when the ligand of the present invention is added and when 10 nM of the ligand of the present invention and a test compound are added, and compared therebetween.

In response to the increased intracellular calcium by the ligand of the present invention, the amount of luminescence by luciferase increases. The compound that suppresses the increase can be selected as a candidate substance capable of competitive inhibition.

As the reporter gene, there may be employed genes, e.g., alkaline phosphatase, chloramphenicol acetyltransferase, β-galactosidase, etc. The enzyme activities of these reporter gene proteins are assayed in accordance with methods publicly known, or by using assay kits commercially available. The alkaline phosphatase activity can be assayed by using, e.g., Lumi-Phos 530 manufactured by Wako Pure Chemical Industries, Ltd.; the chloramphenicol acetyltransferase activity using, e.g., FAST CAT chloramphenicol Acetyltransferase Assay Kit manufactured by Wako Pure Chemical Industries, Ltd.; and the β-galactosidase activity using, e.g., Aurora Gal-XE manufactured by Wako Pure Chemical Industries, Ltd.

(8) In the cell where the receptor of the present invention is expressed, MAP kinase (e.g., ERK1, ERK2, etc.) is activated by stimulation of the ligand of the present invention. Utilizing the reaction, the compound that changes the binding properties of the ligand of the present invention to the receptor of the present invention, the compound that promotes or inhibits the activation of the present invention, etc. can be screened by assaying the stimulation activities of the ligand of the present invention on the cell where the receptor of the present invention is expressed.

Specifically, the compound that changes the binding properties of the ligand of the present invention to the receptor of the present invention, the compound that promotes or inhibits the activation of the receptor of the present invention, etc. is screened by assaying the cell growth, when the ligand of the present invention is brought in contact with the cells where the receptor of the present invention is expressed and when the ligand of the present invention and a test compound are brought in contact with the cells where the receptor of the present invention is expressed; and comparing the cell growth.

The growth of the cells where the receptor of the present invention is expressed may be determined by assaying, e.g., the MAP kinase activity (e.g., ERK1, ERK2, etc.), the thymidine uptake activity, the cell count, etc.

In a specific example, the MAP kinase activity is assayed as follows. The ligand of the present invention or the ligand of the present invention and a test compound is/are added to the cell where the receptor of the present invention is expressed; immunoprecipitation is carried out using an anti-MAP kinase antibody to obtain a MAP kinase fraction from a cell lysate; then using, e.g., MAP Kinase Assay Kit manufactured by Wako Pure Chemical Industries, Ltd. and $\gamma$-[$^{32}$P]-ATP, the MAP kinase activity is assayed; and comparison is made.

Alternatively, the ligand of the present invention and a test compound image analyzer are added to the cells where the receptor of the present invention is expressed, to obtain the cell lysate. The cell lysate is separated by known methods, e.g., using polyacrylamide gel, and transferred to a filter. Then, the MAP kinase activity is detected by an image analyzer, etc. using a MAP kinase-specific antibody and chemiluminescent reagents, and intensities of chemiluminescence are compared.

The thymidine uptake activity can be assayed by plating on a 24-well plate the cell where the receptor of the present invention is expressed, followed by incubation. After the ligand of the present invention or the ligand of the present invention and a test compound is/are added to the cells, and radioactively labeled thymidine (e.g., [methyl-3H]-thymidine, etc.) is added thereto. Then the cells are lysed and by counting the radioactivity of the labeled thymidine taken up into the cells with a liquid scintillation counter, the thymidine uptake activity is assayed and comparison is made.

To determine the cell counting, the cells where the receptor of the present invention is expressed are plated on a 24-well plate, followed by incubation. The ligand of the present invention or the ligand of the present invention and a test compound is/are added to the cells, and MTT (3-(4,5-dimethyl-2-thiazolyl)-2,5-diphenyl-2H-tetrazolium bromide) is further added thereto. MTT taken up into the cells changes to MTT formazan, which absorption is measured at 570 nm, after cell lysis with an aqueous isopropanol solution rendered acidic with hydrochloric acid. Then, comparison is made.

In this method, the test compound that suppresses the growth of the cells where the receptor of the present invention is expressed can be selected as a candidate substance capable of competitive inhibition.

On the other hand, the agonist may be screened as well by contacting a test compound alone with the cells where the receptor of the present invention is expressed and assaying the cell growth activity as in the ligand of the present invention.

A specific example of the screening method utilizing the thymidine uptake activity is described below.

The cells where the receptor of the present invention is expressed are plated on a 24-well plate in 5000 cells/well followed by incubation for one day. Next, the cells are incubated in a serum-free medium for 2 days to bring the cells under starvation. The ligand of the present invention or the ligand of the present invention and a test compound is/are added to the cells. After incubation for 24 hours, [methyl-3H] thymidine is added in 0.015 MBq/well, followed by incubation for 6 hours. After the cells are washed with PBS, methanol is added to the cells. The mixture is allowed to stand for 10 minutes. Next, 5% trichloroacetic acid is added and the mixture is allowed to stand for 15 minutes. The immobilized cells are washed 4 times with distilled water. After cell lysis with a 0.3 N sodium hydroxide solution, the radioactivity in the lysate is assayed with a liquid scintillation counter.

The compound that suppresses the increase in radioactivity by the addition of the ligand of the present invention can be selected as a candidate substance capable of competitive inhibition.

(9) In the cell where the receptor of the present invention is expressed, the potassium channel is activated by stimulation of the ligand of the present invention so that K ions present within the cells are effluxed outside the cells. Utilizing this reaction, the compound that changes the binding properties of the ligand of the present invention to the receptor of the present invention can be screened by assaying the stimulating activities of the ligand of the present invention on the cells where the receptor of the present invention is expressed.

Rb ions (rubidium ions) in the related elements to K ions flow out of the cells through the potassium channel without being discriminated from K ions. Thus, radioactive isotope $R^b$ ([$^{86}$Rb]) is previously incorporated into the cells where the receptor of the present invention is expressed, and the efflux of $^{86}$Rb that flows out in response to stimulation by the ligand of the present invention (efflux activity) is determined thereby to assay the stimulating activities of the ligand of the present invention on the cells where the receptor of the present invention is expressed.

Specifically, the compound that changes the binding properties of the ligand of the present invention to the receptor of the present invention is screened by assaying $^{86}$Rb efflux activities in the presence of $^{86}$Rb, when the ligand of the present invention is brought in contact with the cells where the receptor of the present invention is expressed and when the ligand of the present invention and a test compound are brought in contact with the cells where the receptor of the present invention is expressed; and comparing the activities.

In this method, the test compound that suppresses the increase of the $^{86}$Rb efflux activities associated with stimulation by the ligand of the present invention can be selected as a candidate substance capable of competitive inhibition.

On the other hand, the agonist can be screened as well by contacting a test compound alone with the cell where the receptor of the present invention is expressed and measuring the increase in the efflux activity of $^{86}$Rb.

A specific example of the screening method is described below.

The cells where the receptor of the present invention is expressed are plated on a 24-well plate and cultured for 2 days. Thereafter, the cells are kept warm for 2 hours in a medium containing 1 mCi/ml of $^{86}$RbCl. The medium is thoroughly washed to completely remove $^{86}$RbCl in the outer liquid. The ligand of the present invention or the ligand of the present invention and a test compound is/are added to the cells. After the outer liquid is recovered 30 minutes after, the radioactivity is measured with a $\gamma$ counter, and comparison is made.

The test compound which suppresses the increase in the efflux activity of $^{86}$Rb by stimulation of the ligand of the present invention can be selected as a candidate substance capable of competitive inhibition.

(10) The cell where the receptor of the present invention is expressed reacts with the ligand of the present invention so that the extracellular pH changes. Utilizing this reaction, the compound that changes the binding properties of the ligand of the present invention to the receptor of the present invention can be screened by assaying the stimulating activities of the ligand of the present invention on the cell where the receptor of the present invention is expressed.

Specifically, the compound that changes the binding properties of the ligand of the present invention to the receptor of the present invention is screened by measuring changes in extracellular pH, when the ligand of the present invention is brought in contact with the cells where the receptor of the present invention is expressed and when the ligand of the present invention and a test compound are brought in contact with the cells where the receptor of the present invention is expressed; and comparing the changes.

The extracellular pH change is determined using, e.g., Cytosensor Device (Molecular Device, Inc.).

In this method, the test compound that suppresses the extracellular pH change by the ligand of the present invention can be selected as a candidate substance capable of competitive inhibition.

On the other hand, the agonist can be screened as well by contacting a test compound alone with the cell where the receptor of the present invention is expressed and measuring the extracellular pH changes, as in the ligand of the present invention.

A specific example of the screening method is described below.

The cells where the receptor of the present invention is expressed are cultured overnight in a capsule for Cytosensor Device, which is set in a chamber of the device to reflux 0.1% BSA-containing RPMI 1640 medium (manufactured by Molecular Device, Inc.) until the extracellular pH becomes stable. After the pH becomes stable, a medium containing the ligand of the present invention or the ligand of the present invention and a test compound is refluxed onto the cells. The pH changes in the medium caused by reflux are measured and compared.

The compound that suppresses the extracellular pH change by the ligand of the present invention can be selected as a candidate substance capable of competitive inhibition.

(11) In yeast (*Saccharomyces Cerevisiae*), the sex pheromone receptor STe2 of haploid α-mating type (MATα) is coupled to G protein Gpa1 and activates MAP kinase in response to the sex pheromone α-mating factor, whereby Far1 (cell-cycle arrest) and the transcription activator Ste12 are activated. Ste12 induces expression of various proteins (e.g., FUS1 which takes part in mating). On the other hand, regulator Sst2 functions to inhibit the foregoing process. In this system, an attempt has been made to construct the assay system for the reaction of a receptor agonist with a receptor, which involves preparing a receptor gene-transfected yeast, activating the intracellular signal transduction system in yeast by stimulation with the receptor agonist and using the resulting growth, etc. as an indicator (Trends in Biotechnology, 15, 487-494, 1997). Utilizing this receptor gene-transfected yeast system, the compound that changes the binding properties of the ligand of the present invention to the receptor of the present invention can be screened.

A specific example is described below.

Ste2 in MATα yeast and the gene encoding Gpa1 are removed and instead, a gene for the receptor of the present invention and a gene encoding the Gpa1-Gai2 fused protein are introduced. The gene encoding Far is removed to cause no cell-cycle arrest and the gene encoding Sst is removed to increase the sensitivity in response to the ligand of the present invention. Furthermore, FUS1-HIS3 gene, which is FUS1 ligated with histidine biosynthesis gene HIS3, is introduced. The foregoing genetic recombinant engineering can be carried out by the method described in, e.g., Molecular and Cellular Biology, A, 6188-6195, 1995, using the receptor of the present invention in place of somatostatin receptor type 2 (SSTR2) gene.

The thus constructed transformant yeast is responsive to the ligand of the present invention with a high sensitivity so that MAP kinase is activated to cause synthesis of histidine biosynthesis enzyme. Thus, the transformant becomes capable of growing in a histidine-deficient medium.

Accordingly, the compound that changes the binding properties of the ligand of the present invention to the receptor of the present invention can be screened by incubating the yeast described above where the receptor of the present invention is expressed (MATα yeast wherein Ste2 gene and Gpa1 gene are removed, the receptor gene of the present invention and the Gpa-Gai2 fused protein-encoding gene, Far gene and Sst gene are removed, and S1-HIS3 gene is transfected) in a histidine-deficient medium, contacting the ligand of the present invention or the ligand of the present invention and a test compound with the yeast, assaying growth of the yeast, and comparing the growth.

In this method, the test compound that suppresses growth of the yeast can be selected as a candidate substance capable of competitive inhibition.

On the other hand, the agonist can be screened as well by contacting a test compound alone with the yeast where the receptor of the present invention is expressed and assaying growth of the yeast as in the ligand of the present invention.

A specific example of the screening method is described below.

The yeast described above where the receptor of the present invention is expressed thus produced is incubated overnight in a complete synthesis liquid medium and then added to a histidine-free, dissolved agar medium in a concentration of $2 \times 10^4$ cells/ml. Then, the yeast is plated on a square Petri dish of 9×9 cm. After the agar is solidified, a sterilized filter paper impregnated with the ligand of the present invention or the ligand of the present invention and a test compound is put on the agar surface, which is incubated at 30° C. for 3 days. To determine the effect of the test compound, growth of yeast around the filter paper is compared to the case wherein the sterilized filter paper impregnated only with the ligand of the present invention. Alternatively, the assay can be made by previously adding the ligand of the present invention to a histidine-free agar medium, impregnating the sterilized, filter paper with a test compound alone to incubate the yeast and monitoring that growth of the yeast over the entire surface of the Petri dish is affected at the periphery of the filter paper.

The compound that suppresses growth of the yeast can be selected as a candidate substance capable of competitive inhibition.

(12) When the receptor gene RNA of the present invention is injected into *Xenopus laevis* oocytes and stimulated by the ligand of the present invention, the intracellular Ca ion level increases to cause a calcium-activated chloride current, which can be taken as fluctuation in membrane potential (the same applies also to the case where fluctuation occurs in K ion level gradient). Utilizing the above reaction caused by the ligand of the present invention in *Xenopus laevis* oocytes where the receptor of the present invention is transfected, the compound that changes the binding properties of the ligand of the present invention to the receptor of the present invention can be screened by assaying the stimulating activities of the ligand of the present invention on the cells where the receptor of the present invention is expressed.

Specifically, the compound that changes the binding properties of the ligand of the present invention to the receptor of the present invention can be screened by assaying changes in cell membrane potential, when the ligand of the present invention is brought in contact with *Xenopus laevis* oocytes where the receptor gene RNA of the present invention is transfected and when the ligand of the present invention and a test compound are brought in contact with *Xenopus laevis* oocytes where the receptor gene RNA of the present invention is transfected; and comparing the changes.

In this method, the test compound that suppresses the changes in cell membrane potential can be selected as a candidate substance capable of competitive inhibition.

On the other hand, the agonist can be screened as well by contacting a test compound alone with *Xenopus laevis* oocytes where the receptor gene RNA of the present invention is transfected and assaying the changes in cell membrane potential as in the ligand of the present invention.

A specific example of the screening method is described below.

A female individual of *Xenopus laevis* anesthetized by immersing in ice water is anatomized to withdraw oocytes. The oocyte clusters are treated with collagenase (0.5 mg/ml) dissolved in an MBS solution (88 mM NaCl, 1 mM KCl, 0.41 mM $CaCl_2$, 0.33 mM $Ca(NO_3)_2$, 0.82 mM $MgSO_4$, 2.4 mM $NaHCO_3$, 10 mM HEPES; pH 7.4) at 19° C. for 1 to 6 hours at 150 rpm, until the oocytes are loosen. Washing is performed 3 times by replacing the outer liquid by the MBS solution followed by microinjection of the receptor gene of the present invention or poly A-added cRNA (50 ng/50 nl) with a micromanipulator.

The receptor gene mRNA of the present invention may be prepared from tissues or cells, or may be transcribed from plasmids in vitro. The receptor gene mRNA of the present invention is incubated in the MBS solution at 20° C. for 3 days. The oocytes are placed in a hole of a voltage clamp device, which is continuously perfused with Ringer's solution, and impaled into the cells with glass microelectrodes for voltage clamp and glass microelectrodes for potential recording, in which (−) electrode is placed outside the oocytes. When the holding potential stabilizes, Ringer's solution containing the ligand of the present invention or the ligand of the present invention and a test compound is perfused to record a change in potential. An effect of the compound can be determined by comparing a change in cell membrane potential of the *Xenopus laevis* oocytes where the receptor gene RNA of the present invention is transfected with the case when the Ringer's solution containing the ligand of the present invention alone is perfused.

The compound that suppresses the changes in cell membrane potential can be selected as a candidate substance capable of competitive inhibition.

In the system described above, the changes in potential can be monitored more easily when the variations in potential increase. Therefore, polyA-added RNA of various G protein genes may be introduced. Also, the amount of luminescence, not the changes in membrane potential, can be measured by co-injecting polyA-added RNA of a gene for the protein (e.g., aequorin, etc.) that emits light in the presence of calcium.

Furthermore, the screening methods using mammal-derived mast cells and microglial cells are described below.

Using mast cells (including mast cell lines, adipose tissues, etc.) derived from mammal (preferably, human, guinea pig, rat, mouse), preferably mast cells derived from the peritoneal cavity, skin, lung, etc., compounds having the IL-13 production inhibitory action, mast cell degranulation inhibitory action, eicosanoid production inhibitory action, mast cell growth inhibitory action, etc. can be screened. In this case, costimulation may be given to mast cells before and after addition of the ligand. For costimulation, there are used concanabalin A, lectins such as wheat germ lectin, lentil lectin, kidney bean lectin, pokeweed lectin, *Datura* stramonium lectin, etc., neuropeptide, neurotropic factor, stem cell growth factor, etc. Where mast cells are sensitized by an antibody, its antigen may also be used.

(1) The IL-13 production inhibitor (compound having the IL-13 production inhibitory action, etc.) is screened by contacting the ligand of the present invention with mast cells in the presence and absence of a test compound to prepare RNA from the cells, assaying the IL-13 RNA levels (by, e.g., RT-PCR, quantitative real-time-PCR, etc.) and comparing the levels.

(2) The IL-13 production inhibitor (compound having the IL-13 production inhibitory action, etc.) is screened by contacting the ligand of the present invention with mast cells in the presence and absence of a test compound, assaying the IL-13 protein levels in the supernatant (by, e.g., EIA, RIA; etc.) and comparing the levels.

(3) The IL-13 production inhibitor (compound having the IL-13 production inhibitory action, etc.) is screened by contacting the ligand of the present invention with mast cells in the presence and absence of a test compound, assaying the counts of IL-13 producing cells (by, e.g., the ELISPOT method) and comparing the counts.

(4) The IL-13 production inhibitor (compound having the IL-13 production inhibitory action, etc.) is screened by producing a number of siRNA vectors (e.g., siRNA vector, antisense oligonucleotide, antisense oligonucleotide expression vector, etc.) bearing siRNA for polynucleotide encoding the receptor of the present invention to prepare the siRNA library, transfecting the vectors into mast cells, contacting with the ligand of the present invention in the presence and absence of a test compound, assaying the expression levels of IL-13 (e.g., IL-13 RNA levels, IL-13 protein levels, etc.) in the cells and examining the base sequence of siRNA inducing a reduction in expression level. In contacting with the ligand, costimulation may be provided by an anti-IgE antibody, an antibody, an antibody-specific antigen, etc. where mast cells undergo active or passive sensitization and in other cases, costimulation may be provided by NGF, stem cell factor (SCF), cytokine, lectin, etc.

(5) The eicosanoid production inhibitor (compound having the eicosanoid production inhibitory action, etc.) is screened by contacting the ligand of the present invention with mast cells, in which radioactively labeled arachidonate is incorporated, in the presence and absence of a test compound, assaying the radioactivities in the culture supernatant and comparing the radioactivities.

(6a) The degranulation inhibitor (compound having the degranulation inhibitory action, etc.) is screened by contacting the ligand of the present invention with mast cells in the presence and absence of a test compound, assaying the amounts of granule contents (e.g., histamine, serotonin, β-hexosaminidase, β-glucuronidase, tryptase, chymase, carboxypeptidase, etc.) in the culture supernatant, and comparing the amounts. The amounts of granule contents can be quantified by known methods, e.g., EIA, RIA, HPLC, enzyme activity measurement, etc. Alternatively, mast cells may be visualized (e.g., a video equipment, etc.) to count the degranulated cells.

(6b) The degranulation inhibitor (compound having the degranulation inhibitory action, etc.) is screened by contacting the ligand of the present invention with mast cells, in which radioactively labeled granule contents are incorporated, in the presence and absence of a test compound, assaying the radioactivities in the culture supernatant, and comparing the radioactivities.

(6c) The degranulation inhibitor (compound having the degranulation inhibitory action, etc.) is screened by contacting the ligand of the present invention with mast cells in the presence and absence of a test compound, assaying the binding amounts of annexin V to the mast cells (e.g., FACS, etc.) and comparing the amounts.

(6d) The compound having the IL-10 production promoting action or the IL-10 production inhibitory action is screened by contacting the ligand of the present invention with microglial cells stimulated by FN-γ and LPS in the presence and absence of a test compound, assaying the IL-10 expression levels (e.g., IL-10 RNA levels, IL-10 protein levels, etc.) and comparing the levels.

(6e) The compound having the IL-6 production inhibitory action is screened by contacting the ligand of the present invention with microglial cells stimulated by IFN-γ and LPS in the presence and absence of a test compound, assaying the IL-6 expression levels (e.g., IL-6 RNA levels, IL-6 protein levels, etc.) and comparing the levels.

(6f) The compound having the TNF-α production inhibitory action is screened by contacting the ligand of the present invention with microglial cells stimulated by IFN-γ and LPS in the presence and absence of a test compound, assaying the TNF-α expression levels (e.g., TNF-α RNA levels, TNF-α protein levels, etc.) and comparing the levels.

(7) The MAP kinase activation inhibitor (compound having the MAP kinase activation inhibitory action) is screened by contacting the ligand of the present invention with mast cells in the presence or absence of a test compound, separating the cell lysate using polyacrylamide gel, transferring the gel to a filter, detecting the MAP kinase activities by an image analyzer, etc. using a MAP kinase-specific antibody and chemiluminescent reagents, and comparing the intensities of chemiluminescence.

(8) The mast cell growth inhibitor (compound having the mast cell growth inhibitory action, etc.) is screened by contacting the ligand of the present invention with mast cells (e.g., mast cells plated on a 24-well plate and then incubated) in the presence or absence of a test compound, adding radioactively labeled thymidine (e.g., [methyl-3H]-thymidine, etc.), lysing the cells, counting the radioactivities of thymidine taken up into the cells with a liquid scintillation counter, assaying the thymidine uptake activities and comparing the activities.

(9) The mast cell growth inhibitor (compound having the mast cell growth inhibitory action) is screened by contacting the ligand of the present invention with mast cells (e.g., mast cells plated on a 24-well plate and then incubated) in the presence or absence of a test compound, adding MTT (3-(4, 5-dimethyl-2-thiazolyl)-2,5-diphenyl-2H-tetrazolium bromide), lysing the cells in an aqueous isopropanol solution rendered acidic with hydrochloric acid, measuring the amounts of MTT formazan changed from the MTT taken up into the cells by absorption at 570 nm, and comparing the amounts.

The kit for screening the compound or its salt that changes the binding properties of the ligand of the present invention to the receptor of the present invention comprises the receptor of the present invention or the cell or cell membrane fraction containing the receptor of the present invention, and the ligand of the present invention.

Examples of the screening kits of the present invention are as follow.

1. Reagents for Screening
(i) Assay Buffer and Wash Buffer

Hanks' balanced salt solution (manufactured by Gibco Co.) supplemented with 0.05% bovine serum albumin (manufactured by Sigma Co.).

The solution is sterilized by filtration through a 0.45 μm filter, and stored at 4° C. or may be prepared at use.
(ii) Preparation of the Receptor of the Present Invention CHO cells where the receptor of the present invention is expressed are subcultured on a 12-well plate at a density of $5 \times 10^5$ cells/well and cultured at 37° C. under 5% $CO_2$ and 95% air for 2 days.
(iii) Labeled Ligand The ligand of the present invention labeled with radioisotope such as [$^3$H], [$^{125}$I], [$^{14}$C], [$^{32}$P], [$^{33}$P], [$^{35}$S], etc. A solution of the ligand dissolved in an appropriate solvent or buffer is stored at 4° C. or −20° C. and upon use, diluted to 1 μM with the assay buffer.
(iv) Standard Ligand Solution The ligand of the present invention is dissolved in PBS containing 0.1% bovine serum albumin (manufactured by Sigma Co.) in a volume of 1 mM, and the solution is stored at −20° C.

2. Assay Method (i) The cells where the receptor of the present invention is expressed are cultured on a 12-well culture plate. After washing twice with 1 ml of the assay buffer, 490 μl of the assay buffer is added to each well.

(ii) After 5 μl of a solution of test compound in $10^{-3}$ to $-10^{10}$ M is added, 5 μl of a labeled form of the ligand of the present invention is added thereto. The reaction is carried out at room temperature for an hour. To examine the non-specific binding, 5 μl of the ligand of the present invention of $10^{-3}$ M is previously added in place of the test compound.

(iii) The reaction solution is removed and the wells are washed 3 times with 1 ml of the wash buffer. The labeled ligand of the present invention bound to the cells is dissolved in 0.2N NaOH-1% SDS, and mixed with 4 ml of liquid scintillator A (manufactured by Wako Pure Chemical Industries, Ltd.).

(iv) The radioactivity is measured using a liquid scintillation counter (manufactured by Beckman Co.), and the percent maximum binding (PMB) is calculated in accordance with the following equation.

$$PMB = [(B - NSB)/(B_0 - NSB)] \times 100$$

PMB: Percent maximum binding
B: Value obtained in the presence of a test compound
NSB: Non-specific binding
$B_0$: Maximum binding The compound or its salt, which is obtainable by using the screening methods or the screening kits of the present invention, is the compound that changes the binding of the ligand of the present invention to the receptor of the present invention, or the compound that promotes or inhibits the activity of the receptor of the present invention and specifically, includes (i) the compound or its salt having the cell stimulating activities mediated by the receptor of the present invention (an agonist to the receptor of the present invention); (ii) the compound having no stimulating activity (an antagonist to the receptor of the present invention); (iii) the compound that promotes the binding affinity of the receptor of the present invention and the ligand of the present invention; (iv) the compound that inhibits the binding affinity of the receptor of the present invention and the ligand of the present invention; or the like. Examples of these compounds include those selected from peptides, proteins, non-peptide compounds, synthetic compounds, fermentation products, cell extracts, plant extracts, animal tissue extracts, blood plasma, etc. These compounds may be novel or publicly known compounds.

The same salts given for the receptor of the present invention above apply to the salts of these compounds.

Evaluation of whether the compound is the receptor agonist or antagonist of the present invention described above is determined by, e.g., (i) or (ii) below.

(i) The binding assay according to the screening methods (i) to (iii) is performed to obtain the compound that changes the binding properties of the ligand of the present invention to the receptor of the present invention (especially inhibits the binding). It is then determined if the compound has the cell stimulating activities mediated by the receptor of the present invention as described above. The compound or its salt that has the cell-stimulating activities is the receptor agonist of the present invention (agonist), whereas the compound having no such activities or its salt is the receptor antagonist of the present invention (antagonist).

(ii) (a) A test compound is brought in contact with cells containing the receptor of the present invention to assay the cell stimulating activities mediated by the receptor of the present invention. The compound or its salts having the cell stimulating activities is the receptor agonist of the present invention.

(b) The cell stimulating activities mediated by the receptor of the present invention are assayed when the ligand of the present invention is brought in contact with the cell containing the receptor of the present invention and when the ligand of the present invention and a test compound are brought in contact with the cell containing the receptor of the present invention, and comparison is made on the cell stimulating activities. The compound or its salt capable of reducing the cell stimulating activities by the compound that activates the receptor of the present invention is the receptor antagonist of the present invention.

The receptor antagonist of the present invention can suppress the physiological activities (e.g., IL-13 production promoting activities, mast cell degranulation promoting activities, eicosanoid (e.g., leukotriene, prostaglandin, etc.) promoting activities, mast cell growth promoting activities, etc.) possessed by the ligand of the present invention and thus can be used as a low-toxic and safe IL-13 production inhibitor, mast cell degranulation inhibitor or eicosanoid (e.g., leukotriene, prostaglandin, etc.) production inhibitor as an agent for preventing/treating, for example, immune disorders [e.g., inflammatory diseases (pituitary tumor, thyroiditis, peritonitis, Crohn's disease, ulcerative colitis, erythema nodosum, chronic rheumatoid arthritis, systemic lupus erythematosus, etc.), allergy (e.g., allergic conjunctivitis, allergic rhinitis, pollinosis, metal allergy, etc.), asthma, exudative otitis media, Meniere's disease, contact dermatitis, anaphylaxis, urticaria, myasthenia gravis, glomerulonephritis, Sjögren's syndrome, Basedow's disease, insulin resistant diabetes, atopic dermatitis, leukocyte abnormality, etc.], respiratory disorders [e.g., chronic obstructive pulmonary disease (e.g., chronic bronchitis, pulmonary emphysema), diffuse panbronchiolitis, cystic fibrosis, hypersensitivity penumonitis, idiopathic interstitial pneumonia, pulmonary fibrosis, etc.], urinary tract disorders (e.g., renal tubulointerstitial injuries (fibrosis), interstitial cystitis, allergic cystitis, etc.), circulatory diseases (e.g., arteriosclerosis, acute coronary syndrome, atherosclerotic aortic aneurysm, cardiac anaphylaxis, heart failure, myocardial infarction, angina pectoris, arrhythmia, deep venous thrombosis, restenosis after PTCA, etc.), ophthalmic disorders (e.g., pterygium, vernal catarrh, dry eyes, etc.), cancer (e.g., papillary thyroid carcinoma, non-small cell lung cancer, endometrial cancer, cervical cancer, gastric cancer, pancreatic cancer, lung cancer, renal cancer, liver cancer, ovarian cancer, prostate cancer, bladder cancer, breast cancer, colon cancer, rectal cancer, Kaposi's sarcoma, mastocytoma, etc.), digestive disorders [e.g., chronic liver disease, food allergy, allergic enteritis, milk protein-induced proctitis, peptic ulcer (e.g., gastric ulcer, duodenal ulcer, marginal ulcer, Zollinger-Ellison syndrome, etc.), gastritis, reflux esophagitis, NUD (Non Ulcer Dyspepsia), gastric MALT lymphoma, non-steroidal anti-inflammatory drug-induced ulcer, hyperacidity, postoperative stress-induced hyperacidity and ulcer, etc.], cerebral infarction, hyperlipemia, acute renal failure, diabetes mellitus, obesity, edema, granuloma, atopic myelitis, neurofibroma, nasal mucosa hypersensitivity, Hodgkin's disease, endometrial hyperplasia, central nervous disorders [e.g., neurodegenerative disease (e.g., Alzheimer's disease (familial Alzheimer's disease, juvenile Alzheimer's disease, sporadic Alzheimer's disease, etc.), Parkinson's disease, Down's syndrome, amyotrophic lateral sclerosis, prion disease (Creutzfeldt-Jakob disease), Huntington's chorea, diabetic neuropathy, multiple sclerosis, etc.), mental disorders (e.g., schizophrenia, depression, bipolar disorders, anxiety disorders, attention deficit hyperactivity disorders, panic disorders, etc.), cerebrovascular disorders (e.g., cerebral thrombosis, cerebral embolism, transient ischemic attack, etc.), etc.] and the like.

The compound that inhibits the binding affinity of the receptor of the present invention to the ligand of the present invention is used as in the receptor antagonist of the present invention.

The compound that promotes the binding affinity of the receptor of the present invention to the ligand of the present invention is used as in the receptor agonist of the present invention.

In addition, the present invention provides the method of screening the compound or its salt that promotes or inhibits the expression of a gene for the receptor of the present invention, which comprises using the polynucleotide of the present invention encoding the receptor of the present invention, etc.

Specifically, the compound or its salt that promotes or inhibits the expression of a gene for the receptor of the present invention is screened by comparing the case (i) where a cell capable of producing the receptor of the present invention is cultured, with the case (ii) where a mixture of the cell capable of producing the receptor of the present invention and a test compound is cultured.

In the screening method described above, the expression level of the receptor gene of the present invention (specifically, the amount of the receptor of the present invention or the amount of mRNA encoding the receptor of the present invention, etc.) is measured in the cases (i) and (ii), and comparison is made.

Examples of the test compound include peptides, proteins, antibodies, non-peptide compounds, synthetic compounds, fermentation products, cell extracts, plant extracts, animal tissue extracts, blood plasma, and the like. These compounds may be novel or publicly known compounds.

To perform the screening method described above, the cells capable of producing the polypeptide of the present invention or the receptor of the present invention are suspended in a buffer suitable for the screening, and the suspension is prepared. Any buffer can be used so long as it does not interfere the activities of the receptor of the present invention, including a phosphate buffer or a borate buffer, having pH of about 4 to about 10 (preferably pH of about 6 to about 8), etc.

As the cells capable of producing the receptor of the present invention, there are used, for example, a host (transformant) transformed with a vector containing the DNA encoding the receptor of the present invention. Preferably, animal cells such as CHO cells, etc. are used as the host. For the screening, the transformant, in which the receptor of the present invention has been secreted extracellularly by culturing through the procedures described above, is preferably employed.

The protein level of the receptor of the present invention can be determined by publicly known methods, e.g., by measuring the polypeptide or receptor present in the cell extract, etc., using an antibody of the present invention, in accordance with methods like western blot analysis, ELISA, etc., or their modifications.

The expression level of the gene for the receptor of the present invention can be determined by publicly known methods, e.g., in accordance with methods including Northern blotting, reverse transcription-polymerase chain reaction (RT-PCR), real time PCR monitoring system (manufactured by ABI, TaqMan polymerase chain reaction), etc., or their modifications.

For example, when a test compound promotes the expression of the gene for the receptor in the case (ii) described above by at least about 20%, preferably at least 30% and more preferably at least about 50%, as compared to the case (i) above, the test compound can be selected as the compound or its salts that promote the expression of the gene for the receptor of the present invention.

For example, when a test compound inhibits the expression of the gene for the receptor of the present invention in the case (ii) described above by at least about 20%, preferably at least 30% and more preferably at least about 50%, as compared to the case (i) above, the test compound can be selected to be the compound or its salts that inhibit the expression of the gene for the receptor of the present invention.

The compound or its salt that inhibits the expression of a gene for the receptor of the present invention is used as in the receptor antagonist of the present invention.

The compound or its salt that promotes the expression (increases the expression level) of a gene for the receptor of the present invention is used as in the receptor agonist of the present invention.

The compound or its salt, which is obtained using the screening method or screening kit of the present invention, is the compound selected from, for example, peptides, proteins, non-peptide compounds, synthetic compounds, fermentation products, cell extracts, plant extracts, animal tissue extracts, blood plasma, etc. The salts of the compound used are those given above as the salts of the peptide of the present invention, and the compound that changes the binding properties of the receptor of the present invention to the ligand of the present invention, the compound that promotes or inhibits the activities or functions of the receptor of the present invention, the compound that promotes or inhibits the expression (increase or decrease the expression level) of the gene for the receptor of the present invention, etc.

The same examples given as the salts of the receptor of the present invention described above apply to the salts of these compounds.

When the compound or its salts obtained by the screening methods or kits of the present invention are used as the aforesaid medicaments (as prophylactic/therapeutic agents, etc.), the use can be performed in a conventional manner.

The compound or its salt can be administered orally, for example, in the form of tablets which may be sugar coated, if necessary, capsules, elixirs, microcapsules etc., or parenterally in the form of injections such as sterile solutions or suspensions in water or in pharmaceutically acceptable solutions other than water. For example, the compound or its salts can be mixed with carriers, flavoring agents, excipients, vehicles, preservatives, stabilizers, binders, etc. in a unit dosage form generally accepted. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, a flavoring agent such as peppermint, akamono oil and cherry, etc. When the unit dosage is in the form of a capsule, liquid carriers such as oils and fats may further be used together with the additives described above. A sterile composition for injection may be formulated in a conventional manner used to make pharmaceutical preparations, e.g., by dissolving or suspending the active ingredients in a vehicle such as water for injection with a naturally occurring vegetable oil such as sesame oil and coconut oil, etc. to prepare the pharmaceutical preparations.

Examples of an aqueous medium for injection include physiological saline and an isotonic solution containing glucose and other auxiliary agents (e.g., D-sorbitol, D-mannitol, sodium chloride, etc.), etc. and may be used in combination with an appropriate dissolution aid such as an alcohol (e.g., ethanol, etc.), a polyalcohol (e.g., propylene glycol and polyethylene glycol, etc.), a nonionic surfactant (e.g., polysorbate 80™, HCO-50, etc.), etc. Examples of the oily medium include sesame oil, soybean oil, etc., which may also be used in combination with a dissolution aid such as benzyl benzoate, benzyl alcohol, etc. The compound or its salt may further be formulated together with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

Since the pharmaceutical preparation thus obtained is safe and low toxic, it can be administered to human or other warm-blooded animal (e.g., mouse, rat, rabbit, sheep, swine, bovine, horse, fowl, cat, dog, monkey, chimpanzee, etc.).

The dose of the compound or its salt may vary depending upon the action, target disease, subject to be administered, route of administration, etc.

For example, in oral administration, the antagonist is administered to the patient (as 60 kg body weight) with interstitial cystitis normally in a dose of about 0.1 to about 100 mg, preferably about 1.0 to about 50 mg, more preferably about 1.0 to about 20 mg per day. When the antagonist is parenterally administered to the patient (as 60 kg body weight) with, e.g., interstitial cystitis in the form of an injection, it is advantageous to administer the antagonist intravenously at a daily dose of about 0.01 to about 30 mg, preferably about 0.1 to about 20 mg, more preferably about 0.1 to about 10 mg. For other animal species, the corresponding dose as converted per 60 kg weight can be administered.

[2] Quantification of the Receptor of the Present Invention

The antibody against the receptor of the present invention (hereinafter sometimes briefly referred to as the antibody of the present invention) can specifically recognize the receptor of the present invention. Therefore, the antibody can be used to quantify the receptor of the present invention in a test fluid, especially for quantification by the sandwich immunoassay, etc.

That is, the present invention provides, for example, the following methods of quantification:

(i) a method of quantifying the receptor of the present invention in a test fluid, which comprises competitively reacting the antibody of the present invention with the test fluid and a labeled form of the receptor of the present invention, and measuring the ratio of the labeled receptor of the present invention bound to the antibody; and, (ii) a method of quantifying the receptor of the present invention in a test fluid, which comprises reacting the test fluid with the antibody of the present invention immobilized on a carrier and a labeled form of the antibody of the present invention simultaneously or sequentially, and measuring the activity of the label on the immobilized carrier.

In the quantifying method (ii) described above, it is preferred that one antibody is capable of recognizing the N-terminal region in the receptor of the present invention, while another antibody is capable of reacting with the C-terminal region in the receptor of the present invention.

Using a monoclonal antibody against the receptor of the present invention, the receptor of the present invention can be assayed and can further be detected by tissue staining, or the like. For these purposes, the antibody molecule itself may be used, or F(ab')$_2$, Fab' or Fab fractions of the antibody molecule may be used as well.

The method of quantifying the receptor of the present invention using the antibody of the present invention is not particularly limited, and any method may be used, so long as the amount of antibody, antigen, or antibody-antigen complex in response to the amount of antigen (e.g., the amount of the polypeptide) in a test fluid can be detected by chemical or physical means and can be calculated from a standard curve prepared from standard solutions containing known amounts of the antigen. Advantageously used are, for example, nephrometry, competitive method, immunometric method and sandwich method; in terms of sensitivity and specificity, the sandwich method, which will be described later, is particularly preferred.

Examples of labeling agents, which are employed for the assay method using the same are radioisotopes, enzymes, fluorescent substances, luminescent substances, etc. Examples of the radioisotopes employed are [$^{125}$I], [$^{131}$I], [$^3$H], [$^{14}$C], etc. As the enzymes described above, stable enzymes with a high specific activity are preferred; for example, β-galactosidase, β-glucosidase, alkaline phosphatase, peroxidase, malate dehydrogenase and the like are used. Examples of the fluorescent substance used are fluorescamine, fluorescein isothiocyanate and the like. As the luminescent substances, there are employed, for example, luminol, luminol derivatives, luciferin, lucigenin and the like. Furthermore, the biotin-avidin system may also be used for binding an antibody or antigen to the label.

In the immobilization of antigens or antibodies, physical adsorption may be used. Alternatively, chemical binding that is conventionally used for immobilization of polypeptides, enzymes, etc. may be used as well. Examples of the carrier include insoluble polysaccharides such as agarose, dextran, cellulose, etc.; synthetic resins such as polystyrene, polyacrylamide, silicone, etc.; or glass; and the like.

In the sandwich method, the immobilized monoclonal antibody of the present invention is reacted with a test fluid (primary reaction), then with a labeled form of another monoclonal antibody of the present invention (secondary reaction), and the activity of the labeling agent on the immobilizing carrier is assayed, whereby the amount of the receptor in the test fluid can be quantified. The order of the primary and secondary reactions may be reversed, and the reactions may be performed simultaneously or with some time intervals. The methods of labeling and immobilization can be performed by modifications of those methods described above. In the immunoassay by the sandwich method, the antibody used for immobilized or labeled antibody is not necessarily from one species, but a mixture of two or more species of antibodies may be used to increase the measurement sensitivity.

In the methods of assaying the receptor of the present invention by the sandwich method, antibodies that bind to different sites of the receptor of the present invention are preferably used as the monoclonal antibodies of the present invention for the primary and secondary reactions. That is, in the antibodies used for the primary and secondary reactions, for example, when the antibody used in the secondary reaction recognizes the C-terminal region of the receptor of the present invention, it is preferable to use the antibody capable of recognizing the region other than the C-terminal region for the primary reaction, e.g., the antibody capable of recognizing the N-terminal region.

The monoclonal antibody of the present invention can be used for the assay systems other than the sandwich method, for example, the competitive method, immunometric method, nephrometry, etc.

In the competitive method, an antigen in a test fluid and a labeled antigen are competitively reacted with an antibody, and the unreacted labeled antigen (F) and the labeled antigen bound to the antibody (B) are separated (B/F separation). The amount of the labeling agent in B or F is measured, and the amount of the antigen in the test fluid is quantified. This reaction method includes a liquid phase method using a soluble antibody as an antibody, polyethylene glycol for B/F separation and a secondary antibody, etc. to the soluble antibody, and an immobilized method either using an immobilized antibody as the primary antibody, or using a soluble antibody as the primary antibody and an immobilized antibody as the secondary antibody.

In the immunometric method, an antigen in a test fluid and an immobilized antigen are competitively reacted with a definite amount of labeled antibody, the immobilized phase is separated from the liquid phase, or an antigen in a test fluid is reacted with an excess amount of labeled antibody, the immobilized antigen is then added to bind the unreacted labeled antibody to the immobilized phase, and the immobilized phase is separated from the liquid phase. Then, the amount of the labeling agent in either phase is measured to quantify the antigen in the test fluid.

In the nephrometry, insoluble precipitates produced after the antigen-antibody reaction in gel or solution are quantified. Even when the amount of an antigen in a test fluid is small and only a small amount of precipitates is obtained, laser nephrometry using scattering of laser can be advantageously employed.

For applying these immunological assay methods to the quantification methods of the present invention, any particular conditions or procedures are not required. The assay systems for the receptor of the present invention may be constructed by adding ordinary technical consideration in the art to conventional conditions and procedures in the respective methods. For the details of these general technical means, reference can be made to the following reviews and texts.

For example, reference can be made on Hiroshi Irie, ed. "Radioimmunoassay" (Kodansha, published in 1974), Hiroshi Irie, ed. "Sequel to the Radioimmunoassay" (Kodansha, published in 1979), Eiji Ishikawa, et al. ed. "Enzyme immunoassay" (Igakushoin, published in 1978), Eiji Ishikawa, et al. ed. "Immunoenzyme assay" (2nd ed.) (Igakushoin, published in 1982), Eiji Ishikawa, et al. ed. "Immunoenzyme assay" (3rd ed.) (Igakushoin, published in 1987), Methods in ENZYMOLOGY, Vol. 70 (Immunochemical Techniques (Part A)), ibid., Vol. 73 (Immunochemical Techniques (Part B)), ibid., Vol. 74 (Immunochemical Techniques (Part C)), ibid., Vol. 84 (Immunochemical Techniques (Part D: Selected Immunoassays)), ibid., Vol. 92 (Immunochemical Techniques (Part E: Monoclonal Antibodies and General Immunoassay Methods)), ibid., Vol. 121 (Immunochemical Techniques (Part I: Hybridoma Technology and Monoclonal Antibodies))(all published by Academic Press Publishing), etc.

As described above, the receptor of the present invention can be quantified with high sensitivity, by using the antibody of the present invention.

Further when an increased level of the receptor of the present invention is detected by quantifying the level of the receptor of the present invention using the antibody of the present invention, for example, the IL-13 production promoting activity, mast cell degranulation promoting activity, eicosanoid production promoting activity or mast cell growth promoting activity is enhanced. Then it can be diagnosed that it is highly likely to suffer from diseases in the future, such as immune disorders [e.g., inflammatory diseases (pituitary tumor, thyroiditis, peritonitis, Crohn's disease, ulcerative colitis, erythema nodosum, chronic rheumatoid arthritis, systemic lupus erythematosus, etc.), allergy (e.g., allergic conjunctivitis, allergic rhinitis, pollinosis, metal allergy, etc.), asthma, exudative otitis media, Meniere's disease, contact dermatitis, anaphylaxis, urticaria, myasthenia gravis, glomerulonephritis, Sjögren's syndrome, Basedow's disease, insulin resistant diabetes, atopic dermatitis, leukocyte abnormality, etc.], respiratory disorders [e.g., chronic obstructive pulmonary disease (e.g., chronic bronchitis, pulmonary emphysema), diffuse panbronchiolitis, cystic fibrosis, hypersensitivity penumonitis, idiopathic interstitial pneumonia, pulmonary fibrosis, etc.], urinary tract disorders (e.g., renal tubulointerstitial injuries (fibrosis), interstitial cystitis, allergic cystitis, etc.), circulatory diseases (e.g., arteriosclerosis, acute coronary syndrome, atherosclerotic aortic aneurysm, cardiac anaphylaxis, heart failure, myocardial infarction, angina pectoris, arrhythmia, deep venous thrombosis, restenosis after PTCA, etc.), ophthalmic disorders (e.g., pterygium, vernal catarrh, dry eyes, etc.), cancer (e.g., papillary thyroid carcinoma, non-small cell lung cancer, endometrial cancer, cervical cancer, gastric cancer, pancreatic cancer, lung cancer, renal cancer, liver cancer, ovarian cancer, prostate cancer, bladder cancer, breast cancer, colon cancer, rectal cancer, Kaposi's sarcoma, mastocytoma, etc.), digestive disorders [e.g., chronic liver disease, food allergy, allergic enteritis, milk protein-induced proctitis, peptic ulcer (e.g., gastric ulcer, duodenal ulcer, marginal ulcer, Zollinger-Ellison syndrome, etc.), gastritis, reflux esophagitis, NUD (Non Ulcer Dyspepsia), gastric MALT lymphoma, non-steroidal anti-inflammatory drug-induced ulcer, hyperacidity, postoperative stress-induced hyperacidity and ulcer, etc.], cerebral infarction, hyperlipemia, acute renal failure, diabetes mellitus, obesity, edema, granuloma, atopic myelitis, neurofibroma, nasal mucosa hypersensitivity, Hodgkin's disease, endometrial hyperplasia, central nervous disorders [e.g., neurodegenerative disease (e.g., Alzheimer's disease (familial Alzheimer's disease, juvenile Alzheimer's disease, sporadic Alzheimer's disease, etc.), Parkinson's disease, Down's syndrome, amyotrophic lateral sclerosis, prion disease (Creutzfeldt-Jakob disease), Huntington's chorea, diabetic neuropathy, multiple sclerosis, etc.), mental disorders (e.g., schizophrenia, depression, bipolar disorders, anxiety disorders, attention deficit hyperactivity disorders, panic disorders, etc.), cerebrovascular disorders (e.g., cerebral thrombosis, cerebral embolism, transient ischemic attack, etc.), etc.] and the like.

Besides, the antibody of the present invention can be used for detecting the receptor of the present invention present in test samples such as body fluids, tissues, etc. The antibody can also be used for preparation of antibody columns used to purify the receptor of the present invention, for detection of the receptor of the present invention in each fraction upon purification, for analysis of the behavior of the receptor of the present invention in test cells; etc.

[3] Gene Diagnostic Agent

By using the polynucleotide (DNA) of the present invention, e.g., as a probe, an abnormality (gene abnormality) of the DNA or mRNA encoding the receptor of the present invention in human or other warm-blooded animal (e.g., rat, mouse, guinea pig, rabbit, fowl, sheep, swine, bovine, horse, cat, dog, monkey, etc.) can be detected. Therefore, the polynucleotide (DNA) of the present invention is useful as a gene diagnostic agent for damages to the DNA or mRNA, its mutation or decreased expression or increased expression, or overexpression of the DNA or mRNA.

The gene diagnosis described above using the DNA of the present invention can be performed by, for example, publicly known Northern hybridization or PCR-SSCP assay (Genomics, 5, 874-879 (1989); Proceedings of the National Academy of Sciences of the United States of America, 86, 2766-2770 (1989)), DNA microarray, etc.

When overexpression of the receptor of the present invention is detected, for example, the IL-13 production promoting activity, mast cell degranulation promoting activity, eicosanoid production promoting activity or mast cell growth promoting activity is enhanced. Then, it can be diagnosed that it is highly likely to suffer from diseases in the future, such as immune disorders [e.g., inflammatory diseases (pituitary tumor, thyroiditis, peritonitis, Crohn's disease, ulcerative colitis, erythema nodosum, chronic rheumatoid arthritis, systemic lupus erythematosus, etc.), allergy (e.g., allergic conjunctivitis, allergic rhinitis, pollinosis, metal allergy, etc.), asthma, exudative otitis media, Meniere's disease, contact dermatitis, anaphylaxis, urticaria, myasthenia gravis, glomerulonephritis, Sjögren's syndrome, Basedow's disease, insulin resistant diabetes, atopic dermatitis, leukocyte abnormality, etc.], respiratory disorders [e.g., chronic obstructive pulmonary disease (e.g., chronic bronchitis, pulmonary emphysema), diffuse panbronchiolitis, cystic fibrosis, hypersensitivity penumonitis, idiopathic interstitial pneumonia, pulmonary fibrosis, etc.], urinary tract disorders (e.g., renal tubulointerstitial injuries (fibrosis), interstitial cystitis, allergic cystitis, etc.), circulatory diseases (e.g., arteriosclerosis, acute coronary syndrome, atherosclerotic aortic aneurysm, cardiac anaphylaxis, heart failure, myocardial infarction, angina pectoris, arrhythmia, deep venous thrombosis, restenosis after PTCA, etc.), ophthalmic disorders (e.g., pterygium, vernal catarrh, dry eyes, etc.), cancer (e.g., papillary thyroid carcinoma, non-small cell lung cancer, endometrial cancer, cervical cancer, gastric cancer, pancreatic cancer, lung cancer, renal cancer, liver cancer, ovarian cancer, prostate cancer, bladder cancer, breast cancer, colon cancer, rectal cancer, Kaposi's sarcoma, mastocytoma, etc.), digestive disorders [e.g., chronic liver disease, food allergy, allergic enteritis, milk protein-induced proctitis, peptic ulcer (e.g., gastric ulcer, duodenal ulcer, marginal ulcer, Zollinger-Ellison syndrome, etc.), gastritis, reflux esophagitis, NUD (Non Ulcer Dyspepsia), gastric MALT lymphoma, non-steroidal anti-inflammatory drug-induced ulcer, hyperacidity, postoperative stress-induced hyperacidity and ulcer, etc.], cerebral infarction, hyperlipemia, acute renal failure, diabetes mellitus, obesity, edema, granuloma, atopic myelitis, neurofibroma, nasal mucosa hypersensitivity, Hodgkin's disease, endometrial hyperplasia, central nervous disorders [e.g., neurodegenerative disease (e.g., Alzheimer's disease (familial Alzheimer's disease, juvenile Alzheimer's disease, sporadic Alzheimer's disease, etc.), Parkinson's disease, Down's syndrome, amyotrophic lateral sclerosis, prion disease (Creutzfeldt-Jakob disease), Huntington's chorea, diabetic neuropathy, multiple sclerosis, etc.), mental disorders (e.g., schizophrenia, depression, bipolar disorders, anxiety disorders, attention deficit hyperactivity disorders, panic disorders, etc.), cerebrovascular disorders (e.g., cerebral thrombosis, cerebral embolism, transient ischemic attack, etc.), etc.] and the like.

[4] Pharmaceuticals Comprising Antisense Polynucleotide (e.g., DNA)

The antisense polynucleotide (e.g., antisense DNA) that can bind complementarily to the polynucleotide (e.g., DNA) of the present invention to suppress the expression of the polynucleotide (e.g., DNA) is useful as, e.g., an IL-13 production inhibitor, a mast cell degranulation inhibitor, an eicosanoid (e.g., leukotriene, prostaglandin, etc.) production inhibitor, a mast cell growth inhibitor, etc., for a low toxic and safe medicament such as a prophylactic/therapeutic agent for diseases such as immune disorders [e.g., inflammatory diseases (pituitary tumor, thyroiditis, peritonitis, Crohn's disease, ulcerative colitis, erythema nodosum, chronic rheumatoid arthritis, systemic lupus erythematosus, etc.), allergy (e.g., allergic conjunctivitis, allergic rhinitis, pollinosis, metal allergy, etc.), asthma, exudative otitis media, Meniere's disease, contact dermatitis, anaphylaxis, urticaria, myasthenia gravis, glomerulonephritis, Sjögren's syndrome, Basedow's disease, insulin resistant diabetes, atopic dermatitis, leukocyte abnormality, etc.], respiratory disorders [e.g., chronic obstructive pulmonary disease (e.g., chronic bronchitis, pulmonary emphysema), diffuse panbronchiolitis, cystic fibrosis, hypersensitivity penumonitis, idiopathic interstitial pneumonia, pulmonary fibrosis, etc.], urinary tract disorders (e.g., renal tubulointerstitial injuries (fibrosis), interstitial cystitis, allergic cystitis, etc.), circulatory diseases (e.g., arteriosclerosis, acute coronary syndrome, atherosclerotic aortic aneurysm, cardiac anaphylaxis, heart failure, myocardial infarction, angina pectoris, arrhythmia, deep venous thrombosis, restenosis after PTCA, etc.), ophthalmic disorders (e.g., pterygium, vernal catarrh, dry eyes, etc.), cancer (e.g., papillary thyroid carcinoma, non-small cell lung cancer, endometrial cancer, cervical cancer, gastric cancer, pancreatic cancer, lung cancer, renal cancer, liver cancer, ovarian cancer, prostate cancer, bladder cancer, breast cancer, colon cancer, rectal cancer, Kaposi's sarcoma, mastocytoma, etc.), digestive disorders [e.g., chronic liver disease, food allergy, allergic enteritis, milk protein-induced proctitis, peptic ulcer (e.g., gastric ulcer, duodenal ulcer, marginal ulcer, Zollinger-Ellison syndrome, etc.), gastritis, reflux esophagitis, NUD (Non Ulcer Dyspepsia), gastric MALT lymphoma, non-steroidal anti-inflammatory drug-induced ulcer, hyperacidity, postoperative stress-induced hyperacidity and ulcer, etc.], cerebral infarction, hyperlipemia, acute renal failure, diabetes mellitus, obesity, edema, granuloma, atopic myelitis, neurofibroma, nasal mucosa hypersensitivity, Hodgkin's disease, endometrial hyperplasia, central nervous disorders [e.g., neurodegenerative disease (e.g., Alzheimer's disease (familial Alzheimer's disease, juvenile Alzheimer's disease, sporadic Alzheimer's disease, etc.), Parkinson's disease, Down's syndrome, amyotrophic lateral sclerosis, prion disease (Creutzfeldt-Jakob disease), Huntington's chorea, diabetic neuropathy, multiple sclerosis, etc.), mental disorders (e.g., schizophrenia, depression, bipolar disorders, anxiety disorders, attention deficit hyperactivity disorders, panic disorders, etc.), cerebrovascular disorders (e.g., cerebral thrombosis, cerebral embolism, transient ischemic attack, etc.), etc.] and the like.

For example, the antisense DNA is administered solely, or the antisense DNA is inserted into an appropriate vector such as retrovirus vector, adenovirus vector, adenovirus-associated virus vector, etc., which is then administered in a conventional manner. The antisense DNA may be administered in an intact form, or may be prepared into a dosage form together with a physiologically acceptable carrier to increase its uptake and administered by gene gun or through a catheter such as a catheter with a hydrogel.

In addition, the antisense DNA may also be employed as an oligonucleotide probe for diagnosis to examine the presence of the DNA of the present invention in tissues or cells and the conditions of its expression.

As in the antisense polynucleotide described above, the double-stranded RNA [e.g., siRNA (small (short) interfering RNA), shRNA (small (short) hairpin RNA) to the receptor of the present invention] containing a part of the RNA encoding the receptor of the present invention, the ribozyme containing a part of the RNA encoding the receptor of the present invention, etc., can also suppress the expression of the polynucleotide of the present invention and can suppress the in vivo the functions of the receptor of the present invention or the polynucleotide of the present invention and thus they are useful as e.g., IL-13 production inhibitors, mast cell degranulation inhibitors, eicosanoid (e.g., leukotriene, prostaglandin, etc.) production inhibitors, mast cell growth inhibitors, etc., for low toxic and safe medicaments such as agents for the prevention/treatment of, for example, immune disorders [e.g., inflammatory diseases (pituitary tumor, thyroiditis, peritonitis, Crohn's disease, ulcerative colitis, erythema nodosum, chronic rheumatoid arthritis, systemic lupus erythematosus, etc.), allergy (e.g., allergic conjunctivitis, allergic rhinitis, pollinosis, metal allergy, etc.), asthma, exudative otitis media, Meniere's disease, contact dermatitis, anaphylaxis, urticaria, myasthenia gravis, glomerulonephritis, Sjögren's syndrome, Basedow's disease, insulin resistant diabetes, atopic dermatitis, leukocyte abnormality, etc.], respiratory disorders [e.g., chronic obstructive pulmonary disease (e.g., chronic bronchitis, pulmonary emphysema), diffuse panbronchiolitis, cystic fibrosis, hypersensitivity penumonitis, idiopathic interstitial pneumonia, pulmonary fibrosis, etc.], urinary tract disorders (e.g., renal tubulointerstitial injuries (fibrosis), interstitial cystitis, allergic cystitis, etc.), circulatory diseases (e.g., arteriosclerosis, acute coronary syndrome, atherosclerotic aortic aneurysm, cardiac anaphylaxis, heart failure, myocardial infarction, angina pectoris, arrhythmia, deep venous thrombosis, restenosis after PTCA, etc.), ophthalmic disorders (e.g., pterygium, vernal catarrh, dry eyes, etc.), cancer (e.g., papillary thyroid carcinoma, non-small cell lung cancer, endometrial cancer, cervical cancer, gastric cancer, pancreatic cancer, lung cancer, renal cancer, liver cancer, ovarian cancer, prostate cancer, bladder cancer, breast cancer, colon cancer, rectal cancer, Kaposi's sarcoma, mastocytoma, etc.), digestive disorders [e.g., chronic liver disease, food allergy, allergic enteritis, milk protein-induced proctitis, peptic ulcer (e.g., gastric ulcer, duodenal ulcer, marginal ulcer, Zollinger-Ellison syndrome, etc.), gastritis, reflux esophagitis, NUD (Non Ulcer Dyspepsia), gastric MALT lymphoma, non-steroidal anti-inflammatory drug-induced ulcer, hyperacidity, postoperative stress-induced hyperacidity and ulcer, etc.], cerebral infarction, hyperlipemia, acute renal failure, diabetes mellitus, obesity, edema, granuloma, atopic myelitis, neurofibroma, nasal mucosa hypersensitivity, Hodgkin's disease, endometrial hyperplasia, central nervous disorders [e.g., neurodegenerative disease (e.g., Alzheimer's disease (familial Alzheimer's disease, juvenile Alzheimer's disease, sporadic Alzheimer's disease, etc.), Parkinson's disease, Down's syndrome, amyotrophic lateral sclerosis, prion disease (Creutzfeldt-Jakob disease), Huntington's chorea, diabetic neuropathy, multiple sclerosis, etc.), mental disorders (e.g., schizophrenia, depression, bipolar disorders, anxiety disorders, attention deficit hyperactivity disorders, panic disorders, etc.), cerebrovascular disorders (e.g., cerebral thrombosis, cerebral embolism, transient ischemic attack, etc.), etc.] and the like.

The double-stranded RNA can be manufactured by designing the same based on the sequence of the polynucleotide of the present invention, by publicly known methods (e.g., Nature, 411, 494, 2001) with a modification.

The ribozyme can be manufactured by designing the same based on the sequence of the polynucleotide of the present invention, by a modification of publicly known methods (e.g., TRENDS in Molecular Medicine, 7, 221, 2001). For example, the ribozyme designing the same based on the sequence of the polynucleotide of the present invention, can be manufactured by ligating a publicly known ribozyme to a part of the RNA encoding the receptor of the present invention. The part of the RNA encoding the receptor of the present invention includes a contiguous part (RNA fragment) to the cleavage site on the RNA of the present invention, which can be cleaved by a publicly known ribozyme.

Where the double-stranded RNA or ribozyme described above is used as the agent for the prevention/treatment described above, the RNA or ribozyme can be prepared into pharmaceutical preparations, which are provided for administration, as in the antisense polynucleotide.

[5] Medicament Comprising the Antibody of the Present Invention

The antibody to the receptor of the present invention (e.g., an antibody having the action of neutralizing the receptor of the present invention, an antibody inactivating signal transduction, etc.) is useful as e.g., the IL-13 production inhibitor, mast cell degranulation inhibitor, eicosanoid (e.g., leukotriene, prostaglandin, etc.) production inhibitor, mast cell growth inhibitor, etc., for a low toxic and safe medicament such as an agent for the prevention/treatment of, for example, immune disorders [e.g., inflammatory diseases (pituitary tumor, thyroiditis, peritonitis, Crohn's disease, ulcerative colitis, erythema nodosum, chronic rheumatoid arthritis, systemic lupus erythematosus, etc.), allergy (e.g., allergic conjunctivitis, allergic rhinitis, pollinosis, metal allergy, etc.), asthma, exudative otitis media, Meniere's disease, contact dermatitis, anaphylaxis, urticaria, myasthenia gravis, glomerulonephritis, Sjögren's syndrome, Basedow's disease, insulin resistant diabetes, atopic dermatitis, leukocyte abnormality, etc.], respiratory disorders [e.g., chronic obstructive pulmonary disease (e.g., chronic bronchitis, pulmonary emphysema), diffuse panbronchiolitis, cystic fibrosis, hypersensitivity penumonitis, idiopathic interstitial pneumonia, pulmonary fibrosis, etc.], urinary tract disorders (e.g., renal tubulointerstitial injuries (fibrosis), interstitial cystitis, allergic cystitis, etc.), circulatory diseases (e.g., arteriosclerosis, acute coronary syndrome, atherosclerotic aortic aneurysm, cardiac anaphylaxis, heart failure, myocardial infarction, angina pectoris, arrhythmia, deep venous thrombosis, restenosis after PTCA, etc.), ophthalmic disorders (e.g., pterygium, vernal catarrh, dry eyes, etc.), cancer (e.g., papillary thyroid carcinoma, non-small cell lung cancer, endometrial cancer, cervical cancer, gastric cancer, pancreatic cancer, lung cancer, renal cancer, liver cancer, ovarian cancer, prostate cancer, bladder cancer, breast cancer, colon cancer, rectal cancer, Kaposi's sarcoma, mastocytoma, etc.), digestive disorders [e.g., chronic liver disease, food allergy, allergic enteritis, milk protein-induced proctitis, peptic ulcer (e.g., gastric ulcer, duodenal ulcer, marginal ulcer, Zollinger-Ellison syndrome, etc.), gastritis, reflux esophagitis, NUD (Non Ulcer Dyspepsia), gastric MALT lymphoma, non-steroidal anti-inflammatory drug-induced ulcer, hyperacidity, postoperative stress-induced hyperacidity and ulcer, etc.], cerebral infarction, hyperlipemia, acute renal failure, diabetes mellitus, obesity, edema, granuloma, atopic myelitis, neurofibroma, nasal mucosa hypersensitivity, Hodgkin's disease, endometrial hyperplasia, central nervous disorders [e.g., neurodegenerative disease (e.g., Alzheimer's disease (familial Alzheimer's disease, juvenile Alzheimer's disease, sporadic Alzheimer's disease, etc.), Parkinson's disease, Down's syndrome, amyotrophic lateral sclerosis, prion disease (Creutzfeldt-Jakob disease), Huntington's chorea, diabetic neuropathy, multiple sclerosis, etc.), mental disorders (e.g., schizophrenia, depression, bipolar disorders, anxiety disorders, attention deficit hyperactivity disorders, panic disorders, etc.), cerebrovascular disorders (e.g., cerebral thrombosis, cerebral embolism, transient ischemic attack, etc.), etc.] and the like.

The medicaments comprising the antibody of the present invention described above can be administered to human or other warm-blooded animal (e.g., rats, rabbits, sheep, swine, bovine, cats, dogs, monkeys, etc.) orally or parenterally, directly as a liquid preparation, or as a pharmaceutical composition in an appropriate preparation form. The dose may vary depending upon subject to be administered, target disease, conditions, route of administration, etc. For example, when the antibody of the present invention is used to treating/prevent interstitial cystitis in an adult patient, it is advantageous to administer the antibody in the form of intravenous injection normally in a single dose of about 0.01 to about 20 mg/kg body weight, preferably about 0.1 to about 10 mg/kg body weight, and more preferably about 0.1 to about 5 mg/kg body weight, approximately 1 to 5 times per day preferably approximately 1 to 3 times per day. In other parenteral administration and oral administration, the antibody can be administered in a dose corresponding to the dose given above. When the condition is especially severe, the dose may be increased according to the condition.

The antibody of the present invention may be administered directly as it is or as an appropriate pharmaceutical composition. The pharmaceutical composition used for the administration described above contains a pharmacologically acceptable carrier with the aforesaid compounds or salts thereof, a diluent or excipient. Such a composition is provided in the preparation suitable for oral or parenteral administration.

That is, examples of the composition for oral administration include solid or liquid preparations, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or an excipient conventionally used in the field of pharmaceutical preparations. Examples of the vehicle or excipient for tablets are lactose, starch, sucrose, magnesium stearate, etc.

Examples of the composition for parenteral administration are injectable preparations, suppositories, vaccine, etc. The injectable preparations may include dosage forms such as intravenous, subcutaneous, intracutaneous and intramuscular injections, drip infusions, etc. These injectable preparations may be prepared by methods publicly known. The injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mols) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule. The suppository used for rectal administration may be prepared by blending the aforesaid antibody or its salt with conventional bases for suppositories.

Advantageously, the pharmaceutical compositions for oral or parenteral use described above are prepared into pharmaceutical preparations in a unit dose suited to fit a dose of the active ingredients. Such unit dose preparations include, for example, tablets, pills, capsules, injections (ampoules), suppositories, etc. The amount of the aforesaid antibody contained is generally about 5 to 500 mg per dosage unit form; especially in the form of injection, it is preferred that the aforesaid antibody is contained in about 5 to 100 mg and in about 10 to 250 mg for the other forms.

Each composition described above may further contain other active components unless formulation causes any adverse interaction with the antibody described above.

[6] DNA Transgenic Animal

The present invention provides a non-human mammal bearing DNA encoding the receptor of the present invention, which is exogenous (hereinafter abbreviated as the exogenous DNA of the present invention) or its variant DNA (sometimes simply referred to as the exogenous variant DNA of the present invention).

That is, the present invention provides:
(1) a non-human mammal bearing the exogenous DNA of the present invention or its variant DNA;
(2) the mammal according to (1), wherein the non-human mammal is a rodent;
(3) the mammal according to (2), wherein the rodent is mouse or rat; and,
(4) a recombinant vector containing the exogenous DNA of the present invention or its variant DNA and capable of expressing in a mammal; etc.

The non-human mammal bearing the exogenous DNA of the present invention or its variant DNA (hereinafter simply referred to as the DNA transgenic animal of the present invention) can be prepared by transfecting a desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase), by standard means, such as the calcium phosphate method, the electric pulse method, the lipofection method, the agglutination method, the microinjection method, the particle gun method, the DEAE-dextran method, etc. Also, it is possible to transfect the exogenous DNA of the present invention into a somatic cell, a living organ, a tissue cell, or the like by the DNA transfection methods, and utilize the transformant for cell culture, tissue culture, etc. In addition, these cells may be fused with the above-described germinal cell by a publicly known cell fusion method to prepare the DNA transgenic animal of the present invention.

Examples of the non-human mammal that can be used include bovine, swine, sheep, goat, rabbits, dogs, cats, guinea pigs, hamsters, mice, rats, etc. Above all, preferred are rodents, especially mice (e.g., C57B1/6 strain, DBA2 strain, etc. for a pure line and for a cross line, B6C3F$_1$ strain, BDF$_1$ strain B6D2F, strain, BALB/c strain, ICR strain, etc.), rats (Wistar, SD, etc.) or the like, since they are relatively short in ontogeny and life cycle from a standpoint of creating model animals for disease.

"Mammals" in a recombinant vector that can be expressed in the mammals include the aforesaid non-human mammals, human, etc.

The exogenous DNA of the present invention refers to the DNA of the present invention that is once isolated/extracted from mammals, not the DNA of the present invention inherently possessed by the non-human mammals.

The mutant DNA of the present invention includes mutants resulting from variation (e.g., mutation, etc.) in the base sequence of the original DNA of the present invention, specifically DNAs resulting from base addition, deletion, substitution with other bases, etc. and further including abnormal DNA.

The abnormal DNA is intended to mean such a DNA that expresses the receptor of the present invention which is abnormal and exemplified by the DNA, etc. that expresses a polypeptide to suppress the functions of the receptor of the present invention which is normal.

The exogenous DNA of the present invention may be any one of those derived from a mammal of the same species as, or a different species from, the mammal as the target animal. In transfecting the DNA of the present invention into the target animal, it is generally advantageous to use the DNA as a DNA construct in which the DNA is ligated downstream a promoter capable of expressing the DNA in the target animal. For example, in the case of transfecting the human DNA of the present invention, a DNA transgenic mammal that expresses the DNA of the present invention to a high level, can be prepared by microinjecting a DNA construct (e.g., vector, etc.) ligated with the human DNA of the present invention into a fertilized egg of the target mammal, e.g., a mouse fertilized egg, downstream various promoters which are capable of expressing the DNA derived from various mammals (e.g., rabbits, dogs, cats, guinea pigs, hamsters, rats, mice, etc.) bearing the DNA of the present invention highly homologous to the human DNA.

As expression vectors for the receptor of the present invention, there are *Escherichia coli*-derived plasmids, *Bacillus subtilis*-derived plasmids, yeast-derived plasmids, bacteriophages such as λ phage, retroviruses such as Moloney leukemia virus, etc., and animal viruses such as vaccinia virus, baculovirus, etc. Of these vectors, *Escherichia coli*-derived plasmids, *Bacillus subtilis*-derived plasmids, or yeast-derived plasmids, etc. are preferably used.

Examples of these promoters for regulating the DNA expression described above include (i) promoters for DNA derived from viruses (e.g., simian virus, cytomegalovirus, Moloney leukemia virus, JC virus, breast cancer virus, poliovirus, etc.), and (ii) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein, glutathione S-transferase, platelet-derived growth factor β, keratins K1, K10 and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na,K-ATPase), neurofilament light chain, metallothioneins I and IIA, metalloproteinase I tissue inhibitor, MHC class I antigen (H-2L), H-ras, renin, dopamine β-hydroxylase, thyroid peroxidase (TPO), polypeptide chain elongation factor 1α (EF-1α), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle a actin, preproencephalin A, vasopressin, etc. Among them, cytomegalovirus promoters, human polypeptide elongation factor 1α (EF-1α) promoters, human and fowl β actin promoters, etc., which are capable of high expression in the whole body are preferred.

Preferably, the vectors described above have a sequence that terminates the transcription of the desired messenger RNA in the DNA transgenic animal (generally termed a terminator); for example, a sequence of each DNA derived from viruses and various mammals, and SV40 terminator of the simian virus and the like are preferably used.

In addition, for the purpose of enhancing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The translational region for the normal receptor of the present invention can be obtained using as a starting material the entire genomic DNA or its portion of liver, kidney, thyroid cell or fibroblast origin from human or various mammals (e.g., rabbits, dogs, cats, guinea pigs, hamsters, rats, mice, etc.) or of various commercially available genomic DNA libraries, or using cDNA prepared by a publicly known method from RNA of liver, kidney, thyroid cell or fibroblast origin as a starting material. Also, an exogenous abnormal DNA can produce the translational region through variation of the translational region of normal polypeptide obtained from the cells or tissues described above by point mutagenesis.

The translational region can be prepared by a conventional DNA engineering technique, in which the DNA is ligated downstream the aforesaid promoter and if desired, upstream the translation termination site, as a DNA construct capable of being expressed in the transgenic animal.

The exogenous DNA of the present invention is transfected at the fertilized egg cell stage in a manner such that the DNA is certainly present in all the germinal cells and somatic cells of the target mammal. The fact that the exogenous DNA of the present invention is present in the germinal cells of the animal prepared by DNA transfection means that all offspring of the prepared animal will maintain the exogenous DNA of the present invention in all of the germinal cells and somatic cells thereof. The offspring of the animal that inherits the exogenous DNA of the present invention also have the exogenous DNA of the present invention in all of the germinal cells and somatic cells thereof.

The non-human mammal in which the normal exogenous DNA of the present invention has been transfected can be passaged as the DNA-bearing animal under ordinary rearing environment, by confirming that the exogenous DNA is stably retained by crossing.

By the transfection of the exogenous DNA of the present invention at the fertilized egg cell stage, the DNA is retained to be excess in all of the germinal and somatic cells. The fact that the exogenous DNA of the present invention is excessively present in the germinal cells of the prepared animal after transfection means that the DNA of the present invention is excessively present in all of the germinal cells and somatic cells thereof. The offspring of the animal that inherits the exogenous DNA of the present invention have excessively the DNA of the present invention in all of the germinal cells and somatic cells thereof.

It is possible to obtain homozygotic animals having the transfected DNA in both homologous chromosomes and breed male and female of the animal so that all the progeny have this DNA in excess.

In a non-human mammal bearing the normal DNA of the present invention, the normal DNA of the present invention has expressed at a high level, and may eventually develop hyperfunction in the function of the receptor of the present invention by accelerating the function of endogenous normal DNA. Therefore, the animal can be utilized as a pathologic model animal for such a disease. For example, using the normal DNA transgenic animal of the present invention, it is possible to elucidate the mechanism of hyperfunction in the function of the receptor of the present invention and the pathological mechanism of the disease associated with the receptor of the present invention and to investigate how to treat these diseases.

Furthermore, a mammal transfected with the exogenous normal DNA of the present invention exhibits an increasing symptom of the receptor of the present invention librated, and can be used as, e.g., the IL-13 production inhibitor, mast cell degranulation inhibitor, eicosanoid (e.g., leukotriene, prostaglandin, etc.) production inhibitor, mast cell growth inhibitor, etc., in screening tests of agents for the prevention/treatment of, for example, immune disorders [e.g., inflammatory diseases (pituitary tumor, thyroiditis, peritonitis, Crohn's disease, ulcerative colitis, erythema nodosum, chronic rheumatoid arthritis, systemic lupus erythematosus, etc.), allergy (e.g., allergic conjunctivitis, allergic rhinitis, pollinosis, metal allergy, etc.), asthma, exudative otitis media, Meniere's disease, contact dermatitis, anaphylaxis, urticaria, myasthenia gravis, glomerulonephritis, Sjögren's syndrome, Basedow's disease, insulin resistant diabetes, atopic dermatitis, leukocyte abnormality, etc.], respiratory disorders [e.g., chronic obstructive pulmonary disease (e.g., chronic bronchitis, pulmonary emphysema), diffuse panbronchiolitis, cystic fibrosis, hypersensitivity penumonitis, idiopathic interstitial pneumonia, pulmonary fibrosis, etc.], urinary tract disorders (e.g., renal tubulointerstitial injuries (fibrosis), interstitial cystitis, allergic cystitis, etc.), circulatory diseases (e.g., arteriosclerosis, acute coronary syndrome, atherosclerotic aortic aneurysm, cardiac anaphylaxis, heart failure, myocardial infarction, angina pectoris, arrhythmia, deep venous thrombosis, restenosis after PTCA, etc.), ophthalmic disorders (e.g., pterygium, vernal catarrh, dry eyes, etc.), cancer (e.g., papillary thyroid carcinoma, non-small cell lung cancer, endometrial cancer, cervical cancer, gastric cancer, pancreatic cancer, lung cancer, renal cancer, liver cancer, ovarian cancer, prostate cancer, bladder cancer, breast cancer, colon cancer, rectal cancer, Kaposi's sarcoma, mastocytoma, etc.), digestive disorders [e.g., chronic liver disease, food allergy, allergic enteritis, milk protein-induced proctitis, peptic ulcer (e.g., gastric ulcer, duodenal ulcer, marginal ulcer, Zollinger-Ellison syndrome, etc.), gastritis, reflux esophagitis, NUD (Non Ulcer Dyspepsia), gastric MALT lymphoma, non-steroidal anti-inflammatory drug-induced ulcer, hyperacidity, postoperative stress-induced hyperacidity and ulcer, etc.], cerebral infarction, hyperlipemia, acute renal failure, diabetes mellitus, obesity, edema, granuloma, atopic myelitis, neurofibroma, nasal mucosa hypersensitivity, Hodgkin's disease, endometrial hyperplasia, central nervous disorders [e.g., neurodegenerative disease (e.g., Alzheimer's disease (familial Alzheimer's disease, juvenile Alzheimer's disease, sporadic Alzheimer's disease, etc.), Parkinson's disease, Down's syndrome, amyotrophic lateral sclerosis, prion disease (Creutzfeldt-Jakob disease), Huntington's chorea, diabetic neuropathy, multiple sclerosis, etc.), mental disorders (e.g., schizophrenia, depression, bipolar disorders, anxiety disorders, attention deficit hyperactivity disorders, panic disorders, etc.), cerebrovascular disorders (e.g., cerebral thrombosis, cerebral embolism, transient ischemic attack, etc.), etc.] and the like.

On the other hand, a non-human mammal having the exogenous abnormal DNA of the present invention can be passaged under normal breeding conditions as the DNA-bearing animal by confirming stable retention of the exogenous DNA via crossing. Furthermore, the exogenous DNA of interest can be utilized as a starting material by inserting the DNA into the plasmid described above. The DNA construct with a promoter can be prepared by conventional DNA engineering techniques. The transfection of the abnormal DNA of the present invention at the fertilized egg cell stage is preserved to be present in all of the germinal and somatic cells of the target mammal. The fact that the abnormal DNA of the present invention is present in the germinal cells of the animal after DNA transfection means that all of the offspring of the prepared animal have the abnormal DNA of the present invention in all of the germinal and somatic cells. Such an offspring that passaged the exogenous DNA of the present invention will have the abnormal DNA of the present invention in all of the germinal and somatic cells. A homozygous animal having the introduced DNA on both of homologous chromosomes can be acquired, and by crossing these male and female animals, all the offspring can be bred to retain the DNA.

In a non-human mammal bearing the abnormal DNA of the present invention, the abnormal DNA of the present invention has expressed to a high level, and may eventually develop the function inactive type inadaptability to the receptor of the present invention by inhibiting the functions of endogenous normal DNA. Therefore, the animal can be utilized as a pathologic model animal for such a disease. For example, using the abnormal DNA transgenic animal of the present invention, it is possible to elucidate the mechanism of the function inactive type inadaptability to the receptor of the present invention and to investigate how to treat the disease.

More specifically, the transgenic animal of the present invention expressing the abnormal DNA of the present invention at a high level is expected to serve as an experimental model to elucidate the mechanism of the functional inhibition (dominant negative effect) of a normal polypeptide or receptor by the abnormal polypeptide of the present invention or receptor of the present invention in the function inactive type inadaptability of the receptor of the present invention.

A mammal bearing the abnormal exogenous DNA of the present invention is also expected to serve for screening a candidate drug for the treatment of the function inactive type inadaptability to the receptor of the present invention, since the receptor of the present invention is increased in such an animal in its free form.

Other potential applications of two kinds of the DNA transgenic animals of the present invention described above further include:
(i) use as a cell source for tissue culture;
(ii) elucidation of the relation to a polypeptide or a receptor that is specifically expressed or activated by the receptor of the present invention, by direct analysis of DNA or RNA in tissues of the DNA transgenic animal of the present invention or by analysis of the polypeptide or receptor tissues expressed by the DNA;
(iii) research on the function of cells derived from tissues that are usually cultured only with difficulty, using cells in tissues bearing the DNA cultured by a standard tissue culture technique;
(iv) screening of a drug that enhances the functions of cells using the cells described in (iii) above; and,
(v) isolation and purification of the variant polypeptide or the receptor of the present invention and preparation of an antibody thereto; etc.

Furthermore, clinical conditions of a disease associated with the receptor of the present invention [neurodegenerative disease (e.g., Alzheimer's disease, Parkinson's disease, Down's syndrome, amyotrophic lateral sclerosis, prion disease, Creutzfeldt-Jakob disease, Huntington's chorea, diabetic neuropathy, multiple sclerosis, malignant schwannoma, etc.), etc.], including the function inactive type inadaptability to the receptor of the present invention can be determined by using the DNA transgenic animal of the present invention. Also, pathological findings on each organ in a disease model associated with the receptor of the present invention can be obtained in more detail, leading to the development of a new method for treatment as well as the research and therapy of any secondary diseases associated with the disease.

It is also possible to obtain a free DNA-transfected cell by withdrawing each organ from the DNA transgenic animal of the present invention, mincing the organ and degrading with a proteinase such as trypsin, etc., followed by establishing the line of culturing or cultured cells. Furthermore, the DNA transgenic animal of the present invention can serve to identify cells capable of producing the receptor of the present invention, and to study in association with apoptosis, differentiation or proliferation or on the mechanism of signal transduction in these properties to inspect any abnormality therein. Accordingly, the DNA transgenic animal can provide an effective research material to elucidate the receptor of the present invention and its function and effect.

To develop a drug for the treatment of diseases associated with the receptor of the present invention, including the function inactive type inadaptability to the receptor of the present invention, using the DNA transgenic animal of the present invention, an effective and rapid method for screening can be provided by using the method for inspection and the method for quantification, etc. described above. It is also possible to investigate and develop a method for DNA therapy for the treatment of diseases associated with the receptor of the present invention, using the DNA transgenic animal of the present invention or a vector capable of expressing the exogenous DNA of the present invention.

In the specification and drawings, the codes of bases, amino acids, etc. are denoted in accordance with the IUPAC-IUB Commission on Biochemical Nomenclature or by the common codes in the art, examples of which are shown below. For amino acids that may have the optical isomer, L form is presented unless otherwise indicated.
DNA: deoxyribonucleic acid
cDNA: complementary deoxyribonucleic acid
A: adenine
T: thymine
G: guanine
C: cytosine
I: inosine
RNA: ribonucleic acid
mRNA: messenger ribonucleic acid
DATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediaminetetraacetic acid
SDS: sodium dodecyl sulfate
BHA: benzhydrylamine pMBHA: p-methyobenzhydrylamine
Tos: p-toluenesulfonyl
Bzl: benzyl
Bom: benzyloxymethyl
Boc: t-butoxycarbonyl
DCM: dichloromethane
HOBt: 1-hydroxybenztriazole
DCC: N,N'-dicyclohexylcarbodiimido
TFA: trifluoroacetic acid
DIEA: diisopropylethylamine
Gly or G: glycine
Ala or A: alanine
Val or V: valine
Leu or L: leucine
Ile or I: isoleucine
Ser or S: serine
Thr or T: threonine
Cys or C: cysteine
Met or M: methionine
Glu or E: glutamic acid
Asp or D: aspartic acid
Lys or K: lysine
Arg or R: arginine
H is or H: histidine
Phe or F: phenylalanine
Tyr or Y: tyrosine
Trp or W: tryptophan
Pro or P: proline
Asn or N: asparagine
Gln or Q: glutamine
pGlu: pyroglutamic acid
Tyr(I): 3-iodotyrosine
DMF: N,N-dimethylformamide
Fmoc: N-9-fluorenyl methoxycarbonyl
Trt: trityl
Pbf: 2,2,4,6,7-pentamethyldihydrobenzofuran-5-sulfonyl
Cit: 2-chlorotrityl
But: t-butyl
Met(O): methionine sulfoxide
DNP: dinitrophenol The sequence identification numbers in the sequence listing of the specification indicate the following sequences.

[SEQ ID NO: 1]
This shows the amino acid sequence of human GPR34.
[SEQ ID NO: 2]
This shows the base sequence of cDNA encoding human GPR34.
[SEQ ID NO: 3]
This shows the base sequence of primer 1 used for PCR in REFERENCE EXAMPLE 1 (1-1) below.
[SEQ ID NO: 4]
This shows the base sequence of primer 2 used for PCR in REFERENCE EXAMPLE 1 (1-1) below.
[SEQ ID NO: 5]
This shows the base sequence of primer 3 used for PCR in REFERENCE EXAMPLE 1 (1-3) below.
[SEQ ID NO: 6]
This shows the base sequence of primer 4 used for PCR in REFERENCE EXAMPLE 1 (1-3) below.
[SEQ ID NO: 7]
This shows the base sequence of the probe used for PCR in REFERENCE EXAMPLE 1 (1-3) below. FAM (6-carboxy-fluorescein) was labeled at the 5' end as a reporter dye and TAMPA (6-carboxy-tetramethyl-rhodamine) at the 3' end as a quencher.
[SEQ ID NO: 8]
This shows the base sequence of primer 1 used for PCR in REFERENCE EXAMPLE 2 below.
[SEQ ID NO: 9]
This shows the base sequence of primer 2 used for PCR in REFERENCE EXAMPLE 2 below.
[SEQ ID NO: 10]
This shows the base sequence of cDNA fragment encoding a part of rat GPR34.
[SEQ ID NO: 11]
This shows the base sequence of primer 1 used for PCR in REFERENCE EXAMPLE 3 below.
[SEQ ID NO: 12]
This shows the base sequence of primer 2 used for PCR in REFERENCE EXAMPLE 3 below.
[SEQ ID NO: 13]
This shows the base sequence in the 3'-end partial sequence of cDNA encoding rat GPR34.
[SEQ ID NO: 14]
This shows the base sequence of primer 1 used for PCR in REFERENCE EXAMPLE 4 below.
[SEQ ID NO:15]
This shows the base sequence of primer 2 used for PCR in REFERENCE EXAMPLE 4 below.
[SEQ ID NO: 16]
This shows the base sequence in the 5'-end partial sequence of cDNA encoding rat GPR34.
[SEQ ID NO: 17]
This shows the base sequence of primer 1 used for PCR in REFERENCE EXAMPLE 5 below.
[SEQ ID NO: 18]
This shows the base sequence of primer 2 used for PCR in EXAMPLE 5 below.
[SEQ ID NO: 19]
This represents the amino acid sequence of rat GPR34.
[SEQ ID NO: 20]
This shows the base sequence of cDNA encoding rat GPR34.
[SEQ ID NO: 21]
This shows the base sequence of cDNA encoding rat GPR34 obtained in Example 5.
[SEQ ID NO: 22]
This represents the amino acid sequence of mouse GPR34. (Accession No. AAD50550) [SEQ ID NO: 23]
This shows the base sequence of cDNA encoding mouse GPR34. (Accession No. AF081916) [SEQ ID NO: 24]
This shows the base sequence of primer rIL-13-tF used for PCR in EXAMPLE 1 below.
[SEQ ID NO: 25]
This shows the base sequence of primer rIL-13-tR used for PCR in EXAMPLE 1 below.
[SEQ ID NO: 26]
This shows the base sequence of probe rIL-13-tP used for PCR used in EXAMPLE 1 below. FAM (6-carboxy-fluorescein) was labeled at the 5' end as a reporter dye and TAMRA (6-carboxy-tetramethyl-rhodamine) at the 3' end as a quencher.
[SEQ ID NO: 27]
This shows the base sequence of rIL-13 standard used for PCR in EXAMPLE 1 below.
[SEQ ID NO: 28]
This shows the base sequence of rGAPDH standard used for PCR in EXAMPLE 1 described below; [SEQ ID NO: 29]
This shows the base sequence of primer 1 used for PCR in EXAMPLE 2 below.

[SEQ ID NO: 30]

This shows the base sequence of primer 2 used for PCR in EXAMPLE 2 below.

[SEQ ID NO: 31]

This represents the amino acid sequence of guinea pig GPR34.

[SEQ ID NO: 32]

This shows the base sequence of cDNA encoding guinea pig GPR34.

[SEQ ID NO: 33]

This shows the base sequence of primer 1 used for PCR in EXAMPLE 3 below.

[SEQ ID NO: 34]

This shows the base sequence of primer 1 used for PCR in EXAMPLE 3 below.

[SEQ ID NO: 35]

This shows the amino acid sequence of cynomolgus monkey GPR34.

[SEQ ID NO: 36]

This shows the base sequence of cDNA encoding cynomolgus monkey GPR34.

[SEQ ID NO: 37]

This shows the base sequence of primer 1 used for PCR in EXAMPLE 4, EXAMPLE 5 and EXAMPLE 13 below.

[SEQ ID NO: 38]

This shows the base sequence of primer 2 used for PCR in EXAMPLES 4 and 13 below.

[SEQ ID NO: 39]

This shows the base sequence of TaqMan probe used for PCR in EXAMPLES 4, 5 and 13 below. FAM (6-carboxy-fluorescein) was labeled at the 5' end as a reporter dye and TAMRA (6-carboxy-tetramethyl-rhodamine) at the 3' end as a quencher.

[SEQ ID NO: 40]

This shows the base sequence of primer 4 used for PCR in EXAMPLE 4 below.

[SEQ ID NO: 41]

This shows the base sequence of primer 1 used for PCR in EXAMPLE 9 below.

[SEQ ID NO: 42]

This shows the base sequence of primer 2 used for PCR in EXAMPLE 9 below.

[SEQ ID NO: 43]

This shows the base sequence of the probe used for PCR in EXAMPLE 9 below. FAM (6-carboxy-fluorescein) was labeled at the 5' end as a reporter dye and TAMRA (6-carboxy-tetramethyl-rhodamine) at the 3' end as a quencher.

[SEQ ID NO: 44]

This shows the base sequence of primer rIL-6-tF for rat IL-6 quantification used for PCR in EXAMPLE 15 below.

[SEQ ID NO: 45]

This shows the base sequence of primer rIL-6-tR for rat IL-6 quantification used for PCR in EXAMPLE 15 below.

[SEQ ID NO: 46]

This shows the base sequence of probe rIL-6-tP for rat IL-6 quantification used for PCR in EXAMPLE 15 below. FAM (6-carboxy-fluorescein) was labeled at the 5' end as a reporter dye and TAMRA (6-carboxy-tetramethyl-rhodamine) at the 3' end as a quencher.

[SEQ ID NO: 47]

This shows the base sequence of rIL-6 standard for rat IL-6 quantification used for PCR in EXAMPLE 15 below.

[SEQ ID NO: 48]

This shows the base sequence of primer rTNF-α-tF for rat TNF-α quantification used for PCR in EXAMPLE 15 below.

[SEQ ID NO: 49]

This shows the base sequence of primer rTNF-α-tR for rat TNF-α quantification used for PCR in EXAMPLE 15 below.

[SEQ ID NO: 50]

This shows the base sequence of probe rTNF-α-tP for rat TNF-α quantification used for PCR in EXAMPLE 15 below. FAM (6-carboxy-fluorescein) was labeled at the 5' end as a reporter dye and TAMRA (6-carboxy-tetramethyl-rhodamine) at the 3' end as a quencher.

[SEQ ID NO: 51]

This shows the base sequence of standard for rat TNF-α quantification used for PCR in EXAMPLE 15 below.

[SEQ ID NO: 52]

This shows the base sequence of primer rIL-10-tF for rat IL-10 quantification used for PCR in EXAMPLE 15 below.

[SEQ ID NO: 53]

This shows the base sequence of primer rIL-10-tR for rat IL-10 quantification used for PCR in EXAMPLE 15 below.

[SEQ ID NO: 54]

This shows the base sequence of probe rIL-10-tP for rat IL-10 quantification used for PCR in EXAMPLE 15 below. FAM (6-carboxy-fluorescein) was labeled at the 5' end as a reporter dye and TAMRA (6-carboxy-tetramethyl-rhodamine) at the 3' end as a quencher.

[SEQ ID NO: 55]

This shows the base sequence of standard for rat IL-13 quantification used for PCR in EXAMPLE 15 below.

The present invention will be described below in more detail with reference to EXAMPLES and REFERENCE EXAMPLES, but the scope of the present invention is not deemed to be limited thereto.

Reagents used are those manufactured by Wako Pure Chemical Industries, Ltd., unless otherwise indicated. Centrifugation was performed at 4° C., unless otherwise indicated. Wistar rats (male, 12 weeks old) were purchased from Japan SLC, Inc.

EXAMPLE 1

Expression-Enhancing Action of IL-13 on Rat Peritoneal Mast Cells by lysoPS

Rat peritoneal mast cells (hereinafter RPMC) were prepared as follows. Ice-chilled mast cell medium (hereinafter MCM; 150 mM NaCl, 3.7 mM KCl, 3.0 mM NaH$_2$PO$_4$, 3.5 mM KH$_2$PO$_4$, 5.6 mM (D)-Glucose, 0.1% bovine serum albumin (hereinafter BSA), 0.1% gelatin, 10 U/ml heparin, pH 6.8) was injected into the peritoneal cavity in about 40 ml/animal. After some massage of the rat abdominal region for about 2 minutes, the peritoneal cavity was opened along the median line to drain the ascitic fluid. The ascetic fluid prepared was filtered through a cell strainer (Becton Dickinson) and centrifuged at 50×g for 7 minutes. The cells precipitated were suspended in MCM and centrifuged again at 50×g for 7 minutes. After the precipitated cells were resuspended in MCM, the suspension was layered on 2 ml of 32% (w/v) BSA solution (dissolved in 0.9% NaCl), which was allowed to stand at room temperature for 20 minutes. After centrifugation was conducted at ×300 g for 15 minutes at room temperature, the cells in the interphase between MCM and BSA solution were discarded and the precipitated cells were suspended in MCM. The suspension was centrifuged at ×300 g for 5 minutes to wash the cells twice. The precipitated cells were suspended in assay buffer (RPMI 1640 medium (Invitrogen), 0.1% BSA) and the cells were provided for the following experiment. When a part of the thus prepared cells was taken and stained in an Alcian blue solution, 95% of the cells or more were found to be RPMC. RPMC was activated as follows. RPMC was suspended in assay buffer and 10 μg/ml of monoclonal mouse antibody DNP-IgE (Yamasa) was added thereto. The mixture was allowed to stand for 30 minutes on ice for passive sensitization. After centrifugation at ×300 g for 5 minutes, the precipitated cells were washed 3 times with assay buffer. RPMC suspended in assay buffer was dispensed into a 96 well V-bottomed plate in $2 \times 10^5$/well. The assay was performed at n=3 under the respective reaction conditions. After a plate was kept warm at 37° C. for 5 minutes, lysoPS (Sigma) of 3 μM in a final concentration or DNP-BSA (Carbiochem) of 100 ng/ml in a final concentration was added depending on the assay conditions and the plate was allowed to stand at 37° C. in a 5% $CO_2$ incubator. The plate was ice-cooled 2, 4, 6 and 8 hours after to terminate the activation of RPMC. Centrifugation was performed at ×300 g for 5 minutes and the total RNA was extracted from the cells precipitated using RNeasy Mini Kit (Qiagen) in accordance with the protocol attached. The obtained total RNA was concentrated and dissolved in RNase-free $H_2O$ in accordance with the protocol attached. Next, using 250 ng of the total RNA, reverse transcription was performed by the following procedure using SuperScript II ReverseTranscriptase (Invitrogen) to prepare single-stranded cDNA. After 0.5 μg of Oligo (dT) 12-18 primer (Invitrogen) and 1 μl of 10 mM dNTP (Invitrogen) were added to the total RNA solution and then RNase-free $H_2O$ was added to make the whole volume 12 μl, incubation was performed at 70° C. for 10 minutes followed by ice cooling for a minute. After adding 4 μl of 5× First-Strand Buffer (attached to SuperScript II ReverseTranscriptase), 2 μl of 0.1M DTT (attached to SuperScript II ReverseTranscriptase), 1 μl of RNaseOUT (Invitrogen) and 1 μl of SuperScript II ReverseTranscriptase, incubation was performed at 42° C. for 50 minutes and then at 70° C. for 15 minutes, followed by ice cooling for 5 minutes. The thus prepared cDNA was purified using Ethachinmate in accordance with the protocol attached and dissolved in Tris-EDTA Buffer (Fluka).

In TaqMan PCR below, rIL-13-tF (SEQ ID NO: 24) and rIL-13-tR (SEQ ID NO: 25) were used as primers and rIL-13-tP (SEQ ID NO: 26) as a probe for quantification of rat IL-13 (interleukin-13) and rIL-13 standard (SEQ ID NO: 27) was used as a standard. TaqMan Rodent GAPDH Control Reagents VIC Probe (Applied Biosystems) were used as primers and a probe for quantification of GAPDH, and rGAPDH standard (SEQ ID NO: 28) was used as a standard.

TaqMan PCR was performed on each sample at n=2 in a volume of 25 μl using 2.5 ng of the total RNA as a template. The reaction solution was composed of 900 nM primers, 250 nM probe and ½ volume (equivalent to 100 ng of template RNA) of TaqMan Universal PCR Master Mix (Applied Systems). The reaction and analysis were performed using ABI PRISM 7700 Sequence Detection System (Applied Systems). The reaction was carried out, after maintaining at 50° C. for 2 minutes and then at 95° C. for 10 minutes, by repeating 40 times the cycle set to include 95° C. for 15 seconds and 60° C. for 1 minute. The gene expression level was determined by analysis of a standard curve to set Y-Slope at 38.5-41.5 and correlation coefficients at 0.995 or more.

The results are shown in FIG. 1.

Based on the results, the expression level of IL-13 was not changed without any stimulation or when stimulated by the antigen alone, but a marked increase in expression was observed when stimulated by the antigen+lysoPS. When stimulated by the antigen+lysoPS, the expression level of IL-13 was, after GAPDH correction, about 27 times higher compared to the level without any stimulation and about 36 times when stimulated by the antigen alone, 4 hours after the stimulation, whereas 6 after the stimulation, the expression level of IL-13 was about 13 times higher compared to the level without any stimulation and about 19 times when stimulated by the antigen alone. Further when stimulated by the antigen+lysoPS, the expression level of IL-13 was, after GAPDH correction, about 13 times higher compared to the level without any stimulation and about 27 times when stimulated by the antigen alone, 8 hours after the stimulation.

EXAMPLE 2

Cloning of cDNA Fragment Encoding the Full-Length Guinea Pig G Protein Coupled Receptor Protein GPR34

After 45 ml of mast cell medium (150 mM NaCl, 3.7 mM KCl, 3.0 mM disodium phosphate, 3.5 mM monopotassium phosphate, 5.6 mM glucose, 0.1% gelatin and 0.1% bovine serum albumin, pH 6.8) was intraperitoneally injected to 5 male guinea pigs (Hartley) of 10 weeks old, the peritoneal exudate cells were recovered. While the cell fraction was kept warm in Petri dish at 37° C. for an hour, total RNA was prepared from macrophages adhered and 1 μg of the total RNA was reverse transcribed using random 9mer according to the protocol of SuperScript II ReverseTranscriptase. The reaction was carried out at temperatures of 30° C. for 10 minutes, 42° C. for 60 minutes, 51° C. for 30 minutes and 70° C. for 15 minutes.

To acquire cDNA encoding a portion of guinea pig GPR34, primer 1 (SEQ ID NO: 29) and primer 2 (SEQ ID NO: 30) were designed based on the base sequence of mouse GPR34 and PCR was carried out. PCR was carried out in a volume of 20 μl using as a template the reverse-transcribed cDNA in the amount equivalent to 10 ng of the total RNA. The reaction solution was prepared by adding 0.5 μM of the primers, 0.2 mM dNTP and 0.5 units of Z-Taq (Takara) to the buffer attached. For amplification, after the mixture was kept at 94° C. for 2 minutes, the reaction was performed by repeating 35 times the cycle set to include 98° C. for 1 second, 55° C. for 15 seconds and 72° C. for 15 seconds. Thereafter, the mixture was kept at 72° C. for 10 minutes. The reaction product was electrophoresed through 1.2% Seakem GTG Agarose (Takara Shuzo). The band around 1400 bp, which was observed when stained with ethidium bromide, was extracted using a GeneClean Spin kit (BIO 101), subcloned into plasmid vector pCR4-TOPO using a TOPO TA cloning kit for sequencing (Invitrogen) and then transfected to *Escherichia coli* TOP10. The plasmid DNA was purified from the resulting transformants using QIAwell 8 Ultra Plasmid Kit (Qiagen). The reaction for base sequencing was carried out using BigDye Terminator Cycle Sequence Ready Reaction Kit (Perkinson Elmer), followed by analysis using ABI PRISM 377 fluorescent automated sequencer.

As a result, the base sequence (SEQ ID NO: 32) encoding guinea pig GPR34 (SEQ ID NO: 31) was contained. Using the plasmid described above, *Escherichia coli* TOP10 was transfected to give *Escherichia coli* TOP10/pcr-4-caviaGPR34. The homology in amino acid sequence was 90.2% between guinea pig GPR34 and human GPR34.

EXAMPLE 3

Cloning of cDNA Fragment Encoding the Full-Length of Cynomolgus Monkey-Derived G Protein Coupled Receptor Protein Gpr34

PolyA+ RNA was prepared from the hypothalamus of cynomolgus monkey following the protocol of ISOGEN (Nippon Gene), and 2 µg was reverse transcribed using random 9mer in accordance with the protocol of SuperScript II ReverseTranscriptase. The reaction was carried out at 30° C. for 10 minutes, 42° C. for 60 minutes, 51° C. for 30 minutes and 70° C. for 15 minutes. To acquire cDNA encoding a portion of cynomolgus monkey GPR34, primer 1 (SEQ ID NO: 33) and primer 2 (SEQ ID NO: 34) were designed based on the base sequence of human GPR34 and PCR was carried out. PCR was carried out in a volume of 20 µl using as a template the reverse-transcribed cDNA in the amount equivalent to 10 ng of polyA+ RNA. The reaction solution was prepared by adding 0.5 µM each of the primers, 0.2 mM dNTP and 0.5 units of Z-Taq (Takara) to the buffer attached. For amplification, after the mixture was kept at 94° C. for 2 minutes, the reaction was performed by repeating 35 times the cycle set to include 98° C. for 1 second, 55° C. for 15 seconds and 72° C. for 15 seconds. Thereafter, the mixture was kept at 72° C. for 10 minutes. The reaction product was electrophoresed through 1.2% Seakem GTG Agarose (Takara Shuzo). The band around 1200 bp, which was observed when stained with ethidium bromide, was extracted using a GeneClean Spin kit (BIO 101), subcloned into plasmid vector pCR4-TOPO using a TOPO TA cloning kit for sequencing (Invitrogen) and then transfected to Escherichia coli TOP10. The plasmid DNA was purified from the resulting transformants using QIAwell 8 Ultra Plasmid Kit (Qiagen). The reaction for base sequencing was carried out using BigDye Terminator Cycle Sequence Ready Reaction Kit (Perkinson Elmer), followed by analysis using ABI PRISM 377 fluorescent automated sequencer. As a result, the base sequence (SEQ ID NO: 36) encoding cynomolgus monkey GPR34 (SEQ ID NO: 35) was contained. Using the plasmid described above, Escherichia coli TOP10 was transfected to give Escherichia coli TOP10/pcr-4-monGPR34. The homology in amino acid sequence was 98.7% between cynomolgus monkey GPR34 and human GPR34.

EXAMPLE 4

Expression Distribution of Rat GPR34 Gene and Quantification of its Expression Level in Various Sites from Rats The whole brain, hypophysis, spinal cord, stomach, duodenum, jejunum, ileum, cecum, colon, liver, thymus, spleen, periabdominal fat, perirenal fat, peritesticular fat, prostate gland, testis, ovary, uterus, spermatophore, heart, back muscle, lung, kidney, adrenal gland, peritoneal macrophage and peritoneal mast cells were taken from Wistar rats and total RNA fractions were prepared using RNeasy (Qiagen). The RNA obtained was digested with proteinase K (Invitrogen) to cleave RNase and then genomic DNA was digested with DNase I using a Message Clean Kit (GenHunter). Using as a template 1 µg of total RNA from various parts, reverse transcription was performed using SuperScript II ReverseTranscriptase (Invitrogen) and random primers in accordance with the manual attached to prepare cDNA. PCR was performed in 25 µl of the reaction mixture containing the amount equivalent to 25 ng total RNA of the reverse transcription product obtained or standard cDNA prepared as later described, 1× Universal PCR Master Mix (Applied Biosystems), 100 nM each of primer 1 shown by SEQ ID NO: 37 and primer 2 shown by SEQ ID NO: 38 and 100 nM TaqMan probe shown by SEQ ID NO: 39. PCR was carried out, after heating at 50° C. for 2 minutes and 95° C. for 10 minutes, by repeating 40 times the cycle set to include 95° C. for 15 seconds and 60° C. for 60 seconds.

Standard cDNA was prepared as follows. Using as a template 50 pg of plasmid pcr2.1-ratGPR34 having the full-length rat GPR34, PCR was carried out in a volume of 200 µl using primer 1 and primer 2 (SEQ ID NO: 37 and SEQ ID NO: 38). The reaction mixture was composed of 0.5 µM each of primers 1 and 2, 2.5 mM $MgCl_2$, 0.2 mM dNTP, $\frac{1}{100}$ volume of AmpliTaq Gold (Applied Biosystems) and $\frac{1}{10}$ volume of 10-fold concentrated AmpliTaq Gold Buffer. The reaction was carried out, after keeping at 95° C. for 10 minutes, by repeating 40 times the cycle set to include 95° C. for 15 seconds, 60° C. for 15 seconds and 72° C. for 10 seconds. The amplified product was purified from the reaction solution and absorbance was measured at 260 nm to calculate the concentration and determine the accurate copy number. The product was then diluted in distilled water and a solution of $1 \times 10^7$ copies of standard cDNA was prepared from one copy. Also, the probe and primers for TaqMan PCR were designed using Primer Express (Version 1.0) (Applied Biosystems).

The expression level was computed by ABI PRISM 7700 SDS software. The cycle number at the moment when the fluorescence intensity of the reporter reached the given value was taken on the ordinate and the logarithmic value of the initial concentration of standard cDNA was taken on the abscissa to prepare the standard curve. The initial concentration of each reverse transcription product was calculated from the standard curve to determine the expression level of rat GPR34 gene per 25 ng of total RNA in various sites. In addition, the expression level of rat GAPDH gene in each sample was determined by TaqMan PCR using rodent GAPDH assay kit (Applied Biosystems) in a manner similar to the analysis of rat GPR34 gene expression level to correct the expression level of rat GPR34 gene.

Figure 2:
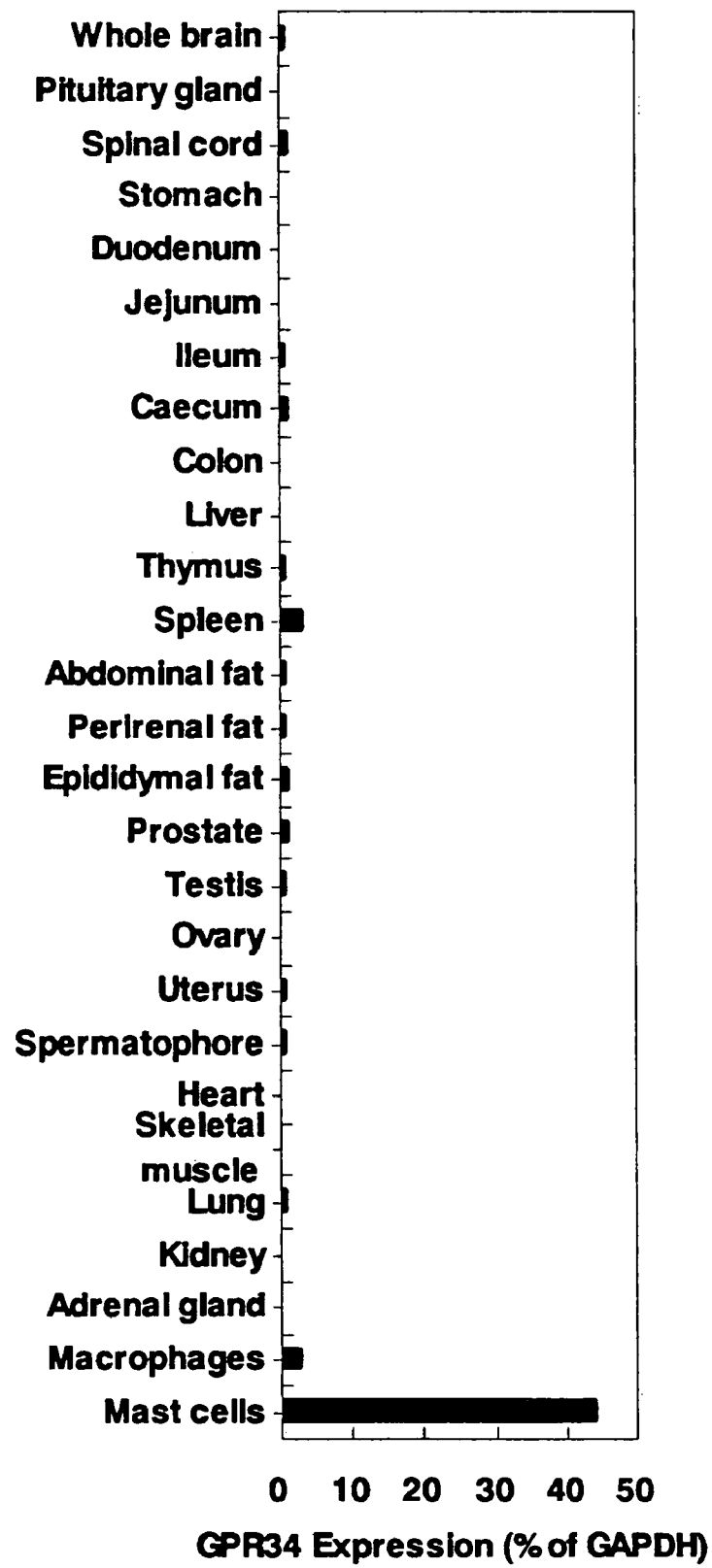
FIG. 2 shows the expression levels of GPR34 in the respective tissues and cells from rats. In the figure, % denotes a ratio of the GPR34 expression level to the GAPDH expression level, after determining the expression levels of GPR34 and GAPDH by TaqMAN PCR using RNA extracted from various tissues and cells of rats.

As a result, the expression level of rat GPR34 gene against rat GAPDH gene showed 0.65% in the whole brain, 0.59% in the hypophysis, 1.14% in the spinal cord, 0.32% in the stomach, 0.39% in the duodenum, 0.38% in the jejunum, 0.69% in the ileum, 1.00% in the cecum, 0.32% in the colon, 0.09% in the liver, 0.84% in the thymus, 3.02% in the spleen, 0.64% in the periabdominal fat, 0.81% in the perirenal fat, 1.35% in the peritesticular fat, 1.13% in the prostate gland, 0.74% in the testis, 0.45% in the ovary, 0.83% in the uterus, 0.81% in the spermatophore, 0.08% in the heart, 0.01% in the back muscle, 0.67% in the lung, 0.11% in the kidney, 0.26% in the adrenal gland, 2.80% in the peritoneal macrophage and 44.0% in the peritoneal mast cells. The foregoing results reveal that rat GPR34 gene is abundantly expressed especially in rat peritoneal mast cells (FIG. 2).

EXAMPLE 5

Expression Distribution of Mouse GPR34 Gene and Quantification of its Expression Level in Various Sites from Mice The brain, stomach, small intestine, liver, thymus, spleen, prostate gland, heart, lung, kidney, macrophages, bone marrow and bone marrow-derived mast cells were taken from Balb/c mouse and the total RNA fraction was prepared using RNeasy (Qiagen). Total RNA was prepared also from WEHI-3, BAF/3 and MC3T3-E1 cells. The RNA obtained was digested with proteinase K (Invitrogen) to cleave RNase and genomic DNA was then digested with DNase I using a Message Clean Kit (GenHunter). Using as a template 1 µg of total RNA in various sites, reverse transcription was performed with SuperScript II ReverseTranscriptase (Invitrogen) using random primers in accordance with the manual attached to prepare cDNA. PCR was performed in 25 µl of the reaction mixture containing the amount equivalent to 25 ng total RNA of the reverse transcription product obtained or standard cDNA prepared as later described, 1× Universal PCR Master Mix (Applied Biosystems), 100 nM each of primer 1 shown by SEQ ID NO: 37 and primer 4 shown by SEQ ID NO: 40 and 100 nM TaqMan probe shown by SEQ ID NO: 39. PCR was carried out, after heating at 50° C. for 2 minutes and 95° C. for 10 minutes, by repeating 40 times the cycle set to include 95° C. for 15 seconds and 60° C. for 60 seconds.

Standard cDNA was prepared as follows. Using as a template 50 pg of plasmid pcr2.1-mouseGPR34 obtained based on the sequence of NCBI Accession No. NM_011823, PCR was carried out in a volume of 200 μl using primer 1 and primer 4 (SEQ ID NO: 37 and SEQ ID NO: 40). The reaction mixture was composed of 0.5 μM each of primers 1 and 4, 2.5 mM $MgCl_2$, 0.2 mM dNTP, 1/100 volume of AmpliTaq Gold (Applied Biosystems) and 1/10 volume of 10-fold concentrated AmpliTaq Gold Buffer. The reaction was carried out, after keeping at 95° C. for 10 minutes, by repeating 40 times the cycle set to include 95° C. for 15 seconds, 60° C. for 15 seconds and 72° C. for 10 seconds. The amplified product was purified from the reaction solution and absorbance was measured at 260 nm to calculate the concentration and determine the accurate copy number. The product was then diluted in distilled water and a solution of $1 \times 10^7$ copies of standard cDNA was prepared from one copy. The probe and primers for TaqMan PCR were designed using Primer Express (Version 1.0) (Applied Biosystems).

The expression level was computed by ABI PRISM 7700 SDS software. The cycle number at the moment when the fluorescence intensity of the reporter reached the given value was taken on the ordinate and the logarithmic value of the initial concentration of standard cDNA was taken on the abscissa to prepare the standard curve. The initial concentration of each reverse transcription product was calculated from the standard curve to determine the expression level of mouse GPR34 gene per 25 ng of total RNA in various sites. In addition, the expression level of mouse GAPDH gene in each sample was determined by TaqMan PCR using rodent GAPDH assay kit (Applied Biosystems) in a manner similar to the analysis of mouse GPR34 gene expression level to correct the expression level of mouse GPR34 gene.

As a result, the expression level of mouse GPR34 gene against mouse GAPDH gene showed 2.58% in the brain, 2.00% in the stomach, 2.28% in the small intestine, 0.27% in the liver, 0.49% in the prostate gland, 0.97% in the heart, 3.81% in the lung, 0.63% in the kidney, 4.60% in the spleen, 2.71% in the spleen B cells, 0.95% in the spleen T cells, 0.79% in the macrophages, 1.23% in the bone marrow, 0.008% in the MC3T3-E1 cells, 0.05% in the WEHI-3 cells, 0.16% in the BAF/3 cells, 4.73% in the MC/9 cells, 8.65% in the IC-2 cells and 37.1% in the bone marrow-derived mast cells.

Figure 3:
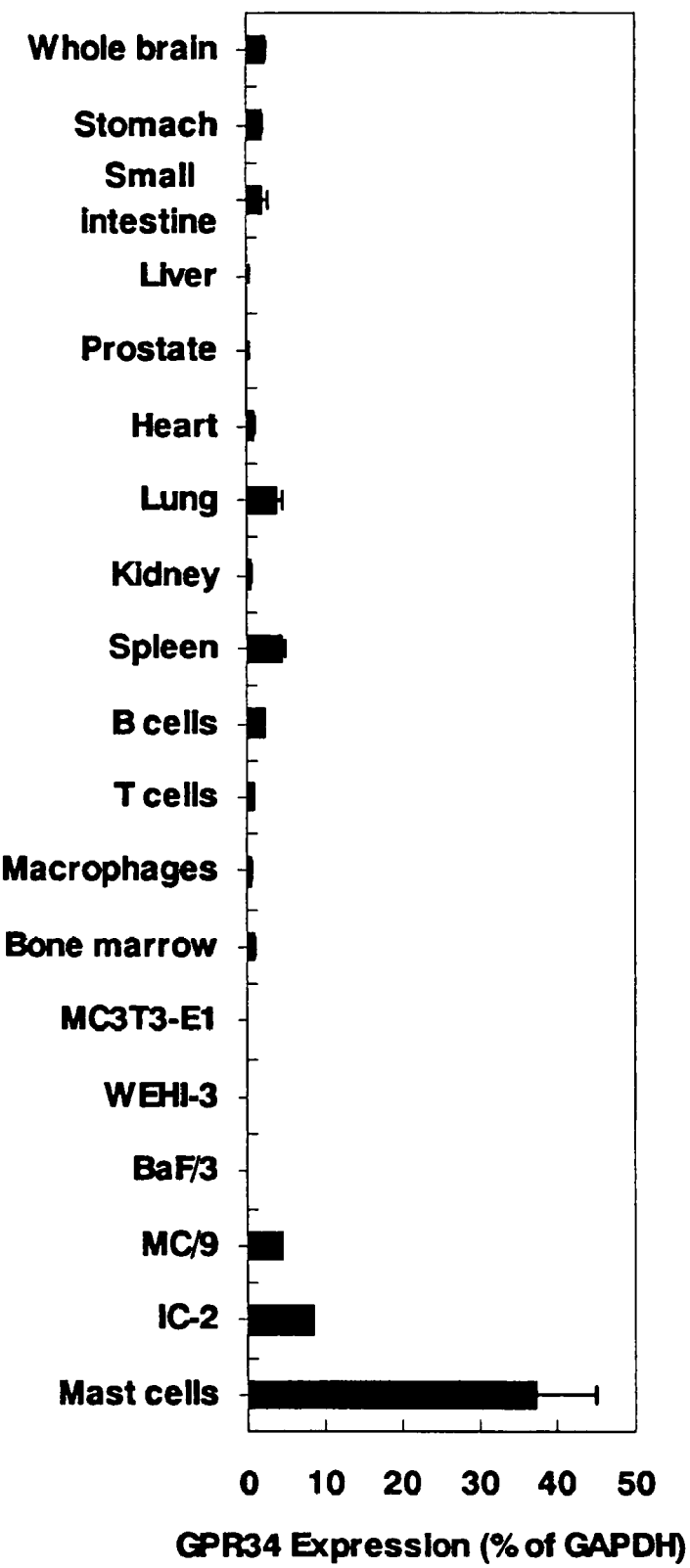
FIG. 3 shows the expression levels of GPR34 the respective tissues and cells from mice. In the figure, % denotes a ratio of the GPR34 expression level to the GAPDH expression level, after determining the expression levels of GPR34 and GAPDH by TaqMAN PCR using RNA extracted from various tissues and cells of mice.

The foregoing results reveal that mouse GPR34 gene is abundantly expressed especially in mouse bone marrow-derived mast cells (FIG. 3).

EXAMPLE 6

Promotion of lysoPS-Dependent Degranulation in Mast Cells

The rat peritoneal mast cells (RPMC) obtained by the procedure described in EXAMPLE 1 were subjected to passive sensitization for 30 minutes on ice using DNP IgE (Yamasa, 10 μg/ml), washed and plated on a 96-well plate in a final cell concentration of 100,000 cells/well in the reaction solution. RPMC was stimulated by lysoPS and DNP-BSA (Carbiochem) and the plate was centrifuged 20 minutes after. The β-hexosaminidase activity in the supernatant of the reaction solution was assayed using the degradation activity of 4-methylumbeliferryl-2-acetamido-2-deoxy-β-D-glucopyranoside (Wako Pure Chemicals) as an indicator.

As a result, spontaneous degranulation was 3.1%. In the absence of lysoPS, degranulation induced by stimulation with 100 ng/ml of DNP-BSA was 4.4%. The degranulation induced by stimulation with 100 ng/ml of DNP-BSA was 8.4% when 0.1 μM lysoPS was added simultaneously, 14.7% when 0.3 μM lysoPS was added simultaneously, 26.0% when 1 μM lysoPS was added simultaneously, 36.7% when 3 μM lysoPS was added simultaneously, lysoPS, and 45.2% when 10 μM lysoPS was added simultaneously, indicating that degranulation was increased concentration-dependently.

These results reveal that promotion of degranulation in mast cells was increased dependently on the concentration of lysoPS.

EXAMPLE 7

Promotion of lysoPS-Dependent Degranulation in Human GPR34-Expressed CHO Cells

The human GPR34-expressed CHO cells prepared by the procedure as described in REFERENCE EXAMPLE 1 were plated at a cell density of 20,000 cells/well on a 96-well plate charged with serum-free medium. The cells were allowed to stand for 4 hours, 0, 0.1, 0.3, 1 and 3 μM lysoPS was added thereto, respectively, followed by incubation for 16 hours. After 1 μCi/well of tritium-labeled thymidine (Amersham, TRK120) was added to achieve labeling for 4 hours, fixation was performed in 10% trichloroacetic acid. Solubilization in an aqueous sodium hydroxide solution was followed by neutralization in trichloroacetic acid to collect DNA with a cell harvester. The radioactivity on the filter was taken as DNA synthesis activity.

The DNA synthesis activity of human GPR34-expressed CHO cells was increased 1.1 times when 0.1 μM lysoPS was added, 1.2 times when 0.3 μM lysoPS was added, 2.0 times when 1 μM lysoPS was added, and 3.2 times when 3 μM lysoPS was added, respectively. These results reveal that DNA synthesis activity of human GPR34-expressed CHO cells was increased dependently on the concentration of lysoPS.

EXAMPLE 8

Assay for lysoPS-Dependent Eicosanoid Production Promoting Activity

The human mast cell line LAD2 cells obtained from National Institute of Health in US were subjected to passive sensitization overnight using DNP IgE (Yamasa, 1 μg/ml), washed and plated on a 96-well plate in a final cell concentration of 100,000 cells/well in the reaction solution. LAD2 cells were stimulated by lysoPS and DNP-BSA and the plate was centrifuged 20 minutes after. The leukotriene in the supernatant of the reaction solution was assayed using Leukotriene EIA Kit (Amersham).

In the absence of lysoPS, leukotriene production of LAD 2 cells by stimulation with 300 ng/ml of DNP-BSA was 218 pg/ml. The leukotriene production by stimulation with 300 ng/ml of DNP-BSA was 382 pg/ml when 0.1 μM lysoPS was added simultaneously, 529 pg/ml when 0.3 μM lysoPS was added simultaneously, 638 pg/ml when 1 μM lysoPS was added simultaneously, 750 pg/ml when 3 µM lysoPS was added simultaneously, lysoPS, and 792 pg/ml when 10 µM lysoPS was added simultaneously.

The results reveal that promotion of the eicosanoid production was enhanced dependently on the concentration of lysoPS.

EXAMPLE 9

Expression Distribution and Quantification of Expression Level of Human GPR34 Gene in Various Sites of Human Human cDNA panel was purchased from Clontech, Inc. The total RNA fraction was prepared from the human mast cell line LAD2 cells obtained from National Institute of Health in US using a set of RNeasy and DNase I (Qiagen). Using 1 µg of the total RNA as a template, reverse transcription was performed with SuperScript II ReverseTranscriptase (Invitrogen) using random primers in accordance with the manual attached to prepare cDNA. PCR was performed in 25 µl of the reaction mixture containing the amount equivalent to 25 ng total RNA of the reverse transcription product obtained or standard cDNA prepared as later described, 1× Universal PCR Master Mix (Applied Biosystems), 100 nM each of primer 1 (SEQ ID NO: 41) and primer 2 (SEQ ID NO: 42) and 100 nM TaqMan probe (SEQ ID NO: 43). PCR was carried out, after heating at 50° C. for 2 minutes and 95° C. for 10 minutes, by repeating 40 times the cycle set to include 95° C. for 15 seconds and 60° C. for 60 seconds.

Standard cDNA was prepared as follows. Using as a template 50 pg of plasmid pAKKO-hGPR34 having the full-length human GPR34 prepared by the procedure described in REFERENCE EXAMPLE 1, PCR was carried out in a total volume of 200 µl using primer 1 (SEQ ID NO: 41) and primer 2 (SEQ ID NO: 42). The reaction mixture was composed of 0.5 µM each of primers 1 and 2, 2.5 mM $MgCl_2$, 0.2 mM dNTP, 1/100 volume of AmpliTaq Gold (Applied Biosystems) and 1/10 volume of 10-fold concentrated AmpliTaq Gold Buffer. The reaction was carried out, after keeping at 95° C. for 10 minutes, by repeating 40 times the cycle set to include 95° C. for 15 seconds, 60° C. for 15 seconds and 72° C. for 10 seconds. The amplified product was purified from the reaction solution and absorbance was measured at 260 nm to calculate the concentration and determine the accurate copy number. The product was then diluted in distilled water and a solution of $1 \times 10^7$ copies of standard cDNA was prepared from one copy. Also, the probe and primers for TaqMan PCR were designed using Primer Express (Version 1.0) (Applied Biosystems).

The expression level was computed by ABI PRISM 7700 SDS software. The cycle number at the moment when the fluorescence intensity of the reporter reached the given value was taken on the ordinate and the logarithmic value of the initial concentration of standard cDNA was taken on the abscissa to prepare the standard curve. The initial concentration of each reverse transcription product was calculated from the standard curve to determine the expression level of human GPR34 gene per 25 ng of total RNA in various sites. In addition, the expression level of human GAPDH gene in each sample was determined by TaqMan PCR using human GAPDH assay kit (Applied Biosystems) in a manner similar to the analysis of human GPR34 gene expression level to correct the expression level of human GPR34 gene.

As a result, the expression level of human GPR34 gene against human GAPDH gene showed 0.8% in the whole brain, 0.31% in the heart, 0.33% in the kidney, 0.59% in the liver, 1.32% in the lung, 0.88% in the pancreas, 5.05% in the placenta, 0.01% in the skeletal muscle, 3.61% in the spleen, 2.69% in the thymus, 0.57% in the prostate gland, 0.56% in the testis, 1.86% in the ovary, 0.75% in the small intestine, 0.54% in the large intestine, 0.58% in the leukocytes, and 14.1% in the mast cell line LAD 2 cells.

The foregoing results reveal that human GPR34 gene is abundantly expressed especially in human mast cell line.

EXAMPLE 10

MAPK Activating Activity of lysoPS in Human-Derived GPR34-Expressed CHO Cells

The MAPK activating activity of lysophosphatidylserine (hereinafter lysoPS) in human-derived GPR34-expressed CHO cells prepared in a manner similar to the procedure described in REFERENCE EXAMPLE 1 was detected as follows.

The cells were prepared as described below. Human GPR34-expressed CHO cells were scraped off with 0.05% trypsin-EDTA (GIBCO) and suspended in a medium (MEM-α (GIBCO), supplemented with 10% FBS (GIBCO) and penicillin/streptomycin (BIOWHITTAKER)). After centrifugation, the cells precipitated were suspended in the medium in $2 \times 10^5$ cells/ml and a 1 mL aliquot was plated on a 35 mm cell culture dish. After incubation overnight in a $CO_2$ incubator, the medium was aspirated and washed in PBS. Then 1 mL of serum-free medium (MEM-α (GIBCO), supplemented with penicillin/streptomycin (BIOWHITTAKER)) and incubation was performed in a $CO_2$ incubator. Pertussis toxin (hereinafter PTX) was added in a final concentration of 0.1 µg/mL 20 hours before the assay.

The cells were activated as follows. The medium was aspirated and washed in PBS. Thereafter, 500 µL of assay buffer (HBSS (GIBCO), 10 mM HEPES (Dojin Chemical Laboratory)) was added to perform preincubation for 15 minutes at 37° C. The lysoPS solution and 500 mL of PECGF (β-endothelial cell growth factor) solution as a positive control were added. After the mixture was incubated at 37° C., the reaction was terminated by quenching. The assay buffer was aspirated and washed in PBS. Then, 1×SDS sample buffer/DTT was added to the cells to recover the cells. After ultrasonication for 15 seconds, heating at 95° C. for 5 minutes was followed by quenching.

Detection by SDS-PAGE and western blotting were performed as follows. After separation using 10% Bis-Tris gel (Invitrogen), the gel was transferred to Immuno-Blot PVDF Membrane (Bio-Rad). The membrane was blocked with Block Ace (Dai-Nippon Pharmaceutical) and incubated at room temperature for an hour with a primary antibody (Phospho-p42/p44 MAP Kinase (Thr202/Thr204) Antibody (CST) or p42/p44 MAP Kinase Antibody (CST)) and further incubated at room temperature for an hour using a secondary antibody (Anti-rabbit IgG (CST)). The membrane after the antibody reaction was visualized by chemiluminescence using ECL PLUS (Amersham Biosciences). Detection and image analysis were performed using LAS1000 (FUJI FILM).

Figure 6:
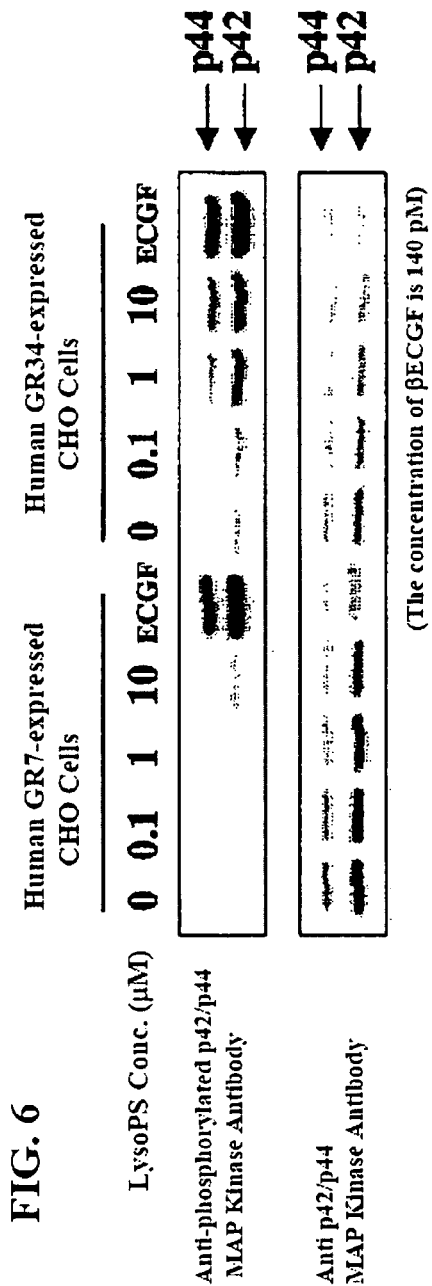
FIG. 6 shows a lysoPS concentration dependency of ERK1/2 (p42/p44 MAP Kinase) on phosphorylation using human GPR34-expressed CHO cells when stimulated by lysoPS. Arrow in the figure denotes the band position of p44 MAPK or p42 MAPK detected by each antibody.
Figure 7:
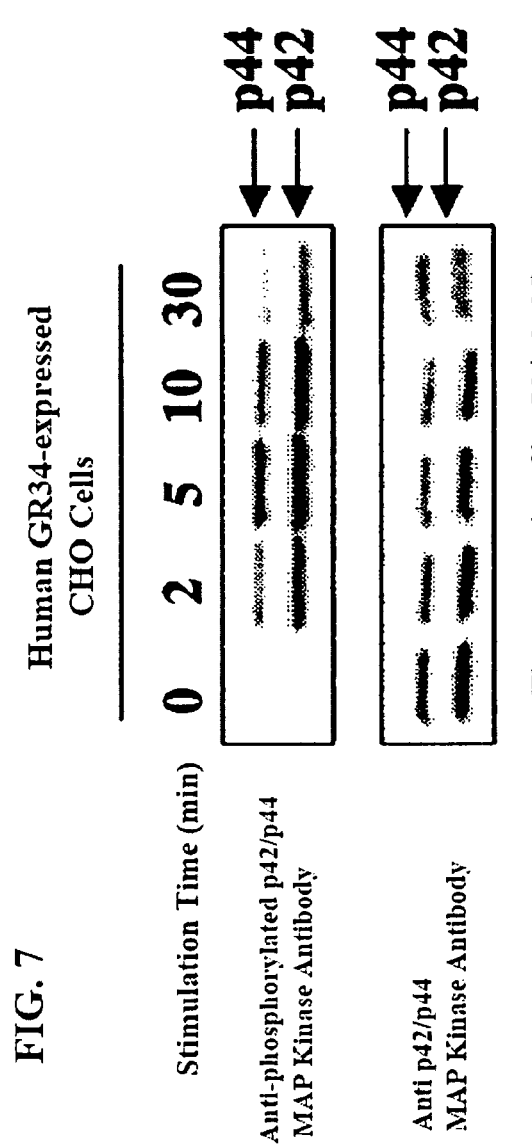
FIG. 7 shows changes with passage of time in phosphorylation of ERK1/2 (p42/p44 MAP Kinase) using human GPR34-expressed CHO cells when stimulated by lysoPS. Arrow in the figure denotes the band position of p44 MAPK or p42 MAPK detected by each antibody.
Figure 8:
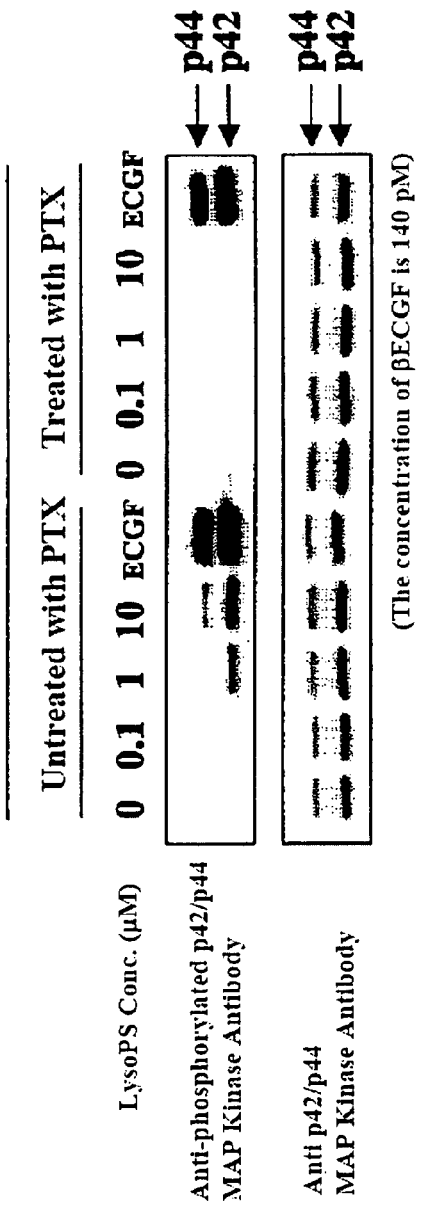
FIG. 8 shows actions of ERK1/2 (p42/p44 MAP Kinase) on phosphorylation using human GPR34-expressed CHO cells when the cells were treated with pertussis toxin (PTX) upon stimulation by lysoPS. Arrow in the figure denotes the band position of p44 MAPK or p42 MAPK detected by each antibody.

As a result, the phosphorylation of ERK1/2 (p42/p44 MAP Kinase) was observed concentration-dependently when human GPR34-expressed CHO cells were stimulated with lysoPS. On the other hand, when human GPR7-expressed CHO cells were stimulated with lysoPS, the phosphorylation of ERK1/2 (p42/p44 MAP Kinase) was not detected (FIG. 6). The phosphorylation of ERK1/2 ERK1/2 (p42/p44 MAP Kinase) by lysoPS in human GPR34-expressed CHO cells showed the maximum response about 5 minutes after the stimulation and even 30 minutes after the stimulation, the phosphorylation was noted (FIG. 7). Also, the phosphorylation of ERK1/2 (p42/p44 MAP Kinase) by lysoPS in human GPR34-expressed CHO cells was attenuated to the level below the detection limit by pretreating PTX (FIG. 8).

EXAMPLE 11

MAPK-Activating Activity of lysoPS in Mouse Bone Marrow-Derived Mast Cells

The MAPK activating activity of lysoPS in mouse bone marrow-derived mast cells (hereinafter BMMC) was detected as follows.

BMMC was established by collecting bone marrow fluid from the femur of male BALB/c mouse (Japan SLC), rinsing in RPMI1640 (Nikken Bio Medical Laboratory) and then incubating in a medium (RPMI1640, 50% WEHI-3 culture supernatant, 10% FBS (GIBCO), penicillin/streptomycin (BIOWHITTAKER), Non-Essential amino acids (GIBCO)) for 4 weeks. The cells were incubated in a $CO_2$ incubator immediately before assay. Pertussis toxin (hereinafter PTX) was added to the cells in a final concentration of 0.1 µg/mL 4 hours before assay. BMMC was washed in ice-chilled assay buffer (Tyrode Buffer, 0.01% fatty acid free-BSA (SIGMA), 1 mM $CaCl_2$, 1 mM $MgCl_2$), and suspended in $2\times10^6$ cells/ml. The suspension was dispensed in a 1.5 mL tube followed by preincubation for 15 minutes at 37° C. The lysoPS solution and A23187 solution (Wako Pure Chemicals) as a positive control were added in equimolar amounts. After incubation at 37° C., the reaction was terminated by quenching. The cells were precipitated by centrifugation and the assay buffer was aspirated. After washing in PBS, 1×SDS sample buffer/DTT was added to the cells to lyse the cells. After ultrasonication for 15 seconds, the sample was heated at 95° C. for 5 minutes followed by quenching.

Detection by SDS-PAGE and western blotting were performed as follows. After separation using 10% Bis-Tris gel (Invitrogen), the gel was transferred to Immuno-Blot PVDF Membrane (BIO-RAD). The membrane was blocked with Block Ace (Dai-Nippon Pharmaceutical) and incubated at 4° C. overnight with a primary antibody (Phospho-p42/p44 MAP Kinase (Thr202/Thr204) Antibody (CST) or p42/p44 MAP Kinase Antibody (CST)) and further incubated at room temperature for an hour using a secondary antibody (Anti-rabbit IgG (CST)). The membrane after the antibody reaction was visualized by chemiluminescence using ECL PLUS (Amersham Biosciences). Detection and image analysis were performed using LAS1000 (FUJI FILM).

Figure 9:
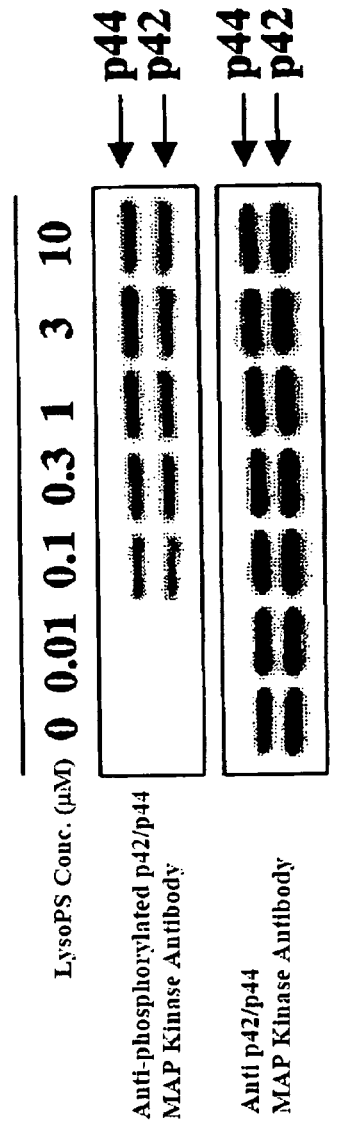
FIG. 9 shows a lysoPS concentration dependency of ERK1/2 (p42/p44 MAP Kinase) on phosphorylation using mouse bone marrow mast cells when stimulated by lysoPS. Arrow in the figure denotes the band position of p44 MAPK or p42 MAPK detected by each antibody.
Figure 10:
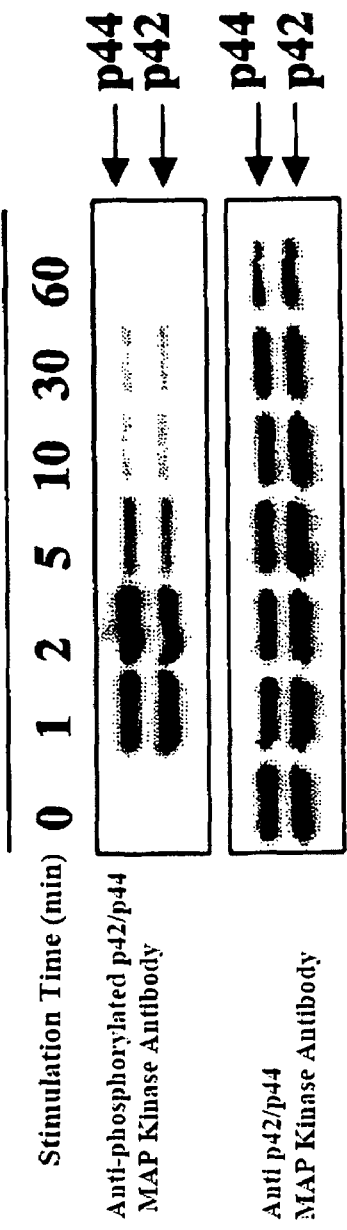
FIG. 10 shows changes with passage of time in phosphorylation of ERK1/2 (p42/p44 MAP Kinase) using mouse bone marrow mast cells when stimulated by lysoPS. Arrow in the figure denotes the band position of p44 MAPK or p42 MAPK detected by each antibody.
Figure 11:
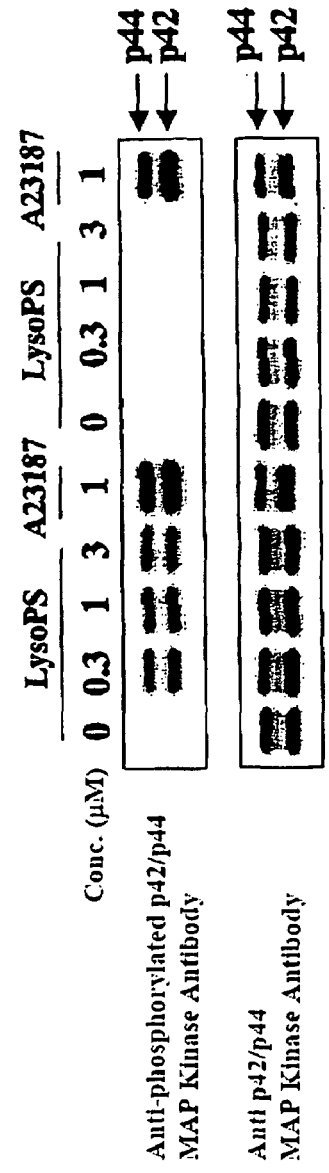
FIG. 11 shows actions of ERK1/2 (p42/p44 MAP Kinase) on phosphorylation using mouse bone marrow mast cells when the cells were treated with pertussis toxin (PTX) upon stimulation by lysoPS. Arrow in the figure denotes the band position of p44 MAPK or p42 MAPK detected by each antibody.

As a result, the phosphorylation of ERK1/2 (p42/p44 MAP Kinase) was noted dependently on the concentration of lysoPS when BMMC was stimulated with lysoPS (FIG. 9). The phosphorylation of ERK1/2 (p42/p44 MAP Kinase) by lysoPS in BMMC showed the maximum response about 2 minutes after the stimulation and even 30 minutes after the stimulation, the phosphorylation was observed (FIG. 10). Also, the phosphorylation of ERK1/2 (p42/p44 MAP Kinase) by lysoPS in BMMC was attenuated to the level below the detection limit by pretreating PTX (FIG. 11).

EXAMPLE 12

MAPK-Activating Activity of lysoPS in Rat Peritoneal Mast Cells

The MAPK activating activity of lysoPS in rat peritoneal mast cells (hereinafter RPMC) collected by the procedure described in EXAMPLE 1 was detected as follows.

Pertussis toxin (hereinafter PTX) was added to the cells in a final concentration of 0.1 µg/mL 4 hours before assay. RPMC was washed in ice-chilled assay buffer (Tyrode Buffer, 0.01% fatty acid free-BSA (SIGMA), 1 mM $CaCl_2$, 1 mM $MgCl_2$), and suspended in $2\times10^6$ cells/ml. The suspension was dispensed in a 1.5 mL tube followed by preincubation for 15 minutes at 37° C. The lysoPS solution was added thereto in an equimolar amount. After incubation at 37° C., the reaction was terminated by quenching. The cells were precipitated by centrifugation and the assay buffer was aspirated. After washing in PBS, 1×SDS sample buffer/DTT was added to the cells to lyse the cells. After ultrasonication for 15 seconds, heating at 95° C. for 5 minutes was followed by quenching.

Detection by SDS-PAGE and western blotting were performed as follows. After separation using 10% Bis-Tris gel (Invitrogen), the gel was transferred to Immuno-Blot PVDF Membrane (BIO-RAD). The membrane was blocked with Block Ace (Dai-Nippon Pharmaceutical) and incubated at 4° C. overnight with a primary antibody (Phospho-p42/p44 MAP Kinase (Thr202/Thr204) Antibody (CST) or p42/p44 MAP Kinase Antibody (CST)) and further incubated at room temperature for an hour with a secondary antibody (Anti-rabbit IgG (CST)). The membrane after the antibody reaction was visualized by chemiluminescence using ECL PLUS (Amersham Biosciences). Detection and image analysis were performed using LAS1000 (FUJI FILM).

Figure 12:
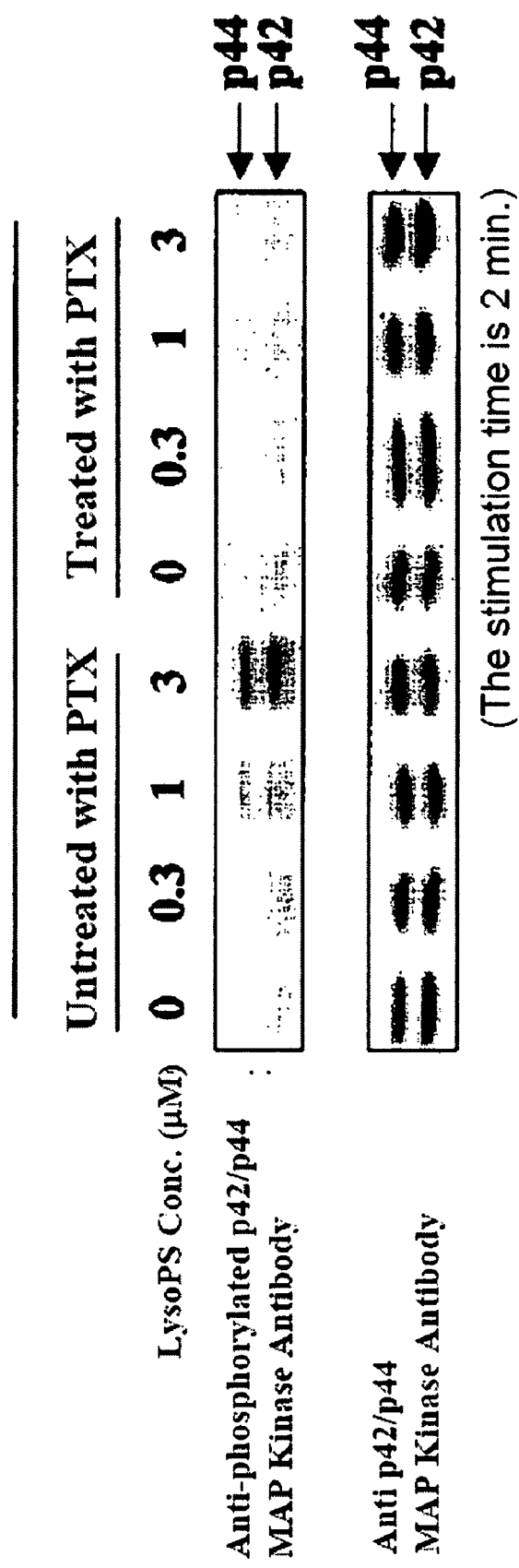
FIG. 12 shows actions of ERK1/2 (p42/p44 MAP Kinase) on phosphorylation using rat peritoneal mast cells when the cells were treated with pertussis toxin (PTX) upon stimulation by lysoPS. Arrow in the figure denotes the band position of p44 MAPK or p42 MAPK detected by each antibody.

As a result, the phosphorylation of ERK1/2 (p42/p44 MAP Kinase) was noted dependently on the concentration of lysoPS when RPMC was stimulated with lysoPS. Also, the phosphorylation of ERK1/2 (p42/p44 MAP Kinase) by lysoPS in RPMC was attenuated to the level below the detection limit by pretreating PTX (FIG. 12).

REFERENCE EXAMPLE 1

(1-1) Cloning of cDNA Encoding Human-Derived G Protein-Coupled Receptor Protein GPR34 and Preparation of Animal Cell Expression Vector Using human genome (Clontech) as a template together with SalI recognition site-added primer 1 (SEQ ID NO: 3) and SpeI recognition site-added primer 2 (SEQ ID NO: 4), PCR was carried out. In this reaction, 100 ng of the genome described above was used as a template and the reaction solution comprised of 2.5 U of Pfu Turbo DNA Polymerase (STRATAGENE), 1.0 µM each of primer 1 (SEQ ID NO: 3) and primer 2 (SEQ ID NO: 4), 200 µM of dNTPs, and 25 µl of 2×GC Buffer I (Takara Shuzo) was added to the enzyme to make the volume 50 µl. PCR was carried out, after maintaining at 94° C. for 1 minute, by repeating 38 times the cycle set to include 94° C. for 30 seconds, 54° C. for 15 seconds and 72° C. for 1.5 minutes. The PCR product was purified using PCR Purification Kit (Qiagen). Elution was performed in 30 µl of Buffer EB attached to the kit, and 10 µl of the eluate was digested with restriction enzymes SalII and SpeI. After agarose gel electrophoresis, the restriction enzyme reaction product was excised from the agarose gel and recovered using Gel Extraction Kit (Qiagen). The reaction product was added to vector plasmid pAKKO-111H for animal cell expression (the same vector plasmid as pAKKO1.11H described in Biochim. Biophys. Acta, 1219, 251-259, 1994), which was digested with SalI and SpeI, followed by ligation using DNA Ligation Kit Ver. 2 (Takara Shuzo). The digestion product was transfected to *Escherichia coli* TOP10 (Invitrogen) and clones bearing cDNA of GPR34 were selected in LB agar medium containing ampicillin. As a result of analysis of the sequence of each clone, *Escherichia coli* bearing the plasmid (which was named pAKKO-GPR34) containing the base sequence (SEQ ID NO: 2) of cDNA encoding GPR34 (SEQ ID NO: 1) was obtained. After *Escherichia coli* TOP10 transfected by this pAKKO-GPR34 was incubated, plasmid DNA of pAKKO-GPR34 was prepared using Plasmid Miniprep Kit (BIORAD). The amino acid sequence of GPR34 obtained coincided with the amino acid sequence of GPR34 described in Genomics, 56, 12-21, 1999, and the 181st amino acid in the amino acid sequence was Leu. The 181st amino acid in the amino acid sequence of GPR34 described in Biochim. Biophys. Acta, 1446, 57-70, 1999 is Val.

(1-2) Preparation of GPR34-Expressed CHO Cell Line

Hamster CHO/dhfr⁻ cells were plated on a Falcon dish (3.5 cm in diameter) with α-MEM medium (GIBCO Cat. No. 12571) containing 10% cow fetal serum in $1×10^5$, followed by incubation at 37° C. in a 5% $CO_2$ incubator. Using Transfection Reagent FuGENE6 (Roche), 2 µg of the expression plasmid pAKKO-GPR34 obtained in (1-1) described above was transfected according to the method described in the instructions attached. After incubation for 18 hours, the medium was replaced by a fresh growth medium. Incubation was continued for further 10 hours. Then, the transfected cells were collected by trypsin-EDTA treatment and plated on a flat-bottomed 96-well plate with selective medium (α-MEM medium containing 10% fetal calf serum (GIBCO Cat. No. 12561)). While exchanging the selective medium every 3 to 4 days, incubation was continued to acquire 76 clones of DHFR⁺ cells grown in colonies 2 to 3 weeks after.

(1-3). Quantification of GPR34 Expression Level in GPR34-Expressed CHO Cell Line Using TaqMan PCR On a 96-well plate, 76 clones from the GPR34-expressed CHO cell line obtained in (1-2) described above were incubated and the total RNA was prepared using RNeasy 96 Kit (Qiagen). Using TaqMan Reverse Transcription Reagents (Applied Biosystems), 1 to 200 ng of the total RNA obtained was subjected to reverse transcription. The obtained reverse transcription product corresponding to 0.1-20 ng of the total RNA, or 0.1 to 20 ng of the total RNA without reverse transcription, or standard cDNA prepared as later described, 0.5 µM each of 2 primers [primer 3 (SEQ ID NO: 5) and primer 4 (SEQ ID NO: 6)] and 0.1 µM of probe 1 (SEQ ID NO: 7; the 5' end and the 3' end were labeled with Fam (6-carboxyfluorescein) and Tamra (6-carboxy-tetramethyl-rhodamine), respectively) were added with 25 µl of TaqMan Universal PCR Master Mix (Applied Biosystems) to make the volume 50 µl, and PCR was carried out. Using ABI7700 (Applied Biosystems), PCR was carried out, after maintaining at 50° C. for 2 minutes and 95° C. for 10 minutes, by repeating 40 times the cycle set to include 95° C. for 15 seconds and 60° C. for 1 minute.

In standard cDNA, absorbance of the plasmid pAKKO-GPR34 obtained in (1-1) described above was measured at 260 nm to calculate the concentration and determine the accurate copy number. The product was then diluted in 10 mM Tris-HCl (pH 8.0) containing 1 mM EDTA and a solution of $1×10^6$ copies of standard cDNA was prepared from one copy. Also, the probe and primers for TaqMan PCR were designed using Primer Express (Version 1.0) (Applied Biosystems).

The expression level was computed by ABI PRISM 7700 SDS software. The cycle number at the moment when the fluorescence intensity of the reporter reached the given value was taken on the ordinate and the logarithmic value of the initial concentration of standard cDNA was taken on the abscissa to prepare the standard curve. The copy numbers of each reverse transcription product and the total RNA without reverse transcription were calculated from the standard curve. By subtracting the value obtained from the PCR product without reverse transcription from the value obtained from the PCR product with reverse transcription, the expression level of GPR34 gene per 1 ng of total RNA in each clone was determined. As a result, 12 clones of the CHO cell line with high GPR34 expression were selected and cultured on a 24-well plate. The expression level of GPR34 was reexamined on these cells. After the total RNA was prepared using RNeasy Mini Kit (Qiagen), reverse transcription was performed as described above to determine the expression level of GPR34 gene in each clone per 1 ng of the total RNA by TaqMan PCR. As a result, the GPR34-expressed CHO cell line clones #1-5 and #1-9 were found to show high expression levels.

In the following REFERENCE EXAMPLES, the expression cells of these two clones were used.

(1-4) Assay for Intracellular cAMP Production Inhibitory Activity Using GPR34-Expressed CHO Cells The GPR34-expressed CHO cells prepared in (1-2) described above and selected in (1-3) described above were plated on a 24-well plate in $6×10^4$ cells/well followed by incubation for 48 hours. The cells were washed with αMEM medium (pH 7.5) containing 0.2 mM 3-isobutylmethylxanthine, 0.05% BSA and 20 mM HEPES (hereinafter αMEM medium (pH 7.5) containing 0.2 mM 3-isobutylmethylxanthine, 0.05% BSA and 20 mM HEPES is referred to as the reaction buffer). Thereafter, 0.5 mL of the reaction buffer was added and the mixture was kept warm for 30 minutes in an incubator. The reaction buffer was removed and 0.25 mL of fresh reaction buffer was replenished to the cells. Then, 0.25 mL of the reaction buffer containing a sample and 2 µM forskolin was added to the cells, followed by reacting at 37° C. for 30 minutes. The reaction solution was removed and 0.5 mL of the cell lysis solution attached to cAMP EIA kit (Applied Biosystems) to extract cAMP in the cells. The cAMP level in the extract was quantified using the same kit. Based on this measurement data, the cAMP production inhibitory activity was calculated based on the equation shown below and expressed in terms of percentage to the control group. The activity in the group added with sample was calculated using each control value set on the same plate.

% of control=$(X-C)/(T-C)×100$

X: cAMP level in the group added with sample
T: mean value of the cAMP levels in 3 wells of the groups without sample addition and with forskolin stimulation
C: mean value of the cAMP levels in 2 wells of the groups without sample addition and without forskolin stimulation (1-5) cAMP Production Inhibitory Activity of Lysophosphatidylserine and Phosphatidylserine on GPR34-Expressed CHO Cells The amino acid sequence of GPR34 is known to have low homology to the amino acid sequence of the platelet-activating factor receptor or the uridine diphosphate glycoside. Thus, various compounds including platelet-activating factor and uridine diphosphate glycoside, which are ligands to the receptors showing homology to GPR34, were administered to the GPR34-expressed CHO cells to examine the cAMP production inhibitory activity of these compounds on the GPR34-expressed CHO cells by the method shown in (1-4) described above.

Figure 4:
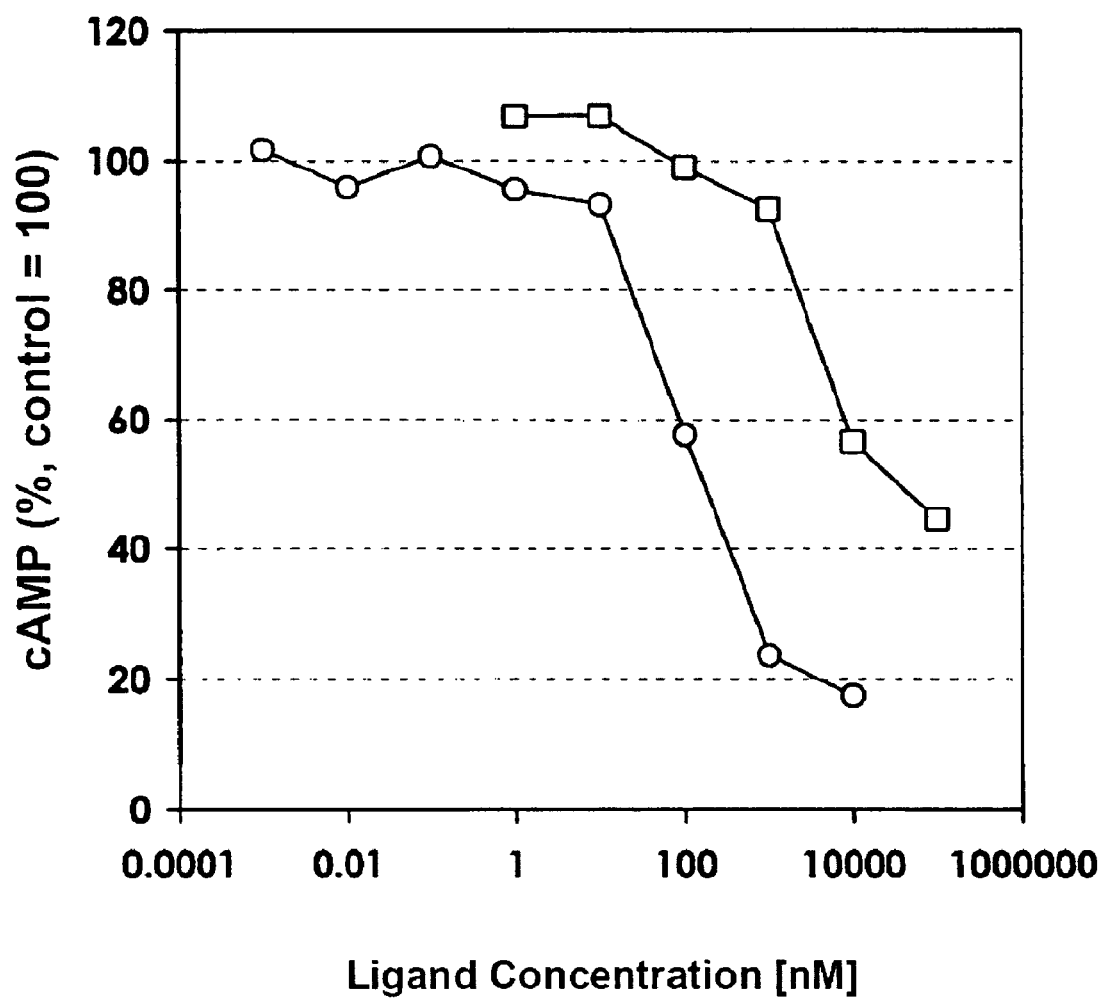
FIG. 4 shows cAMP production inhibitory activities of lysophosphatidylserine and phosphatidylserine against GPR34-expressed CHO cells. In the figure, symbol -o- denotes the activity when lysophosphatidylserine was administered and symbol -□- denotes the activity when phosphatidylserine was administered.

As a result, two compounds, i.e., lysophosphatidylserine (Sigma, L 5772) and phosphatidylserine (Sigma, P 7769) in a higher concentration showed marked activities. The action was not noted on the other receptor expression cells but was receptor-specific. Based on these results, it was concluded that these two compounds were ligands to GPR34. FIG. 4 shows the cAMP production inhibitory activities when lysophosphatidylserine and phosphatidylserine in various concentrations were administered to the GPR34-expressed CHO cells.

(1-6) Screening of Compound that Changes Binding Properties of GPR34 to Lysophosphatidylserine or Phosphatidylserine The GPR34-expressed CHO cells prepared in (1-2) described above and selected in (1-3) described above were plated on a 24-well plate in $1\times10^5$ cells/well followed by incubation for 24 hours. The cells were washed with αMEM medium (pH 7.5) containing 0.2 mM 3-isobutylmethylxanthine and 20 mM HEPES (hereinafter αMEM medium (pH 7.5) containing 0.2 mM 3-isobutylmethylxanthine and 20 mM HEPES is referred to as the reaction buffer). Thereafter, 0.5 mL of the reaction buffer was added and the mixture was kept warm for 30 minutes in an incubator. The reaction buffer was removed and 0.25 mL of fresh reaction buffer was replenished to the cells. Then, (a) 0.25 mL of the reaction buffer containing 2.5 µM forskolin with addition of 1 µM lysophosphatidylserine or 10 µM phosphatidylserine or (b) 0.25 mL of the reaction buffer containing 2 µM forskolin with addition of 1 µM lysophosphatidylserine or 10 µM phosphatidylserine and a test compound, was added to the cells, followed by reacting at 37° C. for 30 minutes. The reaction solution was removed and 0.5 mL of the cell lysis solution attached to cAMP EIA kit (Applied Biosystems) to extract cAMP in the cells. The cAMP level in the extract was quantified using the same kit. Based on this measurement data, the cAMP production inhibitory activity was calculated based on the equation shown below and expressed in terms of percentage to the control group. The activity in the group added with sample was calculated using each control value set on the same plate.

% of control=$(X-C)/(T-C)\times100$

X: cAMP level in the group added with sample
T: mean value of the cAMP levels in 3 wells of the groups without sample addition and with forskolin stimulation
C: mean value of the cAMP levels in 2 wells of the groups without sample addition and without forskolin stimulation Effects of the test compound on the cAMP production inhibitory activity by lysophosphatidylserine or phosphatidylserine were examined by comparing the cAMP production inhibitory activity when lysophosphatidylserine or phosphatidylserine was added to the cells and the cAMP production inhibitory activity when lysophosphatidylserine or phosphatidylserine and the test compound were added to the cells.

The test compound that attenuates the cAMP production inhibitory activity by lysophosphatidylserine or phosphatidylserine is selected to be a candidate substance capable of competitive inhibition; and the test compound that potentiates the cAMP production inhibitory activity by lysophosphatidylserine or phosphatidylserine is selected to be a candidate substance capable of promoting the binding (binding of lysophosphatidylserine or phosphatidylserine to GPR34).

REFERENCE EXAMPLE 2

Cloning of cDNA Fragment Encoding a Portion of Rat-Derived G Protein-Coupled Receptor Protein GPR34

In order to acquire cDNA encoding a part of rat-derived G protein-coupled receptor protein GPR34, PCR was carried out using primer 1 (SEQ ID NO: 8) and primer 2 (SEQ ID NO: 9) designed based on the consensus sequence between human GPR34 and mouse GPR34. The solution for PCR was made up to a volume of 20 µl and was composed of 1 µl of rat whole brain Marathon ready cDNA (Clontech) as a template, 0.2 µM each of the primers, 0.2 mM dNTP, 0.5 M GC-Melt, 1/50 volume of Advantage-GC 2 Polymerase Mix (Clontech) and 1/5 volume of 5-fold condensed buffer. The cycle for amplification was performed by maintaining at 96° C. for 2 minutes, repeating 35 times one cycle set to include 96° C. for 30 seconds, 54° C. for 30 seconds and 72° C. for 1 minute, and then maintaining at 72° C. for 10 minutes. Using TOPO TA cloning kit (Invitrogen), the reaction solution was subcloned to plasmid vector pCR2.1-TOPO and transfected to *Escherichia coli* DH5α-T1. From the resulting transformant, the plasmid DNA was purified using QIAwell 8 Ultra Plasmid Kit (Qiagen). The reaction for base sequencing was carried out using BigDye Terminator Cycle Sequence Ready Reaction Kit (Perkin-Elmer). As a result of decoding on a fluorescent automatic sequencer, the base sequence represented by SEQ ID NO: 10, which is the sequence of cDNA fragment encoding a part of rat-derived G protein-coupled receptor protein GPR34, was obtained.

REFERENCE EXAMPLE 3

Cloning of Partial Sequence of cDNA at the 3' End Encoding Rat-Derived G Protein-Coupled Receptor Protein GPR34 by 3' RACE Rat whole brain Marathon ready cDNA (CLONTECH) was used as a template for 3' RACE. The primer set used for RACE PCR was the adaptor primer 1 attached to the kit and primer 1 (SEQ ID NO: 11) for the first PCR, and the adaptor primer 2 attached to the kit and primer 2 (SEQ ID NO: 12) for the second PCR, respectively. In the first PCR, the PCR solution was made up to a volume of 50 µl and composed of 5 µl of template cDNA, 0.2 µM each of the primers, 0.2 mM dNTP, 1/50 volume of Advantage 2 Polymerase Mix (CLONTECH), and 1/10 volume of 10-fold condensed buffer. The cycle for amplification was performed by maintaining at 94° C. for 2 minutes, then repeating 30 times one cycle set to include 94° C. for 30 seconds and 68° C. for 2 minutes and maintaining at 72° C. for 10 minutes. In the second PCR, the volume of the PCR solution was made 50 µl and the composition was as follows: 5 µl of a 10-fold dilution of the first PCR reaction solution as a template, 0.2 µM each of the primers, 0.2 mM dNTP, 1/50 volume of Advantage 2 Polymerase Mix and 1/10 volume of 10-fold condensed buffer. The cycle for amplification was performed by maintaining at 94° C. for 2 minutes, then repeating 20 times one cycle set to include 94° C. for 30 seconds and 69° C. for 2 minutes and maintaining at 72° C. for 10 minutes. The reaction product was electrophoresed on 0.8% Seakem LE Agarose (TaKaRa Shuzo Co., Ltd.). A band around 800 bp observed when stained with ethidium bromide was extracted with QIAquick Gel Extraction Kit (Qiagen), subcloned to plasmid vector pCR2.1-TOPO using TOPO TA cloning kit (Invitrogen), and transfected to *Escherichia coli* DH5α-T1. The plasmid DNA was purified from the resulting transformant using QIAwell 8 Ultra Plasmid Kit (Qiagen). The reaction for base sequencing was carried out using BigDye Terminator Cycle Sequence Ready Reaction Kit (Perkin-Elmer). As a result of decoding on a fluorescent automatic sequencer, the base sequence represented by SEQ ID NO: 13, which is the partial sequence of cDNA at the 3' end, encoding rat-derived G protein-coupled receptor protein GPR34, was obtained.

REFERENCE EXAMPLE 4

Cloning of Partial Sequence of cDNA at the 3' End Encoding Rat-Derived G Protein-Coupled Receptor Protein GPR34 by 5' RACE Rat spleen Marathon ready cDNA (CLONTECH) was used as a template for 5' RACE. The primer set used for RACE PCR was the adaptor primer 1 attached to the kit and primer 1 (SEQ ID NO: 14) for the first PCR, and the adaptor primer 2 attached to the kit and primer 2 (SEQ ID NO: 15) for the second PCR, respectively. In the first PCR, the volume of the PCR solution was made up to a volume of 50 µl and the composition was as follows: 5 μl of template cDNA, 0.2 μM each of the primers, 0.2 mM dNTP, 1/50 volume of Advantage 2 Polymerase Mix (CLONTECH), and 1/10 volume of 10-fold condensed buffer. The cycle for amplification was performed by maintaining at 94° C. for 30 seconds, then repeating 5 times one cycle set to include 94° C. for 5 seconds and 72° C. for 3 minutes, 5 times 94° C. for 5 seconds and 70° C. for 3 minutes and 25 times one cycle set to include 94° C. for 5 seconds and 68° C. for 3 minutes, and maintaining at 72° C. for 10 minutes. In the second PCR, the PCR solution was made up to a volume of 50 μl and the composition was as follows: 5 μl of a 10-fold dilution of the first PCR reaction solution as a template, 0.2 μM each of the primers, 0.2 mM dNTP, 1/50 volume of Advantage 2 Polymerase Mix and 1/10 volume of 10-fold condensed buffer. The cycle for amplification was performed by maintaining at 94° C. for 2 minutes, then repeating 30 times one cycle set to include 94° C. for 30 seconds and 69° C. for 2 minutes and maintaining at 72° C. for 10 minutes. The reaction solution was subcloned to plasmid vector pCR2.1-TOPO using TOPO TA cloning kit (Invitrogen) and transfected to *Escherichia coli* DH5α-T1. The plasmid DNA was purified from the resulting transformant using QIAwell 8 Ultra Plasmid Kit (Qiagen). The reaction for base sequencing was carried out using BigDye Terminator Cycle Sequence Ready Reaction Kit (Perkin-Elmer). As a result of decoding on a fluorescent automatic sequencer, the base sequence represented by SEQ ID NO: 16, which is the partial sequence of cDNA at the 5' end, encoding rat-derived G protein-coupled receptor protein GPR34, was obtained.

REFERENCE EXAMPLE 5

Cloning of Full-Length Sequence for cDNA Encoding Rat-Derived G Protein-Coupled Receptor Protein GPR34

In order to obtain a putative sequence including the full length sequence for cDNA encoding rat-derived G protein-coupled receptor protein GPR34 predicted from the results of 5' and 3' RACE, primer 1 (SEQ ID NO: 17) and primer 2 (SEQ ID NO: 18) was designed and PCR was carried out. The solution for PCR was made up to a volume of 50 μl and was composed of 3 μl of rat spleen Marathon Ready cDNA (CLONTECH) as a template, 0.2 μM each of the primers, 0.2 mM dNTP, 0.5 M GC-Melt, 1/50 volume of Advantage-GC 2 Polymerase Mix (CLONTECH) and 1/5 volume of 5-fold condensed buffer. The cycle for amplification was performed by maintaining at 96° C. for 2 minutes, repeating 35 times one cycle set to include 96° C. for 30 seconds, 54° C. for 30 seconds and 72° C. for 60 seconds, and then maintaining at 72° C. for 10 minutes. Using TOPO TA cloning kit (Invitrogen), the reaction solution was subcloned to plasmid vector pCR2.1-TOPO and transfected to *Escherichia coli* DH5α-T1. From the resulting transformant, the plasmid DNA was purified using QIAwell 8 Ultra Plasmid Kit (Qiagen). The reaction for base sequencing was performed using BigDye Terminator Cycle Sequence Ready Reaction Kit (Perkin-Elmer). As a result of decoding on a fluorescent automatic sequencer, the base sequence represented by SEQ ID NO: 21 was obtained. This sequence contained the base sequence (SEQ ID NO: 20) of cDNA encoding the full-length amino acid sequence (SEQ ID NO: 19) of rat-derived G protein-coupled receptor protein GPR34. Using this plasmid, *Escherichia coli* DH5α-T1 was transfected to acquire *Escherichia coli* DH5α-T1/pCR2.1-TOPO-ratGPR34.

REFERENCE EXAMPLE 6

Chemotaxis Stimulating Activity of Human-Derived GPR34-Expressed CHO Cells by Lysophosphatidylserine The chemotaxis stimulating activity of lysophosphatidylserine on human-derived GPR34-expressed CHO cells prepared by the procedure described in REFERENCE EXAMPLE 1 was assayed as follows.

Chemotaxis assay was conducted using a 96-well chemotaxis chamber (Neuro Probe). Polycarbonate frame filter (Neuro Probe) with a pore size of 5 μm was immersed in 10 μg/ml of bovine fibronectin (Yagai Research Center) diluted with PBS at room temperature for 10 minutes and then air-dried for pre-treatment. Human GPR34-expressed CHO cells were scraped off by trypsin-EDTA (GIBCO), the medium was replaced by DMEM (Nikken Seibutsu Kagaku Kenkyusho) and the cells were resuspended to prepare $1 \times 10^6$ cells/ml of cell suspension. In a lower chamber of 96-well chemotaxis chamber, 37 μl of lysophosphatidylserine solutions with various concentrations in DMEM were charged, and the human-derived GPR34-expressed CHO cell suspension prepared in $1 \times 10^6$ cells/ml was charged in an upper chamber in 200 μl/well ($2 \times 10^5$ cells/well). After incubation for 5 hours in a $CO_2$ incubator, the cells which that did not migrate from the top of the filter were scraped with Kimwipe (CRECIA) and the CHO cells that migrated to the bottom of the filter were immobilized and stained with Diff-Quick (International Reagents Corp.). Absorbance at 595 nm was measured with a plate reader.

Figure 5:
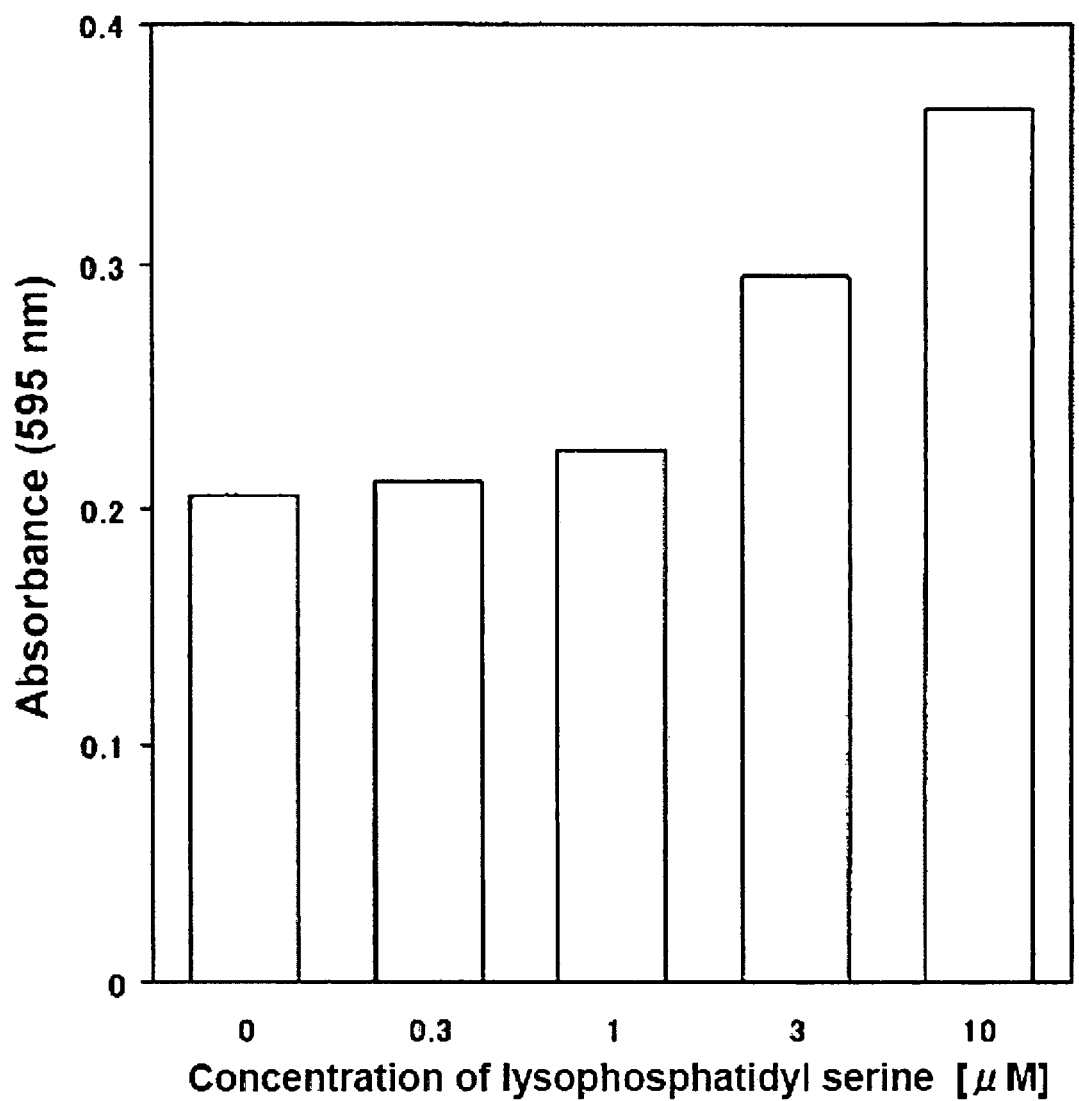
FIG. 5 shows chemotaxis-stimulating activities of lysophosphatidylserine on GPR34-expressed CHO cells.

FIG. 5 shows the chemotaxis stimulating activity of lysophosphatidylserine on human-derived GPR34-expressed CHO cells in concentrations of 0, 0.3, 1, 3 and 10 μM, in terms of absorbance at 595 nm.

The results reveal that human-derived GPR34-expressed CHO cells exhibit the chemotaxis activity in response to lysophosphatidylserine. The chemotaxis activity was confirmed with 1 μM or higher, increased dependently on the concentration of lysophosphatidylserine and showed the maximum chemotaxis activity in 10 μM. The $EC_{50}$ value of the chemotaxis activity was about 2.5 μM.

REFERENCE EXAMPLE 7

(7-1) Synthesis of 1-[9,10-$^3H_2$]-steraroyl-sn-glycero-3-phospho-L-serine (1-[9,10-$^3H_2$]-stearoyl-lysophosphatidylserine)

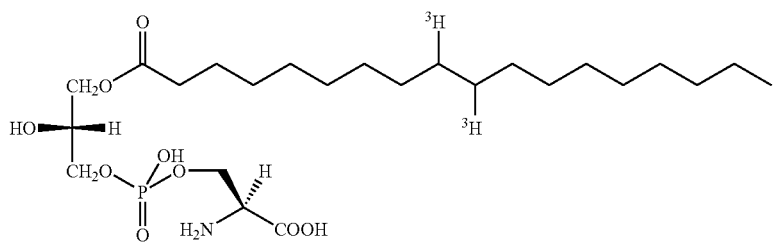

In order to study the binding test using lysophosphatidylserine and GPR34-expressed CHO cell membrane fraction, $^3$H-labeled lysophosphatidylserine was synthesized as follows.

First, 1-oleoyl-sn-glycero-3-phospho-L-serine (1-oleoyl-lysophosphatidylserine) having double bond was prepared for $^3$H labeling by catalytic hydrogenation.

After 1,2-dioleoyl-sn-glycero-3-phospho-L-serine sodium salt (SIGMA, P1060) (85 mg) was dissolved in distilled water (25 ml), 200 mM Tris-HCl buffer (pH 8.0) (1.5 ml) and 100 mM potassium chloride (1.5 ml) were added to the solution, and phospholipase A2 (0.3 ml) (10 mg/ml, 5 mM sodium acetate buffer (pH 5.0)) was further added thereto. The mixture was reacted at room temperature for 20 hours, and the pH was rendered 2 to 3 with 5M hydrochloric acid to terminate the reaction. After the reaction solution was concentrated to dryness, the residue was dissolved in a chloroform-methanol solvent mixture and the solution was adsorbed on silica gel column chromatography. Elution was performed with a chloroform-methanol solvent mixture to give 1-oleoyl-sn-glycero-3-phospho-L-serine. Subsequently, 1-oleoyl-sn-glycero-3-phospho-L-serine was catalytically hydrogenated with gaseous tritium ($3H_2$) in the presence of palladium, in accordance with methods publicly known (e.g., the methods described in R. F. Glascock, Isotopic Gas Analysis for Biochemists, 227, Academic Press, New York, 1954) to introduce tritium into the double bond. Thus, the objective product, 1-[9,10-$^3$H2]-stearoyl-sn-glycero-3-phospho-L-serine was obtained.

(7-2) Preparation of Human-Derived GPR34-Expressed CHO Cell Membrane Fraction

Human-derived GPR34-expressed CHO cells prepared by a modification of the procedure described in REFERENCE EXAMPLE 1 were incubated. Then, 10 ml of homogenate buffer (10 mM NaHCO$_3$, 5 mM EDTA (ethylenediaminetetraacetate), 0.5 mM PMSF (phenylmethanesulfonyl fluoride), 1 µg/ml pepstatin, 4 µg/ml E64, 20 µg/ml leupeptin) was added to 1×10$^8$ of the cells, followed by homogenization using a polytron (12,000 rpm, 1 minute). The cell homogenate was centrifuged (1,000 g, 15 minutes) to give the supernatant. Next, the supernatant was subjected to ultracentrifugation (Beckman type 30 rotor, 30,000 rpm, 1 hour) to give human-derived GPR34-expressed CHO cell membrane fraction as precipitates.

(7-3) Receptor Binding Test Using 1-[9,10-$^3$H$_2$]-stearoyl-sn-glycero-3-phospho-L-serine (Hereinafter Abbreviated as [$^3$H]-lysoPS) and Human-Derived GPR34-Expressed CHO Cell Membrane Fraction The cell membrane fraction prepared in (7-2) described above was diluted to various concentrations in assay buffer (25 mM Tris-HCl, 5 mM EDTA, 0.05% CHAPS (3-[(3-cholamidopropyl)dimethylammonio]-1-propanesulfat-e), 0.1% BSA, 0.5 mM PMSF, 1 µg/ml pepstatin, 20 µg/ml leupeptin, 4 µg/ml E-64, pH 7.4) and a 200 µl aliquot of the dilution was dispensed in a polypropylene-made test tube (Falcon 2053). In order to measure the maximum binding level, 2 µl of DMSO and 2 µl of 80 nM [$^3$H]-lysoPS were added to the membrane fraction solution. Further in order to measure non-specific binding, 2 µl of a solution of 10 mM lysophosphatidylserine in DMSO and 2 µl of 80 nM [$^3$H]-lysoPS were added to the membrane fraction solution. After reacting at 25° C. for 75 minutes, the reaction solution was suction filtered using Whatman glass filter (GF-F) treated with polyethyleneimine, and the filter was further washed twice with 1.5 ml of wash buffer (25 mM Tris-HCl, 5 mM EDTA, 0.05% CHAPS, 0.1% BSA, pH 7.4). After filtration, the radioactivity remained on the filter paper was measured with a scintillation counter. The specific binding (SB) was estimated by subtracting the radioactivity of the non-specific binding from the radioactivity (TB) for the maximum binding.

(7-4) Screening of Compound that Changes Binding Properties of GPR34 to Lysophosphatidylserine by Receptor Binding Test In (7-3) described above, 2 µl of the DMSO solution of a test compound and 2 µl of 80 nM [$^3$H]-lysoPS were added to the membrane fraction solution. After the mixture was reacted at 25° C. for 75 minutes, the reaction solution was suction filtered through Whatman glass filter (GF-F) treated with polyethyleneimine, and the filter was further washed twice with 1.5 ml of wash buffer (25 mM Tris-HCl, 5 mM EDTA, 0.05% CHAPS, 0.1% BSA, pH 7.4). After filtration, the radioactivity remained on the filter paper was measured with a scintillation counter. When this radioactivity is made X, the binding inhibitory activity of the test compound is expressed by (TB−X)/SB×100(%).

With respect to the test compounds showing the binding inhibitory activity, the 50% inhibitory concentration (IC$_{50}$ value) can be determined by assaying the binding inhibitory activity using the test compounds prepared in various concentrations. The compound which give a lower IC$_{50}$ value are selected as compounds which inhibit the binding of GPR34 to lysophosphatidylserine more potently.

On the other hand, the compounds which give negative values in the binding inhibitory activity are selected as the compounds that promote the binding of GPR34 to lysophosphatidylserine.

EXAMPLE 13

(1) Identification of GPR34 Gene Expression Cells in Rat Brain/Spinal Cord Tissue sections For analysis of expression in rat central nervous system, GPR34 cRNA probe and frozen sections of the brain/spinal cord were prepared and processed for in situ hybridization (ISH). First, GPR34 cRNA probe was prepared as follows. Full length rat GPR34 was cloned into plasmid (pGEM-9Zf (−), Promega) with a dual promoter by TA cloning. It was confirmed that the inserts were all inserted in a reverse direction. Using Advantage cDNA PCR-Kit (Clontech), the insert bearing Sp6/T7 promoter was amplified by PCR with M13 primer and purified by ethanol precipitation. Using as a template 1 µg taken from the product, reverse transcription was performed (40 µl scale, 37° C. for 2 hours) with In vitro Transcription Kit (Roche). After ethanol precipitation, the product was dissolved in 100 µl of distilled water to give cRNA probe. In this case, the reverse transcription product by T7 and the reverse transcription product by Sp6 were made an anti-sense probe and a sense probe, respectively. The frozen section was prepared as follows. Brain/spinal cord were removed from Wistar male adult rat and embedded in O.C.T. compound (SAKURA) with liquid nitrogen. Then, the brain/spinal cord was sliced on Cryostat CM3050 (Leica) MAS-coated slide glass (Matsunami) to prepare the frozen section of 12 µm. The frozen section prepared was fixed in ¹⁄₁₅M phosphate buffer, pH 7.4 (Wako Pure Chemicals) containing 4% PFA. After washing 3 times in PBS, the section was immersed in 0.1M triethanolamine containing 0.25% acetic anhydride at room temperature for 10 minutes. After washing 3 times in PBS and then denaturation at 85° C. for 10 minutes, ice-chilled probe/hybridization buffer (¹⁄₂₀₀) was dropwise added in a volume of 60 µl (covered with a parafilm), followed by hybridization overnight at 60° C. in a moisture chamber charged with 50% formamide. Subsequently, the following procedure was carried out to wash the probe hybridized non-specifically: 1) treatment with 2×SSC (SSC; 1×SSC=150 mM NaCl, 15 mM sodium citrate, pH 7.0)/50% formamide (60° C. for 30 minutes, once), 2) 2×SSC treatment (60° C. for 20 minutes, once), 3) 0.1×SSC treatment (60° C. for 20 minutes, twice). After the foregoing treatments were performed, immunohistochemistry was applied to detect the DIG-labeled probe. First, after washing in DIG-1 (100 mM Tris-HCl pH 7.5, 150 mM NaCl, 0.1% Tween 20), non-specific reaction was blocked by treatment (at room temperature for an hour) with DIG-1 containing 1.5% Blocking Reagent (Roche), and DIG-1 (1:1000) containing anti-DIG fab-fragment antibody conjugated with alkaline phosphatase (Roche) was reacted at room temperature for an hour. After thoroughly washing with DIG-1, the tissue was rinsed with DIG-3 (100 mM Tris-HCl, pH 9.5, 100 mM NaCl, 50 mM $MgCl_2$), followed by color-forming reaction overnight at room temperature in 3% polyvinyl alcohol (Wako Pure Chemicals, #165-17915) containing 0.63 μg/ml 5-bromo-4-chloro-3-indolyl-phosphate (BCIP) and 1.53 μg/ml 4-nitroblue tetrazolium (NBT). After the color formation was appropriately terminated by washing with running water, the tissue was sealed in 90% glycerol/PBS and observed with an optical microscope.

As a result, a positive signal sporadically occurring in the whole brain/spinal cord was observed. The GPR34 positive cells were sporadically present with about 50 μm spacing and observed also in the molecular layer of brain or the white matter of spinal cord where no neuron was present. It is thus considered that the positive cells would be microglia.

(2) Analysis of GPR34 Gene Expression in Rat Primary Culture Microglial Cells (PMGC)

Preparation of Rat PMGC

Wistar newborn rats (1-2 days after birth) (Charles River Japan) were decapitated and from the brain removed meninges were stripped under stereomicroscope while ice-cooling in PBS(−). The brain was minced with scissors. The minced brain was transferred to a 50 mL Falcon tube/PBS(−) (Invitrogen 14190-144) and pipetted with a 10 mL pipette until no mass was observed, followed by straining through a cell strainer (Falcon 352360). After centrifugation (1000 rpm, 10 mins.), the supernatant was removed and culture medium was added thereto. The mixture was gently pipetted. The culture medium was made up in a final concentration of 10% of FCS (Invitrogen 16140-071) by adding 1/100 volume of penicillin-streptomycin (Invitrogen) to DMEM (Invitrogen 11995-073). The culture medium was dispensed into 75 cm2 pol-D-Lysin Coat Flask (Falcon 356537) in 2 brain/20 mL/flask, followed by incubating at 37° C. in 5% $CO_2$ incubator for 10 to 20 days. The medium was exchanged every about 3 days. After 10 to 20 days the flask was tapped gently, and the culture medium containing the liberated cells was transferred to a 50 mL Falcon tube and centrifuged (1000 rpm, 10 mins.) to collect the cells (collect them again every 3 days). The cell number was counted and plated on a 24-well plate (Falcon 353047) at 5E+5 cells/well. The supernatant was removed 30 minutes after and the culture medium was added thereto (to retain highly adherent microglia). After incubation in an O/N medium, the cells were used for RNA extraction or assay. Using RNeasy Mini Kit (Qiagen), total RNA was extracted from the obtained cells according to the protocol attached. The total RNA obtained was concentrated using Ethachinmate and dissolved in RNase-free $H_2O$ in accordance with the protocol attached. Next, using 0.1 μg of the total RNA, reverse transcription was performed using SuperScript II ReverseTranscriptase (Invitrogen) by the following procedure to prepare single-stranded cDNA. To the total RNA solution 0.05 μg of random primer (Invitrogen) and RNase-free H2O were added to make the total volume 11 μL and the mixture was incubated at 70° C. for 10 minutes followed by ice cooling for 1 minute. After 4 μL of 5× First-Strand Buffer (attached to SuperScript II ReverseTranscriptase), 1 μL of 10 mM dNTP (Invitrogen), 2 μL of 0.1M DTT (attached to SuperScript II ReverseTranscriptase), 1 μL of RNaseOUT (Invitrogen) and 1 μL of SuperScript II ReverseTranscriptase wee added, the mixture was incubated at 42° C. for 50 minutes and at 70° C. for 15 minutes, which was then ice cooled for 5 minutes. The thus obtained cDNA was purified using Ethachinmate and dissolved in Tris-EDTA Buffer (Fluka) in accordance with the protocol attached. Primers (SEQ ID NOS: 37 and 38) for quantification of GPR34 and standard (SEQ ID NO: 39) were used in TaqMan PCR. TaqMan PCR was performed on each sample at n=2 in a volume of 15 μl using 1.25 ng of the total RNA as a template. The reaction solution was composed of 900 nM primers, 250 nM probe and ½ volume (equivalent to 100 ng of the template RNA) of TaqMan Universal PCR Master Mix (Applied Systems). The reaction and analysis were performed using ABI PRISM 7700 Sequence Detection System (Applied Systems). The reaction was carried out, after maintaining at 50° C. for 2 minutes and then at 95° C. for 10 minutes, by repeating 40 times the cycle set to include 95° C. for 15 seconds and 60° C. for 1 minute. The gene expression level was determined by analysis of a standard curve to set Y-Slope at 38-42 and correlation coefficients at 0.995 or more.

As a result, the expression level of rat GPR34 gene/25 ng total RNA was 3990 copies in the whole brain, whereas the expression level was 74625 copies in PMGC. These results coupled with the results of ISH reveal that GPR34 was expressed mainly in microglial cells in the central nervous system.

EXAMPLE 14

Reactivity of Microglial Cells by Addition of lysoPS

The reactivity of rat primary culture microglial cells (PMGC) with lysoPS was examined using FLIPR. PMGC was incubated in DMEM (Invitrogen) supplemented with 10% calf fetal serum (Invitrogen), unless otherwise indicated. PMGC, which was prepared from the brain of rat of one day old one day before assay, was plated on a Black walled 96-well plate (Costar) at $5.0 \times 10^4$ cells/well, and incubated overnight at 37° C. in a $CO_2$ incubator adjusted to 5% $CO_2$. After lysoPS was added to the PMGC, changes of intracellular calcium levels in this case were assayed using FLIPR (Molecular Device). To assay the changes of intracellular calcium levels on FLIPR, the following pretreatment was performed. First, an assay buffer was prepared to incorporate fluorescent dye Fluo-3AM (DOJIN) in the cells or wash the cells immediately before the FLIPR assay. To a solution of 20 ml of 1M HEPES (pH 7.4) (DOJIN) to 1000 ml of HBSS (Invitrogen) (hereinafter, HBSS/HEPES solution), 10 ml of the solution mixture obtained by dissolving 710 mg of Probenecid (Sigma) in 5 ml of 1N NaOH and further adding 5 ml of the HBSS/HEPES solution thereto was added. The resulting solution was used as an assay buffer. Next, 50 μg of Fluo-3AM was dissolved in 21 μl of DMSO (DOJIN) and an equal volume of 20% Pluronic acid (Molecular Device) was further mixed therewith. The resulting mixture was 10.6 ml of the assay buffer supplemented with 105 μl of calf fetal serum to prepare the fluorescent dye solution.

The medium of PMGC which underwent transfection treatment was removed and 100 μl each/well of the fluorescent dye solution was dispensed in a 96-well plate, followed by incubating in a $CO_2$ incubator for an hour to incorporate the fluorescent dye into the cells. The cells after incubation were washed in the assay buffer described above and set in FLIPR. Test samples added to PMGC were prepared using the assay buffer and set in FLIPR at the same time. Following the foregoing pretreatment, changes in intracellular calcium levels after addition of various test samples were assayed on FLIP.

As a result, it was found that when 0.2 to 10 μM lysoPS was added, PMGC responded concentration-dependently (increase in intracellular calcium levels). Such a response was not observed under the conditions where GPR34 antagonist was added. That is, it became clear that lysoPS has the action of increasing the intracellular calcium levels via GPR34. In addition, the phosphorylation of ERK1/2 observed in mast cells was also noted in PMGC. These results strongly suggest that some functions associated with the growth/differentiation of microglial cells will be activated by stimulation with lysoPS.

EXAMPLE 15

Anti-Inflammatory Action of lysoPS in PMGC

In order to examine the action of lysoPS on the activation of microglia, actions induced by the addition of lysoPS in PMGC activated by LPS stimulation was examined in the presence of IFN-α. PMGC, which was prepared from the brain of rat of one day old on the preceding day, was plated on a 24-well plate (Falcon 353047) at 50000 cells/well, and IFN-α (1 ng/ml, Biovision) was added 6 hours after. On the following day, lysoPS (5 μM) was added upon stimulation by LPS (1 μg/ml), and comparison was made between the presence and absence of lysoPS if cytokine production was affected. RNA was prepared as in the procedure described in EXAMPLE 4 for 2 and 8 hours after addition or without addition of LPS and lysoPS (5 μM). The sequencing information of the primers, probe and standard used for TaqMan are as described above. The cytokine production was compared by TaqMan PCR in terms of changes in expression levels of cytokine genes.

As a result, a tendency to suppress the expression of inflammatory cytokines IL-6 and TNF-α was noted 2 hours after the addition, whereas in anti-inflammatory cytokine IL-10, a tendency to increase its expression was noted 8 hours after. This tendency was similarly observed by the addition or non-addition of lysoPS (5 μM) when INF-α (1 ng/ml) and LPS (1 μg/ml) were added at the same time. These results reveal that lysoPS has an anti-inflammatory activity.

INDUSTRIAL APPLICABILITY

The present invention provides a screening method and screening kit for interleukin-13 production inhibitors, etc. using GPR34 or mast cells and a ligand of GPR34; interleukin-13 production inhibitors, etc., which are obtainable using the screening method or kit. The IL-13 production inhibitors which are obtainable by screening of the present invention are useful as prophylactic/therapeutic agents for, e.g., respiratory diseases, etc. The present invention further provide a screening method or screening kit for eicosanoid production inhibitors, degranulation inhibitors of mast cells, growth inhibitors of mast cells, etc., using GPR34 or mast cells and the ligand of GPR34; eicosanoid production inhibitors, degranulation inhibitors of mast cells, growth inhibitors of mast cells, etc., which are obtainable using the screening method or kit. Furthermore, the present invention also provides a screening method or screening kit for prophylactic/therapeutic agents for central nervous disorders, using microglial cells and the ligand of GPR34, prophylactic/therapeutic agents for central nervous disorders, etc., which are obtainable by the screening method or kit.

The invention claimed is:

1. A method for screening an IL-13 production inhibitor, which comprises (A) contacting a receptor protein represented by the amino acid of SEQ ID NO: 1 and having a ligand binding activity, or a salt thereof; with a ligand compound which is lysophosphatidyl-L-serine, or a salt thereof;
   (B) contacting the receptor protein or a salt thereof with the ligand compound and a test compound;
   (C) measuring the binding amounts of the ligand compound to the receptor protein in (A) and (B); and
   (D) comparing the binding amounts in (A) and (B), wherein greater binding in (A) compared to (B) is indicative of an IL-13 production inhibitor, thereby screening an IL-13 production inhibitor.

2. A method for screening an IL-13 production inhibitor, which comprises:
   (A) contacting a mast cell with a ligand compound which is lysophosphatidyl-L-serine, or a salt thereof;
   (B) contacting the mast cell with the ligand compound and a test compound; and
   (C) measuring the binding amounts of the ligand compound to the mast cell in (A) and (B); and
   (D) comparing the binding amounts in (A) and (B), wherein greater binding in (A) compared to (B) is indicative of an IL-13 production inhibitor, thereby screening an IL-13 production inhibitor.

3. A method for screening an IL-13 production inhibitor, which comprises (A) contacting a receptor protein represented by the amino acid of SEQ ID NO: 1 and having a ligand binding activity, or a salt thereof; with a ligand compound which is lysophosphatidyl-L-serine, or a salt thereof;
   (B) contacting the receptor protein or a salt thereof with the ligand compound and a test compound;
   (C) measuring cell stimulating activities in (A) and (B); and
   (D) comparing the cell stimulating activities in (A) and (B), wherein greater activity in (A) compared to (B) is indicative of an IL-13 production inhibitor, thereby screening an IL-13 production inhibitor.

4. A method for screening an IL-13 production inhibitor, which comprises:
   (A) contacting a mast cell with a ligand compound which is lysophosohatidyl-L-serine, or a salt thereof;
   (B) contacting the mast cell with the ligand compound and a test compound; and
   (C) measuring cell stimulating activities in (A) and (B); and
   (D) comparing the cell stimulating activities in (A) and (B), wherein greater activity in (A) compared to (B) is indicative of an IL-13 production inhibitor, thereby screening an IL-13 production inhibitor.

5. The screening method according to any one of claim 1, 2, 3 or 4, wherein the IL-13 production inhibitor is a therapeutic agent for an immune disease, a respiratory disease, a urologic disease or a circulatory disease.

* * * * *

```
                        SEQUENCE LISTING

<160> NUMBER OF SEQ ID NOS: 55

<210> SEQ ID NO 1
<211> LENGTH: 381
<212> TYPE: PRT
<213> ORGANISM: Homo sapiens

<400> SEQUENCE: 1

Met Arg Ser His Thr Ile Thr Met Thr Thr Thr Ser Val Ser Ser Trp
1               5                   10                  15

Pro Tyr Ser Ser His Arg Met Arg Phe Ile Thr Asn His Ser Asp Gln
            20                  25                  30

Pro Pro Gln Asn Phe Ser Ala Thr Pro Asn Val Thr Thr Cys Pro Met
        35                  40                  45

Asp Glu Lys Leu Leu Ser Thr Val Leu Thr Thr Ser Tyr Ser Val Ile
    50                  55                  60

Phe Ile Val Gly Leu Val Gly Asn Ile Ile Ala Leu Tyr Val Phe Leu
65                  70                  75                  80

Gly Ile His Arg Lys Arg Asn Ser Ile Gln Ile Tyr Leu Leu Asn Val
                85                  90                  95

Ala Ile Ala Asp Leu Leu Leu Ile Phe Cys Leu Pro Phe Arg Ile Met
            100                 105                 110
```

Tyr His Ile Asn Gln Asn Lys Trp Thr Leu Gly Val Ile Leu Cys Lys
            115                 120                 125
Val Val Gly Thr Leu Phe Tyr Met Asn Met Tyr Ile Ser Ile Ile Leu
130                 135                 140
Leu Gly Phe Ile Ser Leu Asp Arg Tyr Ile Lys Ile Asn Arg Ser Ile
145                 150                 155                 160
Gln Gln Arg Lys Ala Ile Thr Thr Lys Gln Ser Ile Tyr Val Cys Cys
                165                 170                 175
Ile Val Trp Met Leu Ala Leu Gly Gly Phe Leu Thr Met Ile Ile Leu
            180                 185                 190
Thr Leu Lys Lys Gly His Asn Ser Thr Met Cys Phe His Tyr Arg
        195                 200                 205
Asp Lys His Asn Ala Lys Gly Glu Ala Ile Phe Asn Phe Ile Leu Val
        210                 215                 220
Val Met Phe Trp Leu Ile Phe Leu Leu Ile Ile Leu Ser Tyr Ile Lys
225                 230                 235                 240
Ile Gly Lys Asn Leu Leu Arg Ile Ser Lys Arg Ser Lys Phe Pro
                245                 250                 255
Asn Ser Gly Lys Tyr Ala Thr Thr Ala Arg Asn Ser Phe Ile Val Leu
            260                 265                 270
Ile Ile Phe Thr Ile Cys Phe Val Pro Tyr His Ala Phe Arg Phe Ile
        275                 280                 285
Tyr Ile Ser Ser Gln Leu Asn Val Ser Ser Cys Tyr Trp Lys Glu Ile
        290                 295                 300
Val His Lys Thr Asn Glu Ile Met Leu Val Leu Ser Ser Phe Asn Ser
305                 310                 315                 320
Cys Leu Asp Pro Val Met Tyr Phe Leu Met Ser Ser Asn Ile Arg Lys
                325                 330                 335
Ile Met Cys Gln Leu Leu Phe Arg Arg Phe Gln Gly Glu Pro Ser Arg
            340                 345                 350
Ser Glu Ser Thr Ser Glu Phe Lys Pro Gly Tyr Ser Leu His Asp Thr
        355                 360                 365
Ser Val Ala Val Lys Ile Gln Ser Ser Ser Lys Ser Thr
        370                 375                 380

<210> SEQ ID NO 2
<211> LENGTH: 1143
<212> TYPE: DNA
<213> ORGANISM: Homo sapiens

<400> SEQUENCE: 2
atgagaagtc ataccataac aatgacgaca acttcagtca gcagctggcc ttactcctcc    60
cacagaatgc gctttataac caatcatagc gaccaaccgc acaaaacttt ctcagcaaca   120
ccaaatgtta ctacctgtcc catggatgaa aaattgctat ctactgtgtt aaccacatcc   180
tactctgtta ttttcatcgt gggactggtt ggaacataa tcgccctcta tgtatttctg    240
ggtattcacc gtaaaagaaa ttccattcaa atttatctac ttaacgtagc cattgcagac   300
ctcctactca tcttctgcct cccttttccga ataatgtatc atattaacca aaacaagtgg   360
acactaggtg tgattctgtg caaggttgtg ggaacactgt tttatatgaa catgtacatt   420
agcattattt tgcttggatt catcagtttg gatcgctata taaaaattaa tcggtctata   480
cagcaacgga aggcaataac aaccaaacaa gtatttatg tctgttgtat agtatggatg    540
cttgctcttg gtggattcct aactatgatt attttaacac ttaagaaagg agggcataat    600

-continued

```
tccacaatgt gtttccatta cagagataag cataacgcaa aaggagaagc cattttaac    660 ttcattcttg tggtaatgtt ctggctaatt ttcttactaa taatcctttc atatattaag    720
attgggaaga atctattgag gatttctaaa aggaggtcaa aatttcctaa ttctggtaaa    780
tatgccacta cagctcgtaa ctcctttatt gtacttatca tttttactat atgttttgtt    840
ccctatcatg cctttcgatt catctacatt tcttcacagc taaatgtatc atcttgctac    900
tggaaagaaa ttgttcacaa aaccaatgag atcatgctgg ttctctcatc tttcaatagt    960
tgcttagatc cagtcatgta tttcctgatg tccagtaaca ttcgcaaaat aatgtgccaa   1020
cttcttttta gacgatttca aggtgaacca gtaggagtg aaagcacttc agaatttaaa   1080
ccaggatact ccctgcatga tacatctgtg gcagtgaaaa tacagtctag ttctaaaagt   1140
act                                                                1143

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atctgtcgac atgagaagtc ataccat                                        27

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tatgactagt tcaagtactt ttagaactag                                     30

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tcagtcagca gctggcctta                                                20

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggcggttggt cgctatga                                                  18

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 7
tcctcccaca gaatgcgctt tataacca                                      28

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
taaattctga agtgctttca                                               20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
attcaccgta aaagaaattc                                               20

<210> SEQ ID NO 10
<211> LENGTH: 749
<212> TYPE: DNA
<213> ORGANISM: Rattus norvegicus

<400> SEQUENCE: 10
ggctgttgca gaccttctac tcatcttctg cctcccttc cgcataatgt atcacatcaa    60
ccaaaatagg tggacactag gtgtgattct ttgcaaagtt gtggggacac tattttacat   120
gaacatgtac attagtatta ttctgcttgg gtttatcagt ttggatcgat atataaaaat   180
caaccggtct atacaacaaa gaagggcaat aaccaccaag caaagtgttt acgtttgctg   240
tgtagtctgg acagttgctc tagctggatt tttaacaatg atcattttga cactgaagaa   300
gggagggcac aattccacaa tgtgtttcca ttacagagat aagcataatg caaagggaga   360
agcgatcttt aactttgctc ttgtagtaat gttctggctc attttcctac tgataatcct   420
ttcatatatt aagattggca agaatctact gaggatttct aaaaggaggt caaaatttcc   480
taactctggc aaatatgcca cgacagcccg gaactcctc attgtactaa tcattttac    540 tatatgcttc gtgccttatc atgcctttcg attcatttac atttcttcac agctaaatgc   600
atcttcttgc tactggaagg aaatcattca taaaaccaat gagatcatgt tggttctctc   660
ctctttcaac agctgcttgg atcctgtcat gtatttccta atgtccagta atattcgcaa   720
aatcatgtgt caacttcttt ttagaagat                                    749

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcttcgtgcc ttatcatgcc tttcg                                         25

<210> SEQ ID NO 12

```
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctctcctctt tcaacagctg cttgg                                           25

<210> SEQ ID NO 13
<211> LENGTH: 300
<212> TYPE: DNA
<213> ORGANISM: Rattus norvegicus

<400> SEQUENCE: 13
ttcaaagtga cacaagcaga agtgaaagca cttcagaatt taagccagga tattccttgc     60
atgatctatc tgtgacggtc aaaatgcagt acagcactaa gggtaactga ggcacatgca    120
gtaaaatgaa caacataaac cagcctcttc attccttgag gttggtaaaa ttatggaaca    180
aattcctagc atgttcaaaa accagatctt tagaagtggt ctttcacttg cttaactgca    240
aaatagttca aggcaaagaa aagcttacac taatccctag attttagaac tatatgtaga    300

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcccttcttt gttgtataga ccgg                                            24

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcaaagaatc acacctagtg tccacc                                          26

<210> SEQ ID NO 16
<211> LENGTH: 500
<212> TYPE: DNA
<213> ORGANISM: Rattus norvegicus

<400> SEQUENCE: 16
cggatggaag agtccagctg acacgacctg gtcgagggag ctttgggttt cctcctttac     60
ttcagcaaag cctcaactca gttcctgtga cttctgaagt atggcctgaa tagattcaat    120
cattattagt ccattatcat ataggaaaat ctgaagacac caagaagtat aaaaagcatg    180
tcatttagca ccctgtcctg atagttacag aagacattga gaagttacag tgtaacaatg    240
acgactacag ttgacagctg gctttgctcc tctcctggaa tgcactttat aactaatgac    300
agtgaccaag tctcacaaaa tttctcagga gtgtcaaatg tcactagctg tccaatggat    360
gaaaaattac tgtctactgt gttaacaact ttctactctg tgatattcat cgtgggactg    420
gttggaaaca tcattgccct ttatgtattt ctgggcatcc accgcaaaag aaattccatt    480
caaatttatc tacttaatgt                                                500
```

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
tcagttaccc ttagtgctgt                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
atgacgacta cagttgacag                                              20

<210> SEQ ID NO 19
<211> LENGTH: 373
<212> TYPE: PRT
<213> ORGANISM: Rattus norvegicus

<400> SEQUENCE: 19

Met Thr Thr Thr Val Asp Ser Trp Leu Cys Ser Ser Pro Gly Met His
1               5                   10                  15

Phe Ile Thr Asn Asp Ser Asp Gln Val Ser Gln Asn Phe Ser Gly Val
            20                  25                  30

Ser Asn Val Thr Ser Cys Pro Met Asp Glu Lys Leu Leu Ser Thr Val
        35                  40                  45

Leu Thr Thr Phe Tyr Ser Val Ile Phe Ile Val Gly Leu Val Gly Asn
    50                  55                  60

Ile Ile Ala Leu Tyr Val Phe Leu Gly Ile His Arg Lys Arg Asn Ser
65                  70                  75                  80

Ile Gln Ile Tyr Leu Leu Asn Val Ala Val Ala Asp Leu Leu Leu Ile
                85                  90                  95

Phe Cys Leu Pro Phe Arg Ile Met Tyr His Ile Asn Gln Asn Arg Trp
            100                 105                 110

Thr Leu Gly Val Ile Leu Cys Lys Val Val Gly Thr Leu Phe Tyr Met
        115                 120                 125

Asn Met Tyr Ile Ser Ile Ile Leu Leu Gly Phe Ile Ser Leu Asp Arg
    130                 135                 140

Tyr Ile Lys Ile Asn Arg Ser Ile Gln Gln Arg Arg Ala Ile Thr Thr
145                 150                 155                 160

Lys Gln Ser Val Tyr Val Cys Cys Val Val Trp Thr Val Ala Leu Ala
                165                 170                 175

Gly Phe Leu Thr Met Ile Ile Leu Thr Leu Lys Lys Gly Gly His Asn
            180                 185                 190

Ser Thr Met Cys Phe His Tyr Arg Asp Lys His Asn Ala Lys Gly Glu
        195                 200                 205

Ala Ile Phe Asn Phe Ala Leu Val Val Met Phe Trp Leu Ile Phe Leu
    210                 215                 220

Leu Ile Ile Leu Ser Tyr Ile Lys Ile Gly Lys Asn Leu Leu Arg Ile
225                 230                 235                 240

```
Ser Lys Arg Arg Ser Lys Phe Pro Asn Ser Gly Lys Tyr Ala Thr Thr
            245                 250                 255

Ala Arg Asn Ser Phe Ile Val Leu Ile Ile Phe Thr Ile Cys Phe Val
        260                 265                 270

Pro Tyr His Ala Phe Arg Phe Ile Tyr Ile Ser Ser Gln Leu Asn Ala
    275                 280                 285

Ser Ser Cys Tyr Trp Lys Glu Ile Ile His Lys Thr Asn Glu Ile Met
290                 295                 300

Leu Val Leu Ser Ser Phe Asn Ser Cys Leu Asp Pro Val Met Tyr Phe
305                 310                 315                 320

Leu Met Ser Ser Asn Ile Arg Lys Ile Met Cys Gln Leu Leu Phe Arg
                325                 330                 335

Arg Phe Gln Ser Asp Thr Ser Arg Ser Glu Ser Thr Ser Glu Phe Lys
            340                 345                 350

Pro Gly Tyr Ser Leu His Asp Leu Ser Val Thr Val Lys Met Gln Tyr
        355                 360                 365

Ser Thr Lys Gly Asn
    370
```

<210> SEQ ID NO 20
<211> LENGTH: 1119
<212> TYPE: DNA
<213> ORGANISM: Rattus norvegicus

<400> SEQUENCE: 20

```
atgacgacta cagttgacag ctggctttgc tcctctcctg gaatgcactt tataactaat      60
gacagtgacc aagtctcaca aaatttctca ggagtgtcaa atgtcactag ctgtccaatg     120
gatgaaaaat tactgtctac tgtgttaaca actttctact ctgtgatatt catcgtggga     180
ctggttggaa acatcattgc cctttatgta tttctgggca tccaccgcaa aagaaattcc     240
attcaaattt atctacttaa tgtggctgtt gcagaccttc tactcatctt ctgcctccct     300
ttccgcataa tgtatcacat caaccaaaat aggtggacac taggtgtgat tcttttgcaaa    360
gttgtgggga cactatttta catgaacatg tacattagta ttattctgct tgggtttatc     420
agtttggatc gatatataaa aatcaaccgg tctatacaac aaagaagggc aataaccacc     480
aagcaaagtg tttacgtttg ctgtgtagtc tggacagttg ctctagctgg attttttaaca    540
atgatcattt tgacactgaa gagggaggg cacaattcca caatgtgttt ccattacaga      600
gataagcata tgcaaagggg agaagcgatc tttaactttg ctcttgtagt aatgttctgg     660
ctcattttcc tactgataat cctttcatat attaagattg gcaagaatct actgaggatt     720
tctaaaagga ggtcaaaatt tcctaactct ggcaaatatg ccacgacagc ccggaactcc     780
ttcattgtac taatcatttt tactatatgc ttcgtgcctt atcatgcctt tcgattcatt     840
tacatttctt cacagctaaa tgcatcttct tgctactgga ggaaatcat tcataaaacc      900
aatgagatca tgttggttct ctcctctttc aacagctgct ggatcctgt catgtatttc      960
ctaatgtcca gtaatattcg caaaatcatg tgtcaacttc ttttagaag atttcaaagt     1020
gacacaagca gaagtgaaag cacttcagaa tttaagccag atattcctt gcatgatcta     1080
tctgtgacgg tcaaaatgca gtacagcact aagggtaac                           1119
```

<210> SEQ ID NO 21
<211> LENGTH: 1122
<212> TYPE: DNA
<213> ORGANISM: Rattus norvegicus

<400> SEQUENCE: 21

-continued

```
atgacgacta cagttgacag ctggctttgc tcctctcctg gaatgcactt tataactaat      60
gacagtgacc aagtctcaca aaatttctca ggagtgtcaa atgtcactag ctgtccaatg     120
gatgaaaaat tactgtctac tgtgttaaca actttctact ctgtgatatt catcgtggga     180
ctggttggaa acatcattgc cctttatgta tttctgggca tccaccgcaa aagaaattcc     240
attcaaattt atctacttaa tgtggctgtt gcagaccttc tactcatctt ctgcctccct     300
ttccgcataa tgtatcacat caaccaaaat aggtggacac taggtgtgat tctttgcaaa     360
gttgtgggga cactatttta catgaacatg tacattagta ttattctgct tgggtttatc     420
agtttggatc gatatataaa aatcaaccgg tctatacaac aaagaagggc aataaccacc     480
aagcaaagtg tttacgtttg ctgtgtagtc tggacagttg ctctagctgg atttttaaca     540
atgatcattt tgacactgaa gaagggaggg cacaattcca caatgtgttt ccattacaga     600
gataagcata tgcaaaggg agaagcgatc tttaactttg ctcttgtagt aatgttctgg     660
ctcatttttcc tactgataat cctttcatat attaagattg caagaatct actgaggatt     720
tctaaaagga ggtcaaaatt tcctaactct ggcaaatatg ccacgacagc ccggaactcc     780
ttcattgtac taatcatttt tactatatgc ttcgtgcctt atcatgcctt tcgattcatt     840
tacatttctt cacagctaaa tgcatcttct tgctactgga aggaaatcat tcataaaacc     900
aatgagatca tgttggttct ctcctctttc aacagctgct tggatcctgt catgtatttc     960
ctaatgtcca gtaatattcg caaaatcatg tgtcaacttc tttttagaag atttcaaagt    1020
gacacaagca gaagtgaaag cacttcagaa tttaagccag gatattcctt gcatgatcta    1080
tctgtgacgg tcaaaatgca gtacagcact aagggtaact ga                       1122
```

<210> SEQ ID NO 22
<211> LENGTH: 375
<212> TYPE: PRT
<213> ORGANISM: Mus musculus

<400> SEQUENCE: 22

```
Met Thr Thr Thr Ser Val Asp Ser Trp Leu Cys Ser Ser His Gly Met
1               5                   10                  15

His Phe Ile Thr Asn Tyr Ser Asp Gln Ala Ser Gln Asn Phe Ser Gly
            20                  25                  30

Val Pro Asn Val Thr Ser Cys Pro Met Asp Glu Lys Leu Leu Ser Thr
        35                  40                  45

Val Leu Thr Thr Phe Tyr Ser Val Ile Phe Leu Val Gly Leu Val Gly
    50                  55                  60

Asn Ile Ile Ala Leu Tyr Val Phe Leu Gly Ile His Arg Lys Arg Asn
65                  70                  75                  80

Ser Ile Gln Ile Tyr Leu Leu Asn Val Ala Val Ala Asp Leu Leu Leu
                85                  90                  95

Ile Phe Cys Leu Pro Phe Arg Ile Met Tyr His Ile Asn Gln Asn Lys
            100                 105                 110

Trp Thr Leu Gly Val Ile Leu Cys Lys Val Val Gly Thr Leu Phe Tyr
        115                 120                 125

Met Asn Met Tyr Ile Ser Ile Ile Leu Leu Gly Phe Ile Ser Leu Asp
    130                 135                 140

Arg Tyr Ile Lys Ile Asn Arg Ser Ile Gln Gln Arg Arg Ala Ile Thr
145                 150                 155                 160

Thr Lys Gln Ser Ile Tyr Val Cys Cys Ile Val Trp Thr Val Ala Leu
                165                 170                 175
```

```
Ala Gly Phe Leu Thr Met Ile Ile Leu Thr Leu Lys Lys Gly Gly His
            180                 185                 190

Asn Ser Thr Met Cys Phe His Tyr Arg Asp Arg His Asn Ala Lys Gly
        195                 200                 205

Glu Ala Ile Phe Asn Phe Val Leu Val Val Met Phe Trp Leu Ile Phe
    210                 215                 220

Leu Leu Ile Ile Leu Ser Tyr Ile Lys Ile Gly Lys Asn Leu Leu Arg
225                 230                 235                 240

Ile Ser Lys Arg Arg Ser Lys Phe Pro Asn Ser Gly Lys Tyr Ala Thr
                245                 250                 255

Thr Ala Arg Asn Ser Phe Ile Val Leu Ile Ile Phe Thr Ile Cys Phe
            260                 265                 270

Val Pro Tyr His Ala Phe Arg Phe Ile Tyr Ile Ser Ser Gln Leu Asn
        275                 280                 285

Val Ser Ser Cys Tyr Trp Lys Glu Ile Ile His Lys Thr Asn Glu Ile
    290                 295                 300

Met Leu Val Phe Ser Ser Phe Asn Ser Cys Leu Asp Pro Val Met Tyr
305                 310                 315                 320

Phe Leu Met Ser Ser Asn Ile Arg Lys Ile Met Cys Gln Leu Leu Phe
                325                 330                 335

Arg Arg Phe Gln Ser Glu Ala Ser Arg Ser Glu Ser Thr Ser Glu Phe
            340                 345                 350

Lys Pro Gly His Ser Leu His Asp Leu Ser Val Thr Val Lys Met Pro
        355                 360                 365

Gln Tyr Ser Thr Lys Gly Asn
    370                 375

<210> SEQ ID NO 23
<211> LENGTH: 1125
<212> TYPE: DNA
<213> ORGANISM: Mus musculus

<400> SEQUENCE: 23
atgactacta cttcagttga cagctggctt tgctcctctc atggaatgca ctttataact      60
aattatagtg accaagcctc acaaaatttc tcaggagtgc caaatgtcac tagctgtcca     120
atggatgaaa aattactatc tactgtgtta acaaccttct actctgttat attcctcgtg     180
ggactggttg gaaacatcat tgccctctat gtatttctgg gcattaccg taaaagaaat      240 tccattcaaa tttatctact taatgtggct gttgcagacc ttctactcat cttctgcctc     300
cctttccgca taatgtatca catcaaccaa aacaagtgga cactaggtgt gattctttgt     360
aaagttgtgg ggacactatt ttacatgaac atgtacatta gcattatttt gcttgggttt     420
atcagtttgg atcgctatat aaaaatcaat cggtctatac aacaaagaag ggcaataacc     480
accaagcaaa gtatttatgt ttgctgtata gtatggacgg ttgctcttgc tggatttcta     540
actatgatca ttttgacact gaagaaggga ggtcataatt ccacaatgtg tttccattac     600
agagacagac ataatgcaaa gggagaagca attttaact tgttcttgt agtaatgttc       660 tggcttattt tcctactgat aatcctctca tatattaaga ttggcaagaa tctactgagg     720
atttctaaac ggaggtcaaa atttccaaac tctggcaaat atgctacaac agcccggaac     780
tcctttattg tactgatcat ttttactata tgctttgtgc cttaccatgc ctttcggttc     840
atttacattt cttcacagct aaatgtgtcc tcttgttatt ggaaggaaat cattcacaaa     900
actaacgaga tcatgctggt tttctcctct ttcaacagtt gcctggatcc tgtcatgtat     960
ttcctgatgt ccagtaatat tcgcaaaatc atgtgtcaac ttcttttag aaggtttcaa    1020
```

-continued

```
agtgaagcaa gcagaagtga aagcacttca gaatttaagc caggacattc cttgcatgat    1080
ctgtccgtga cagtcaaaat gccccagtac agcactaagg gtaat                   1125
```

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24

```
gcaacatcac acaagaccag aag                                             23
```

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

```
tgtcaggtcc acgctccat                                                  19
```

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26

```
cttccctgtg caacagcagc atgg                                            24
```

<210> SEQ ID NO 27
<211> LENGTH: 78
<212> TYPE: DNA
<213> ORGANISM: Rattus norvegicus

<400> SEQUENCE: 27

```
gctgagcaac atcacacaag accagaagac ttccctgtgc aacagcagca tggtatggag     60
cgtggacctg acagctgg                                                   78
```

<210> SEQ ID NO 28
<211> LENGTH: 582
<212> TYPE: DNA
<213> ORGANISM: Rattus norvegicus

<400> SEQUENCE: 28

```
ggagcgagat cccgctaaca tcaaatgggg tgatgctggt gctgagtatg tcgtggagtc     60
tactggcgtc ttcaccacca tggagaaggc tggggctcac ctgaagggtg gggccaaaag    120
ggtcatcatc tccgcccctt ccgctgatgc ccccatgttt gtgatgggtg tgaaccacga    180
gaaatatgac aactccctca agattgtcag caatgcatcc tgcaccacca actgcttagc    240 cccccctggcc aaggtcatcc atgacaactt tggcatcgtg aagggctca tgaccacagt    300 ccatgccatc actgccactc agaagactgt ggatggcccc tctggaaagc tgtggcgtga    360
tggccgtggg gcagcccaga acatcatccc tgcatccact ggtgctgcca aggctgtggg    420
caaggtcatc ccagagctga acgggaagct cactggcatg gccttccgtg ttcctacccc    480
```

```
caatgtatcc gttgtggatc tgacatgccg cctggagaaa cctgccaagt atgatgacat    540
caagaaggtg gtgaagcagg cggccgaggg cccactaaag gg                       582
```

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
caaagaagta caaagagcat gtcatttagc                                     30
```

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

```
gaagagactg ttttatatca ttcattttag ta                                  32
```

<210> SEQ ID NO 31
<211> LENGTH: 368
<212> TYPE: PRT
<213> ORGANISM: Cavia porcellus

<400> SEQUENCE: 31

```
Met Ala Thr Thr Ser Val Gly Gly Leu Ser Cys Ser Ser Asp Gly Met
1               5                   10                  15

Arg Phe Val Thr Asn His Ser Asp Gln Ala Pro Gln Asn Phe Ser Glu
            20                  25                  30

Ala Ala Asn Val Thr Ser Cys Tyr Met Glu Glu Gln Leu Leu Ser Thr
        35                  40                  45

Val Leu Thr Ile Phe Tyr Ser Val Ile Phe Ile Val Gly Leu Val Gly
    50                  55                  60

Asn Ile Ile Ala Leu Tyr Val Phe Leu Gly Ile His Arg Lys Arg Asn
65                  70                  75                  80

Ser Ile Gln Ile Tyr Leu Leu Asn Val Ala Ile Ala Asp Leu Leu Leu
                85                  90                  95

Ile Phe Cys Leu Pro Phe Arg Ile Met Tyr His Ile Asn Gln Asn Lys
            100                 105                 110

Trp Thr Leu Gly Val Ile Leu Cys Lys Val Val Gly Thr Leu Phe Tyr
        115                 120                 125

Met Asn Met Tyr Ile Ser Ile Ile Leu Leu Gly Phe Ile Ser Leu Asp
    130                 135                 140

Arg Tyr Ile Lys Ile Asn Arg Ser Ile Gln Gln Arg Arg Ala Ile Thr
145                 150                 155                 160

Thr Lys Gln Ser Ile Tyr Ile Cys Cys Ile Val Trp Ala Ile Ala Leu
                165                 170                 175

Ala Val Phe Leu Thr Met Ile Ile Leu Thr Leu Lys Lys Gly Gly His
            180                 185                 190

Asn Ser Thr Met Cys Phe His Tyr Arg Asp Lys His Asn Ala Lys Gly
        195                 200                 205

Glu Ala Phe Phe Asn Leu Val Leu Val Val Met Phe Trp Leu Ile Phe
    210                 215                 220
```

```
Leu Leu Ile Ile Leu Ser Tyr Ile Lys Ile Gly Lys Asn Leu Leu Arg
225                 230                 235                 240

Ile Ser Lys Arg Arg Ser Lys Phe Pro Asn Ser Gly Lys Tyr Ala Ile
                245                 250                 255

Thr Ala Arg Asn Ser Phe Ile Val Leu Ile Ile Phe Thr Ile Cys Phe
            260                 265                 270

Val Pro Tyr His Gly Phe Arg Phe Ile Tyr Ile Ser Ser Gln Leu Asn
        275                 280                 285

Glu Ser Leu Cys Tyr Trp Lys Glu Ile Val His Lys Thr Asn Glu Ile
    290                 295                 300

Met Leu Val Leu Ser Ser Phe Asn Ser Cys Leu Asp Pro Val Met Tyr
305                 310                 315                 320

Phe Leu Met Ser Ser Asn Ile Arg Lys Ile Met Cys Gln Leu Leu Phe
                325                 330                 335

Arg Arg Phe Gln Gly Glu Ala Ser Arg Ser Glu Ser Thr Ser Glu Phe
            340                 345                 350

Lys Pro Gly Tyr Ser Leu His Asp Thr Ser Val Ala Ala Lys Leu Gln
        355                 360                 365

<210> SEQ ID NO 32
<211> LENGTH: 1107
<212> TYPE: DNA
<213> ORGANISM: Cavia porcellus

<400> SEQUENCE: 32
atggcaacta cttcagtagg gggcttgtct tgctcctccg atgggatgcg ctttgtaact      60
aatcacagtg accaagcccc acagaacttc tcagaagcgg caaatgttac tagctgttac     120
atggaggaac aactgctgtc tactgtgtta acaatattct actctgttat tttcattgtg     180
ggactggttg aaacataat tgccctctac gtatttctgg catccatcg caagagaaat      240 tccattcaga tttacctact taatgtagcc attgcagacc ttctactcat ttctgcctt      300 cctttccgaa taatgtatca tattaaccaa aacaagtgga cattaggtgt gatcctttgc     360
aaggttgtag aacactatt ttatatgaac atgtacatca gcattatttt gcttggattc      420
atcagtttgg atcgctacat aaaaattaat cggtctatac aacaacggag ggcaataaca     480
accaagcaaa gtatttatat ttgctgtata gtatgggcaa ttgctcttgc tgtatttta      540 actatgatta tttaacact taagaaagga gggcataatt ctacaatgtg ttttcattac      600
agagataagc ataatgcaaa aggagaagca tttttaacc ttgttcttgt ggtaatgttc      660
tggctgattt tcctactgat aatcctttca tatattaaga ttggcaaaaa tctactgagg     720
atttctaaaa ggaggtcaaa atttcctaat tctggtaaat atgccattac agcacgaaat     780
tcctttattg tactgatcat ttttaccata tgttttgtcc cttaccatgg ctttcgattc     840
atatacattt cttcacagtt aaatgaatca ttatgttatt ggaaggaaat cgttcacaaa     900
accaatgaga tcatgctggt tctctcatct ttcaatagct gcttagaccc agtcatgtat     960
tttctgatgt ccagtaatat tcgcaaaata atgtgtcaac ttcttttag acgatttcaa    1020 ggtgaagcaa gcagaagtga aagcacttca gaatttaaac caggatattc cctgcatgat   1080
acatctgtag cagctaaact gcagtag                                        1107

<210> SEQ ID NO 33
<211> LENGTH: 29
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 33
gaggaatatg tcatttagca ctttcactt                                              29

<210> SEQ ID NO 34
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
agaggctgca ttatataatt cattttagta tgtt                                        34

<210> SEQ ID NO 35
<211> LENGTH: 381
<212> TYPE: PRT
<213> ORGANISM: Macaca fascicularis

<400> SEQUENCE: 35

Met Arg Ser His Thr Ile Thr Met Thr Thr Thr Ser Val Ser Ser Trp
1               5                   10                  15

Pro Tyr Ser Ser His Arg Met Arg Phe Ile Thr Ser His Ser Asp Gln
            20                  25                  30

Pro Pro Gln Asn Phe Ser Gly Thr Pro Asn Val Thr Thr Cys Pro Met
        35                  40                  45

Asp Glu Lys Leu Leu Ser Thr Val Leu Thr Thr Ser Tyr Ser Val Ile
    50                  55                  60

Phe Ile Val Gly Leu Val Gly Asn Ile Ile Ala Leu Tyr Val Phe Leu
65                  70                  75                  80

Gly Ile His Arg Lys Arg Asn Ser Ile Gln Ile Tyr Leu Leu Asn Val
                85                  90                  95

Val Ile Ala Asp Leu Leu Leu Ile Phe Cys Leu Pro Phe Arg Ile Met
            100                 105                 110

Tyr His Ile Asn Gln Asn Lys Trp Thr Leu Gly Val Ile Leu Cys Lys
        115                 120                 125

Val Val Gly Thr Leu Phe Tyr Met Asn Met Tyr Ile Ser Ile Ile Leu
    130                 135                 140

Leu Gly Phe Ile Ser Leu Asp Arg Tyr Ile Lys Ile Asn Arg Ser Ile
145                 150                 155                 160

Gln Gln Arg Lys Ala Ile Thr Thr Lys Gln Ser Ile Tyr Val Cys Cys
                165                 170                 175

Ile Val Trp Met Leu Ala Leu Gly Gly Phe Leu Thr Met Ile Ile Leu
            180                 185                 190

Thr Leu Lys Lys Gly Gly His Asn Ser Thr Met Cys Phe His Tyr Arg
        195                 200                 205

Asp Lys His Asn Ala Lys Gly Glu Ala Ile Phe Asn Phe Ile Leu Val
    210                 215                 220

Val Met Phe Trp Leu Ile Phe Leu Leu Ile Ile Leu Ser Tyr Ile Lys
225                 230                 235                 240

Ile Gly Lys Asn Leu Leu Arg Ile Ser Lys Arg Ser Lys Phe Pro
                245                 250                 255

Asn Ser Gly Lys Tyr Ala Thr Thr Ala Arg Asn Ser Phe Ile Val Leu
            260                 265                 270

Ile Ile Phe Thr Ile Cys Phe Val Pro Tyr His Ala Phe Arg Phe Ile
        275                 280                 285

```
Tyr Ile Ser Ser Gln Leu Asn Val Ser Cys Tyr Trp Lys Glu Ile
    290                 295                 300

Val His Lys Thr Asn Glu Ile Met Leu Val Leu Ser Ser Phe Asn Ser
305                 310                 315                 320

Cys Leu Asp Pro Val Met Tyr Phe Leu Met Ser Ser Asn Ile Arg Lys
                325                 330                 335

Ile Met Cys Gln Leu Leu Phe Arg Arg Phe Gln Gly Glu Pro Ser Arg
            340                 345                 350

Ser Glu Ser Thr Ser Glu Phe Lys Pro Gly Tyr Ser Leu His Asp Thr
        355                 360                 365

Ser Val Ala Ala Lys Ile His Ser Ser Ser Lys Ser Thr
    370                 375                 380

<210> SEQ ID NO 36
<211> LENGTH: 1146
<212> TYPE: DNA
<213> ORGANISM: Macaca fascicularis

<400> SEQUENCE: 36
```

| | | | | | |
|---|---|---|---|---|---|
| atgagaagtc | acaccataac | aatgacgaca | acttcagtca | gcagctggcc | ttactcctcc | 60 |
| cacagaatgc | gctttataac | cagtcatagc | gaccaaccgc | cacaaaactt | ctcaggaaca | 120 |
| ccaaatgtta | ctacctgtcc | catggatgaa | aaattactat | ctactgtgtt | aacaacatct | 180 |
| tactctgtta | ttttcattgt | gggactggtt | gggaacataa | tcgccctcta | tgtatttctg | 240 |
| ggtattcacc | gcaaaagaaa | ttccattcaa | atttatctac | ttaatgtagt | cattgcagac | 300 |
| ctcctactca | tcttctgcct | cccttcccga | ataatgtatc | acattaacca | aaacaagtgg | 360 |
| acactaggtg | tgattctgtg | caaggttgtg | ggaacactat | tttatatgaa | catgtacatt | 420 |
| agcattattt | tgcttggatt | catcagtttg | gatcgctata | taaaaattaa | tcggtctata | 480 |
| cagcaacgga | aggcaataac | aaccaaacaa | agtatttatg | tctgttgtat | agtatggatg | 540 |
| cttgctcttg | gtggattcct | aactatgatt | attttaacac | ttaagaaagg | ggggcataat | 600 |
| tccacaatgt | gtttccatta | tagagataag | cataatgcaa | aaggagaagc | catttttaac | 660 |
| ttcattcttg | tggtaatgtt | ctggctaatt | ttcttactaa | taatcctttc | atatattaag | 720 |
| attgggaaga | atctattgag | gatttctaaa | aggaggtcaa | aatttcctaa | ttctggtaaa | 780 |
| tatgccacta | cagcccggaa | ctccttttatt | gtacttatca | tttttactat | atgttttgtt | 840 |
| ccctatcatg | cctttcgatt | catctacatt | tcttcacagc | taaatgtatc | gtcttgctac | 900 |
| tggaaagaaa | ttgttcacaa | aaccaatgag | atcatgctgg | ttctctcatc | tttcaatagt | 960 |
| tgcttagatc | cagtcatgta | tttcctgatg | tccagtaaca | ttcgcaaaat | aatgtgccaa | 1020 |
| cttcttttta | gacgatttca | aggtgaacca | agtaggagtg | aaagcacttc | agaatttaaa | 1080 |
| ccaggatact | ccctgcatga | tacatctgtg | gcagcaaaaa | tacactctag | ttctaaaagt | 1140 |
| acctga | | | | | | 1146 |

```
<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      primer <400> SEQUENCE: 37
atgtggctgt tgcagaccct cta                                           23
```

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cacacctagt gtccacctat tttgg                                       25

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
tcatcttctg cctcccttc cgca                                         24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
acacctagtg tccacttgtt ttgg                                        24

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cgacaacttc agtcagcagc tg                                          22

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ggttggtcgc tatgattggt ta                                          22

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 43
ccttactcct cccacagaat gcgctt                                      26

<210> SEQ ID NO 44

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ccaacttcca atgctctcct aatg                                          24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gccgagtaga cctcatagtg acct                                          24

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
tggctaagga ccaagaccat ccaactcatc                                    30

<210> SEQ ID NO 47
<211> LENGTH: 137
<212> TYPE: DNA
<213> ORGANISM: Rattus norvegicus

<400> SEQUENCE: 47
ctaccccaac ttccaatgct ctcctaatgg agaagttaga gtcacagaag gagtggctaa   60
ggaccaagac catccaactc atcttgaaag cacttgaaga atttctaaag gtcactatga  120
ggtctactcg gcaaacc                                                 137

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tccgagatgt ggaactggc                                                19

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
agacaccgcc tggagttctg                                               20

<210> SEQ ID NO 50
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 50
aggaggcgct ccccaaaaag atgg                                           24

<210> SEQ ID NO 51
<211> LENGTH: 83
<212> TYPE: DNA
<213> ORGANISM: Rattus norvegicus

<400> SEQUENCE: 51
catgatccga gatgtggaac tggcagagga ggcgctcccc aaaaagatgg ggggcctcca    60
gaactccagg cggtgtctgt gcc                                            83

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cgacgctgtc atcgatttct ccect                                          25

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gaagctgaag accctctgga taca                                           24

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
ctccactgcc ttgcttttat tctc                                           24

<210> SEQ ID NO 55
<211> LENGTH: 90
<212> TYPE: DNA
<213> ORGANISM: Rattus norvegicus

<400> SEQUENCE: 55
gggagagaag ctgaagaccc tctggataca gctgcgacgc tgtcatcgat ttctcccctg    60
tgagaataaa agcaaggcag tggagcaggt                                     90
```